US008183271B2

(12) United States Patent
Bartel et al.

(10) Patent No.: US 8,183,271 B2
(45) Date of Patent: May 22, 2012

(54) TETRAZOLE DERIVATIVES AND THEIR USE FOR THE TREATMENT OF CARDIOVASCULAR DISEASES

(75) Inventors: Stephan Bartel, Kürten (DE); Michael Hahn, Langenfeld (DE); Wahed Ahmed Moradi, Monheim (DE); Eva-Maria Becker, Wuppertal (DE); Thomas Rölle, Leverkusen (DE); Johannes-Peter Stasch, Solingen (DE); Karl-Heinz Schlemmer, Wuppertal (DE); Frank Wunder, Wuppertal (DE); Andreas Knorr, Erkrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 159 days.

(21) Appl. No.: 12/085,543

(22) PCT Filed: Oct. 9, 2006

(86) PCT No.: PCT/EP2006/009727
§ 371 (c)(1),
(2), (4) Date: Feb. 17, 2009

(87) PCT Pub. No.: WO2007/045370
PCT Pub. Date: Apr. 26, 2007

(65) Prior Publication Data
US 2009/0215843 A1 Aug. 27, 2009

(30) Foreign Application Priority Data
Oct. 21, 2005 (DE) .......................... 10 2005 050 375

(51) Int. Cl.
*A61K 31/41* (2006.01)
*C07D 257/04* (2006.01)

(52) U.S. Cl. ....................................... 514/381; 548/253
(58) Field of Classification Search ................... 548/253; 514/381
See application file for complete search history.

(56) References Cited

U.S. PATENT DOCUMENTS

| | | |
|---|---|---|
| 6,180,656 B1 | 1/2001 | Furstner et al. |
| 6,387,940 B1 | 5/2002 | Straub et al. |
| 6,410,740 B1 | 6/2002 | Straub et al. |
| 6,414,009 B1 | 7/2002 | Straub et al. |
| 6,451,805 B1 | 9/2002 | Straub et al. |
| 6,462,068 B1 | 10/2002 | Straub et al. |
| 6,864,287 B1 * | 3/2005 | Alonso-Alija et al. ....... 514/522 |
| 7,087,644 B1 | 8/2006 | Alonso-Alija et al. |
| 2004/0082798 A1 | 4/2004 | Alonso-Alija et al. |
| 2004/0176446 A1 | 9/2004 | Alonso-Alija et al. |
| 2007/0179139 A1 | 8/2007 | Alonso-Alija et al. |
| 2008/0058314 A1 | 3/2008 | Alonso-Alija et al. |

FOREIGN PATENT DOCUMENTS

| | | |
|---|---|---|
| EP | 0341551 A1 | 11/1989 |
| WO | WO-98/16223 A1 | 4/1998 |
| WO | WO-98/16507 A2 | 4/1998 |
| WO | WO-98/23619 A1 | 6/1998 |
| WO | WO-01/19355 | 3/2001 |
| WO | WO-01/19355 A2 | 3/2001 |
| WO | WO-01/19776 | 3/2001 |
| WO | WO-01/19778 | 3/2001 |
| WO | WO-01/19780 A2 | 3/2001 |
| WO | WO-02/070462 A1 | 9/2002 |
| WO | WO-02/070510 A2 | 9/2002 |

OTHER PUBLICATIONS

Golub et al., Science, vol. 286, Oct. 15, 1999, pp. 531-537.*
Decousus et al. Thrombosis Research 2007, 120, S51-S61.*
Giron, D. J. Therm. Anal. Cal. 2001, 64, pp. 37-60.*
Giron, D. J. Therm. Anal. Cal. 2002, 68, pp. 335-357.*
Souillac, et al., Characterization of Delivery Systems, Differential Scanning Calorimetry, pp. 217-218 (in Encyclopedia of Controlled Drug Delivery, 1999, John Wiley & sons, pp. 212-227).*
B. Rodriquez-Spong et al. Advanced Drug Delivery Reviews, 2004, 56, pp. 241-274.*
Demko and Sharpless, J. Org. Chem. 2001, 66, 7945-7950.*
Patani et al. Chem. Rev. 1996, 96, 3147-3176.*
NIH, Primary Prevention of Hypertension: Clinical and Public Health Advisory from the National High Blood Pressure Education Program, 2002, iv-17.*
Mayo Clinic, Heart failure: Prevention, http://www.mayoclinic.com/healthy/heart-failure/DS00061/DSECTION=prevention, accessed Apr. 4, 2011.*
Schocken et al. Circulation, 2008, 117, 2544-2565.*
FN Ko et al.: "YC-1, A Novel Activator of Platelet Guanylate Cyclase," Blood, 84, 1994, pp. 4226-4233.
A. Mulsch et al.: "Effect of YC-1, an NO-independent, superoxide-Sensitive Stimulator of Soluble Guanylyl Cyclase, on Smooth Muscle Responsiveness to Nitrovasodilators," British Journal of Pharmacology, 120, 1997, pp. 681-689.
D. B. Glass et al.: "Stimulation of Human Platelet Guanylate Cyclase by Fatty Acids," The Journal of Biological Chemistry, vol. 252, No. 4, Feb. 25, 1977, pp. 1279-1285.
D. J. Pettibone et al.: "A Structurally Novel Stimulator of Guanylate Cyclase with Long-Lasting Hypotensive Activity in the Dog," European Journal of Pharmacology, 116, 1985, pp. 307-312.
S-M Yu et al.: "Vasorelaxant Effect of Isoliquiritigenin, a Novel Soluble Guanylate Cyclase Activator, in Rat Aorta," British Journal of Pharmacology, 114, 1995, pp. 1587-1594.
R. Gerzer et al.: "Soluble Guanylate Cyclase Purified from Bovine Lung Contains Heme and Copper," FEBS Letters, vol. 132, No. 1, Sep. 1981, pp. 71-74.
M. Hoenicka et al.: "Purified Soluble Guanylyl Cyclase Expressed in a Baculovirus/Sf9 System: Stimulation by YC-1, Nitirc Oxide, and Carbon Monoxide," J. Mol. Med, 77, 1999, pp. 14-23.

(Continued)

Primary Examiner — Joseph Kosack
Assistant Examiner — Matthew Coughlin
(74) Attorney, Agent, or Firm — Karen B. King; Thomas C. Blankinship; Jonathan R. Harris

(57) ABSTRACT

The present application relates to novel tetrazole derivatives, processes for their preparation, their use for the treatment and/or prophylaxis of diseases, and their use for producing medicaments for the treatment and/or prophylaxis of diseases, especially for the treatment and/or prevention of cardiovascular disorders.

8 Claims, No Drawings

OTHER PUBLICATIONS

L. J. Ignarro: "Regulation of Cytosolic Guanylyl Cyclase by Porphyrins and Metalloporphyrins," Advances in Pharmacology, vol. 26, 1994, pp. 35-65.

A. Mulsch et al.: "Potentiation of Vascular Responses to No-Donors by an No-Independent Activator of Soluble Guanylyl Cyclase," Anunyn Schmiedebergs Arch. Pharmacol. 355, R47.

* cited by examiner

TETRAZOLE DERIVATIVES AND THEIR USE FOR THE TREATMENT OF CARDIOVASCULAR DISEASES

RELATED APPLICATIONS/PATENTS AND INCORPORATION BY REFERENCE

This application is a National Stage Application filed under 35 U.S.C. §371 based on International Application No. PCT/EP2006/009727, filed Oct. 9, 2006, which claims priority to German Patent Application Number 102005050375.6, filed Oct. 21, 2005, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel tetrazole derivatives, processes for their preparation, their use for the treatment and/or prophylaxis of diseases, and their use for producing medicaments for the treatment and/or prophylaxis of diseases, especially for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole [YC-1, Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223, WO 98/16507 and WO 98/23619).

The above-described stimulators of soluble guanylate cyclase stimulate the enzyme either directly via the heme group (carbon monoxide, nitric oxide or diphenyliodonium hexafluorophosphate) by interacting with the iron center of the heme group and a change in conformation which results therefrom and leads to an increase in the enzymic activity [Gerzer et al., FEBS Lett. 132 (1981), 71] or via a heme-dependent mechanism which is independent of NO but leads to a potentiation of the stimulating effect of NO or CO [e.g. YC-1, Hoenicka et al., J. Mol. Med. 77 (1999) 14; or the pyrazole derivatives described in WO 98/16223, WO 98/16507 and WO 98/23619].

It has not been possible to confirm the stimulating effect, asserted in the literature, of isoliquiritigenin and of fatty acids such as, for example, of arachidonic acid, prostaglandin endoperoxides and fatty acid hydroperoxides on soluble guanylate cyclase [cf.; for example, Hoenicka et al., J. Mol. Med. 77 (1999), 14].

If the heme group is removed from soluble guanylate cyclase, the enzyme still shows a detectable basal catalytic activity, i.e. cGMP is still produced. The remaining basal catalytic activity of the heme-free enzyme cannot be stimulated by any of the aforementioned known stimulators.

Stimulation of heme-free soluble guanylate cyclase by protoporphyrin IX has been described [Ignarro et al., Adv. Pharmacol. 26 (1994), 35]. However, protoporphyrin IX can be regarded as a mimic of the NO-heme adduct, which is why addition of protoporphyrin IX to soluble guanylate cyclase ought to lead to production of a structure of the enzyme corresponding to the heme-containing soluble guanylate cyclase which is stimulated by NO. This is also verified by the fact that the stimulating effect of protoporphyrin IX is increased by the NO-independent but heme-dependent stimulator YC-1 described above [Mulsch et al., Naunyn Schmiedebergs Arch. Pharmacol. 355, R47].

In contrast to the above-described stimulators of soluble guanylate cyclase, the compounds of the present invention are able to activate both the heme-containing and the heme-free form of soluble guanylate cyclase. Thus, with these novel activators, the enzyme is stimulated via a heme-independent pathway, which is also verified by the facts that the novel activators firstly show no synergistic effect with NO on the heme-containing enzyme, and secondly the effect of these novel activators cannot be blocked by the heme-dependent inhibitor of soluble guanylate cyclase 1H-1,2,4-oxadiazole-(4,3-a)-quinoxalin-1-one (ODQ).

EP 0 341 551-A1 discloses alkenoic acid derivatives as leucotriene antagonists for the treatment of disorders of the circulatory and respiratory systems. WO 01/19355, WO 01/19776, WO 01/19778, WO 01/19780, WO 02/070462 and WO 02/070510 describe dicarboxylic acid and amino dicarboxylic acid derivatives as stimulators of soluble guanylate cyclase for the treatment of cardiovascular disorders. However, it has emerged that these compounds have disadvantages in relation to their pharmacokinetic properties, such as, in particular, a low bioavailability and/or an only short duration of action after oral administration.

It was therefore an object of the present invention to provide novel compounds which act as activators of soluble guanylate cyclase but do not have the aforementioned disadvantages of the prior art compounds.

This object is achieved by the compounds described in the present invention. These compounds differ structurally in comparison with the compounds of the prior art by a tetrazole group in conjunction with a 1,4-diphenylbut-1-en-3-yl or 1,5-diphenylpent-1-en-3-yl core structure.

The present invention relates specifically to compounds of the general formula (I)

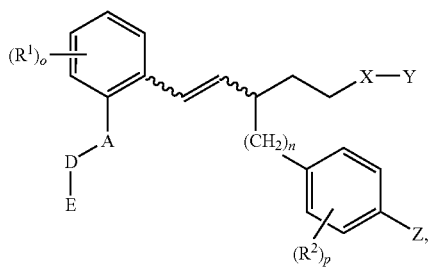

in which
A is O or $CH_2$,
D is a bond or is $(C_1-C_7)$-alkanediyl, $(C_2-C_7)$-alkenediyl or $(C_2-C_7)$-alkynediyl,
E is hydrogen, trifluoromethyl or a group of the formula

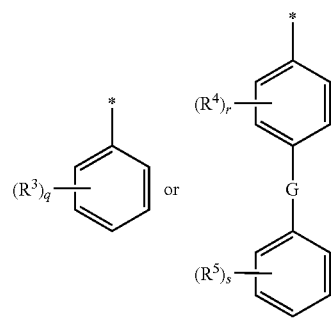

in which * means the point of linkage to the group D and G is a bond, $CH_2$, —$CH_2$—$CH_2$— or —CH=CH—,
X is —$CH_2$—$CH_2$— or a group of the formula

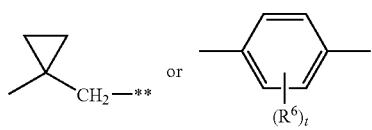

in which ** means the point of linkage to the group Y,
Y is carboxyl
and
Z is a group of the formula

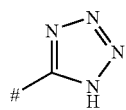

or
Y is a group of the formula

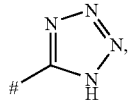

in which # means the respective point of linkage,
and
Z is carboxyl,
n is the number 1 or 2,
$R^1$, $R^2$, $R^3$, $R^4$, $R^5$ and $R^6$ are independently of one another substituents selected from the series halogen, $(C_1-C_6)$-alkyl, trifluoromethyl, $(C_1-C_6)$-alkoxy, trifluoromethoxy, cyano and nitro,
and
o, p, q, r, s and t are independently of one another each the number 0, 1, 2, 3 or 4,
where in the case where $R^1$, $R^2$, $R^3$, $R^4$, $R^5$ or $R^6$ occur more than once, their meanings may in each case be identical or different,
and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

The group

in formula (I) means that this CC double bond can be present in a cis or in a trans configuration. Both isomeric forms are included in the present invention. Preference is given to compounds of the formula (I) having a trans arrangement of this double bond.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

$(C_1-C_6)$-Alkyl and $(C_1-C_4)$-alkyl are in the context of the invention a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, iso-butyl, sec-butyl, tert-butyl, 1-ethylpropyl, n-pentyl and n-hexyl.

$(C_1-C_7)$-Alkanediyl is in the context of the invention a straight-chain or branched divalent alkyl radical having 1 to 7 carbon atoms. A straight-chain alkanediyl radical having 1 to 6 carbon atoms is preferred. Examples which may be preferably mentioned are: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl, pentane-1,5-diyl, pentane-2,4-diyl, 3-methylpentane-2,4-diyl and hexane-1,6-diyl.

$(C_2-C_7)$-Alkenediyl is in the context of the invention a straight-chain or branched divalent alkenyl radical having 2 to 7 carbon atoms and up to 3 double bonds. A straight-chain alkenediyl radical having 2 to 6 carbon atoms and up to 2 double bonds is preferred. Examples which may be preferably mentioned are: ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl.

$(C_2-C_7)$-Alkynediyl is in the context of the invention a straight-chain or branched divalent alkynyl radical having 2 to 7 carbon atoms and up to 3 triple bonds. A straight-chain alkynediyl radical having 2 to 6 carbon atoms and up to 2 triple bonds is preferred. Examples which may be preferably mentioned are: ethyne-1,2-diyl, propyne-1,3-diyl, but-1-yne-1,4-diyl, but-1-yne-1,3-diyl, but-2-yne-1,4-diyl, pent-2-yne-1,5-diyl, pent-2-yne-1,4-diyl and hex-3-yne-1,6-diyl.

$(C_1-C_6)$-Alkoxy and $(C_1-C_4)$-alkoxy are in the context of the invention a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy, n-butoxy, tert-butoxy, n-pentoxy and n-hexoxy.

Halogen in the context of the invention includes fluorine, chlorine, bromine and iodine. Chlorine or fluorine are preferred.

If radicals in the compounds according to the invention are substituted, the radicals may, unless otherwise specified, be substituted one or more times. In the context of the present invention, all radicals which occur more than once have a mutually independent meaning. Substitution by one, two or three identical or different substituents is preferred. Substitution by one substituent is very particularly preferred.

Preference is given in the context of the present invention to compounds of the formula (I) in which
A is O,
D is $(C_1-C_7)$-alkanediyl,
E is hydrogen, trifluoromethyl or is a group of the formula

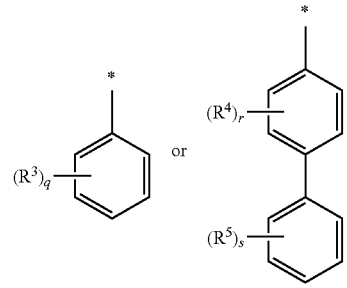

in which * means the point of linkage to the group D,
X is —CH$_2$—CH$_2$— or a group of the formula

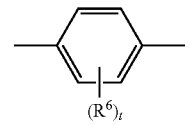

Y is carboxyl
and
Z is a group of the formula

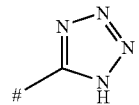

or
Y is a group of the formula

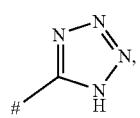

in which # means the respective point of linkage,
and
Z is carboxyl,
n is the number 1 or 2, $R^1$, $R^3$, $R^4$ and $R^5$ are independently of one another a substituent selected from the series fluorine, chlorine, bromine, ($C_1$-$C_4$)-alkyl, trifluoromethyl, ($C_1$-$C_4$)-alkoxy and trifluoromethoxy, o, q, r and s are independently of one another each the number 0, 1 or 2, where in the case where $R^1$, $R^3$, $R^4$ or $R^5$ occur more than once, their meanings may in each case be identical or different, $R^2$ and $R^6$ are each fluorine, and p and t are independently of one another each the number 0 or 1, and the salts, solvates and solvates of the salts thereof.

Particular preference is given in the context of the present invention to compounds of the formula (I-A)

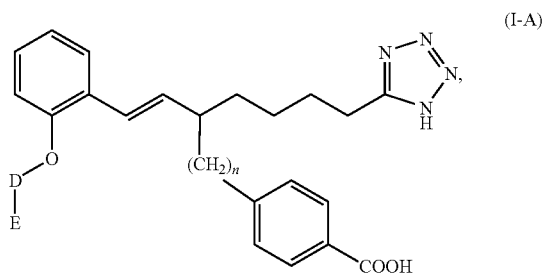

(I-A)

in which

D is ($C_1$-$C_7$)-alkanediyl,

E is hydrogen or a group of the formula

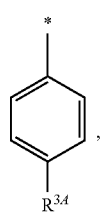

in which * means the point of linkage to the group D, and $R^{3A}$ is hydrogen, fluorine, chlorine, methyl, tert-butyl, trifluoromethyl, methoxy or trifluoromethoxy, and n is the number 1 or 2, and the salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the invention of the formula (I) characterized in that either

[A] compounds of the formula (II-1)

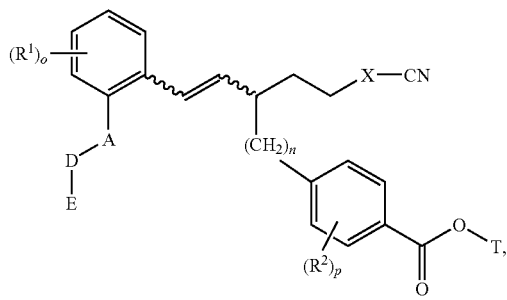

(II-1)

in which $R^1$, $R^2$, A, D, E, X, n, o and p each have the meanings indicated above, and T is ($C_1$-$C_4$)-alkyl, are reacted with an alkali metal azide in the presence of ammonium chloride or with trimethylsilyl azide, where appropriate in the presence of a catalyst, in an inert solvent to give compounds of the formula (III-1)

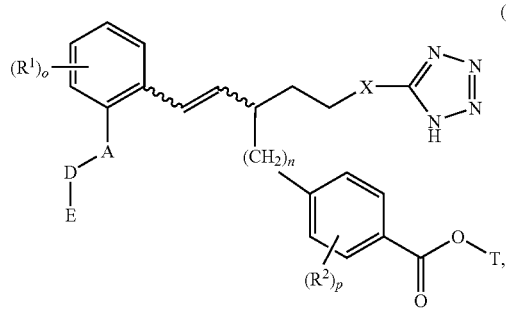

(III-1)

in which $R^1$, $R^2$, A, D, E, X, n, o, p and T each have the meanings indicated above, or

[B] compounds of the formula (II-2)

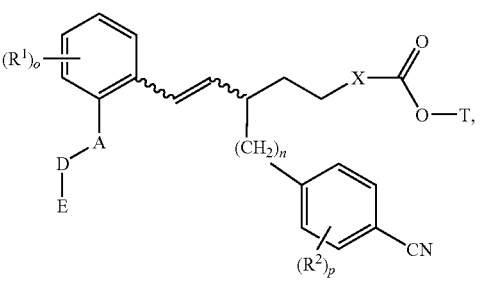

(II-2)

in which $R^1$, $R^2$, A, D, E, X, n, o, p and T each have the meanings indicated above, are reacted with an alkali metal azide in the presence of ammonium chloride or with trimethylsilyl azide, where appropriate in the presence of a catalyst, in an inert solvent to give compounds of the formula (III-2)

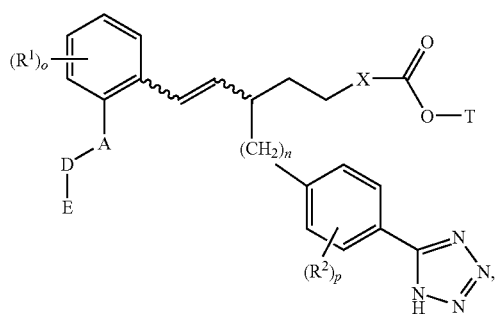

(III-2)

in which $R^1$, $R^2$, A, D, E, X, n, o, p and T each have the meanings indicated above,
and the resulting compounds of the formula (III-1) or (III-2) are converted by hydrolysis of the ester group —C(O)OT into the corresponding carboxylic acids of the formula (I),
and the compounds of the formula (I) are separated where appropriate by methods known to the skilled person into their enantiomers and/or diastereomers, and/or where appropriate reacted with the appropriate (i) solvents and/or (ii) bases or acids to give the solvates, salts and/or solvates of the salts thereof.

Examples of inert solvents for process step (II-1)→(III-1) or (II-2)→(III-2) are ethers such as diethyl ether, dioxane, tetrahydrofuran, glycol dimethyl ether or diethylene glycol dimethyl ether, hydrocarbons such as benzene, toluene, xylene, hexane, cyclohexane or petroleum fractions, or other solvents such as dimethyl sulfoxide, dimethylformamide, N,N'-dimethylpropyleneurea (DMPU) or N-methylpyrrolidone (NMP). It is likewise possible to employ mixtures of said solvents. Toluene is preferably used.

A particularly suitable azide reagent for this process step is sodium azide in the presence of ammonium chloride or trimethylsilyl azide. The latter reaction can advantageously be carried out in the presence of a catalyst. Compounds suitable for this purpose are in particular di-n-butyltin oxide, trimethylaluminum or zinc bromide. Trimethylsilyl azide in combination with di-n-butyltin oxide is preferably used.

The process step (II-1)→(III-1) or (II-2)→(III-2) is generally carried out in a temperature range from +50° C. to +150° C., preferably at +60° C. to +110° C. The reaction can be carried out under atmospheric, elevated or reduced pressure (e.g. from 0.5 to 5 bar). It is generally carried out under atmospheric pressure.

Hydrolysis of the carboxylic esters in process step (II-1)→(III-1) or (II-2)→(III-2) takes place by conventional methods, by treating the esters in inert solvents with acids or bases, and with the latter converting the initially produced salts into the free carboxylic acids by treatment with acid. The ester cleavage in the case of tert-butyl esters preferably takes place with acids.

Inert solvents suitable for hydrolysis of the carboxylic esters are water or the organic solvents usual for ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, acetonitrile, dichloromethane, dimethylformamide or dimethyl sulfoxide. It is likewise possible to employ mixtures of the solvents mentioned. In the case of a basic ester hydrolysis, preferably mixtures of water with dioxane, tetrahydrofuran, methanol and/or ethanol are employed. In the case of reaction with trifluoroacetic acid, preferably dichloromethane is used, and in the case of reaction with hydrogen chloride, preferably tetrahydrofuran, diethyl ether, dioxane or water is used.

Suitable bases for the ester hydrolysis are the usual inorganic bases. These preferably include alkali metal or alkaline earth metal hydroxides such as, for example, sodium, lithium, potassium or barium hydroxide, or alkali metal or alkaline earth metal carbonates such as sodium, potassium or calcium carbonate. Use is particularly preferably made of sodium or lithium hydroxide.

Suitable acids for the ester cleavage are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, where appropriate with addition of water. Hydrogen chloride or trifluoroacetic acid are preferred in the case of the tert-butyl esters, and hydrochloric acid in the case of the methyl esters.

The ester cleavage generally takes place in a temperature range from 0° C. to +100° C., preferably at +20° C. to +60° C. The reactions can be carried out under atmospheric, elevated or reduced pressure (e.g. from 0.5 to 5 bar). They are generally carried out under atmospheric pressure.

The compounds of the formulae (II-1) and (II-2) can be prepared by the processes described in EP 0 341 551-A1, WO 01/19355, WO 01/19776 and WO 01/19778 (compare also reaction schemes 1-14 hereinafter); the content relating thereto in these publications is hereby expressly included as part of the disclosure.

Separation of the compounds of the invention into the corresponding enantiomers and/or diastereomers can take place where appropriate, depending on expediency, even at the stage of the compounds (II-1), (II-2), (III-1), (III-2) or of the phenolic precursors thereof depicted in schemes 9 and 11-14, which are then reacted further in separated form in accordance with the described process sequences. Such a fractionation of the stereoisomers can be carried out by conventional methods known to the skilled person; chromatographic methods or separation via diastereomeric salts are preferably used.

The preparation of the compounds of the invention can be illustrated by the following synthesis schemes:

Scheme 1

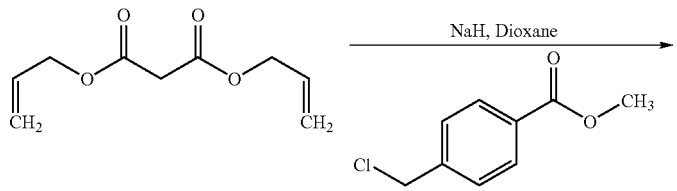

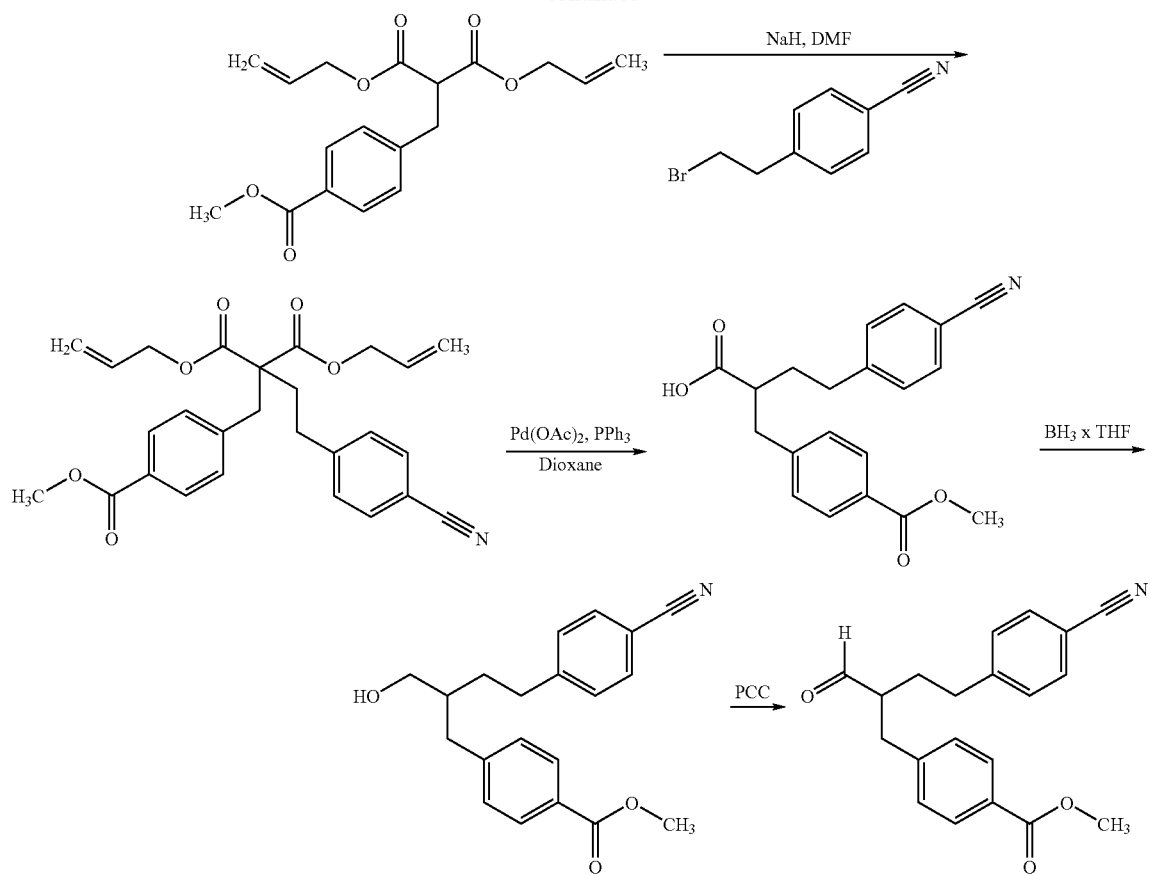
Scheme 2
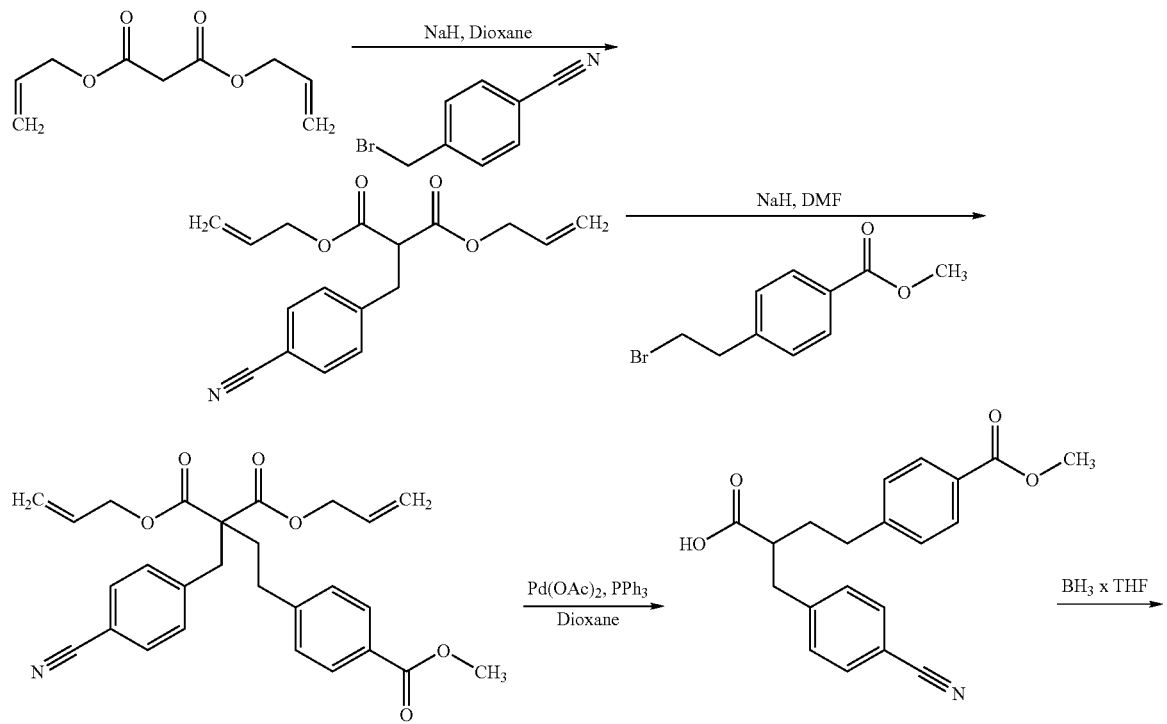

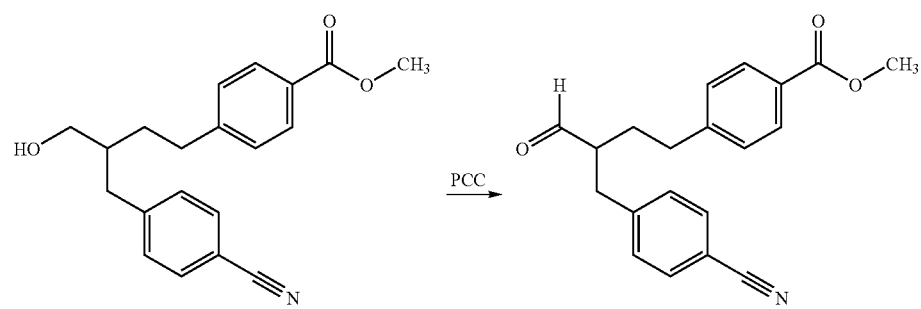
Scheme 3
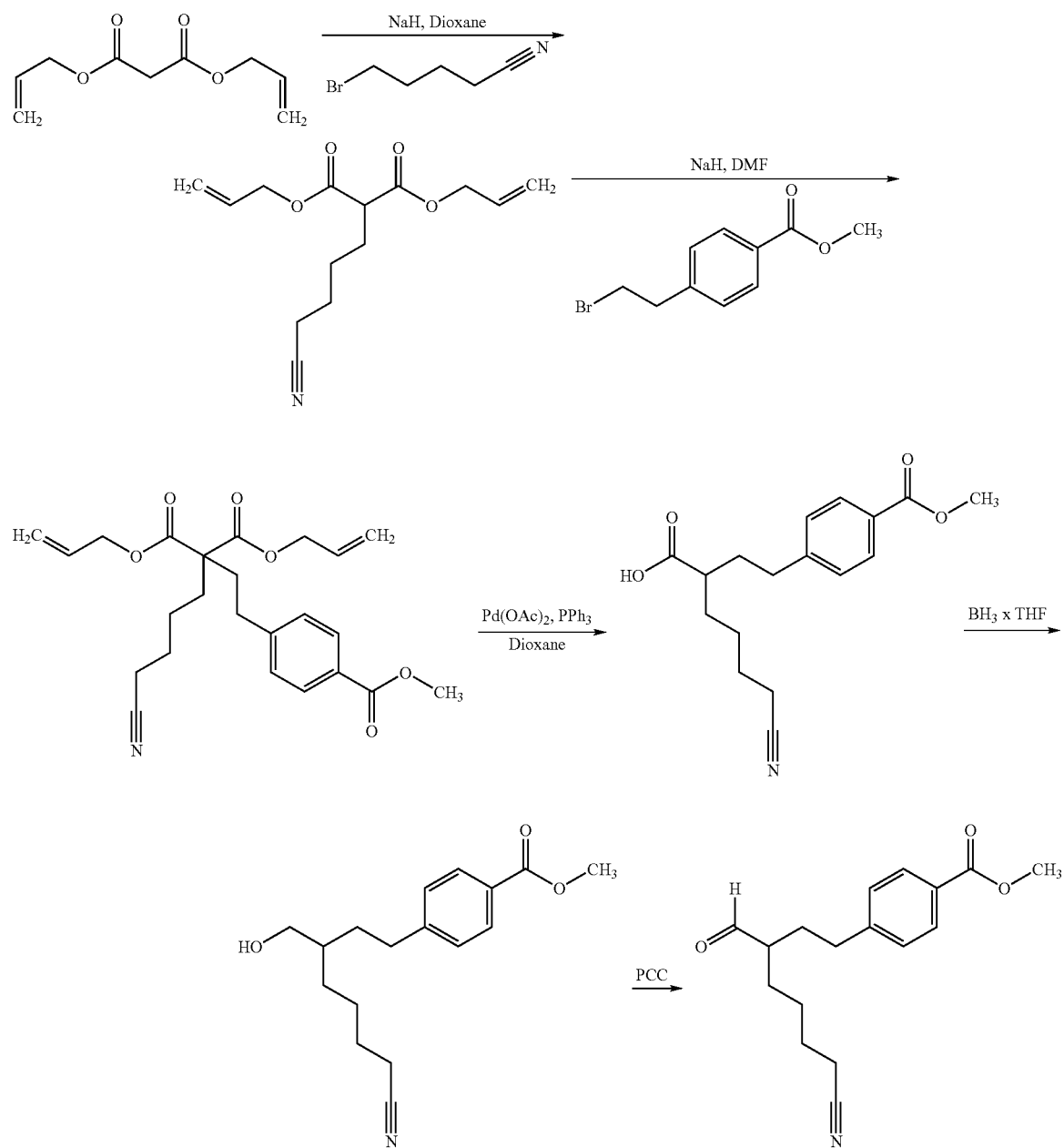

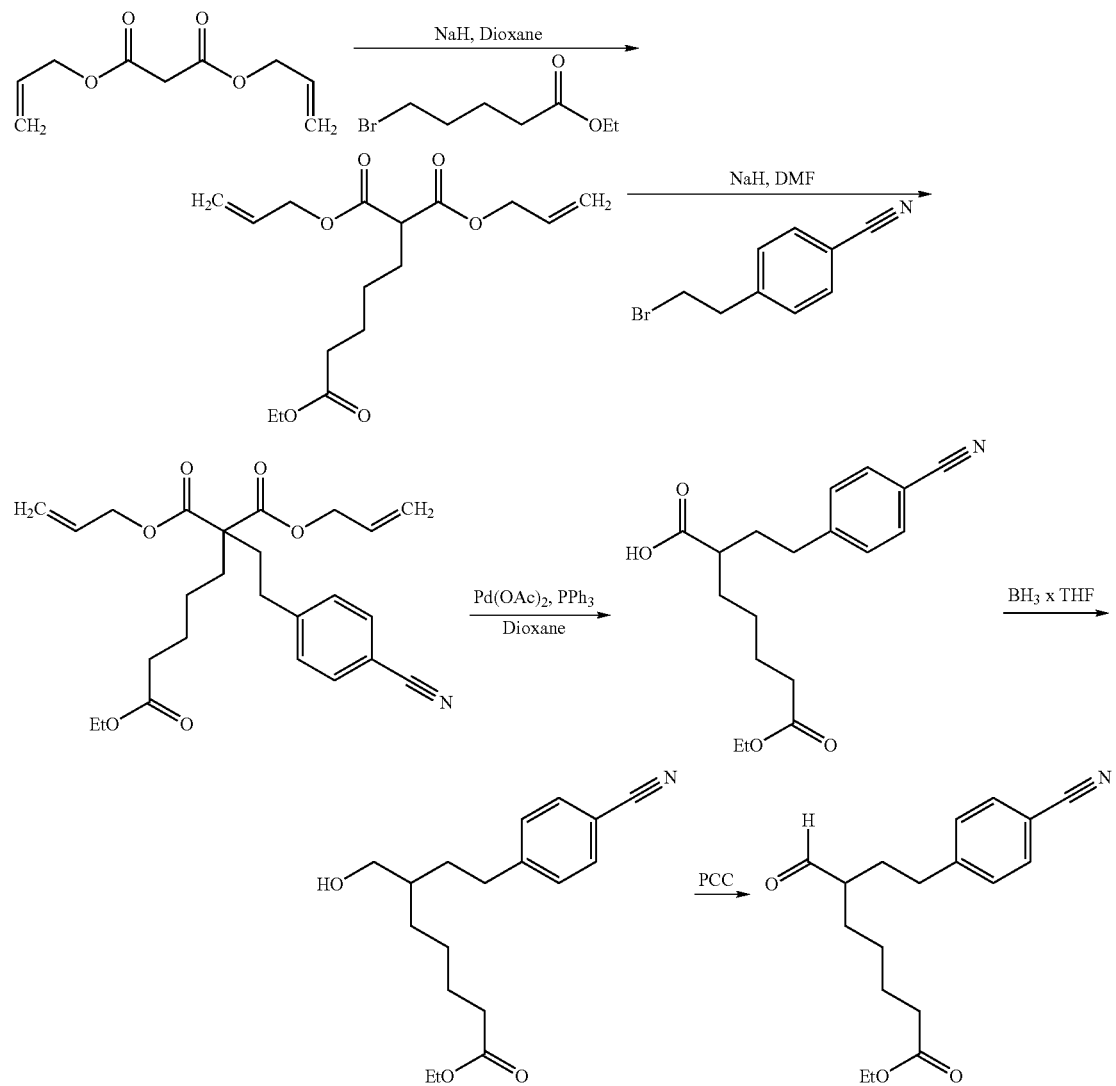
Scheme 4
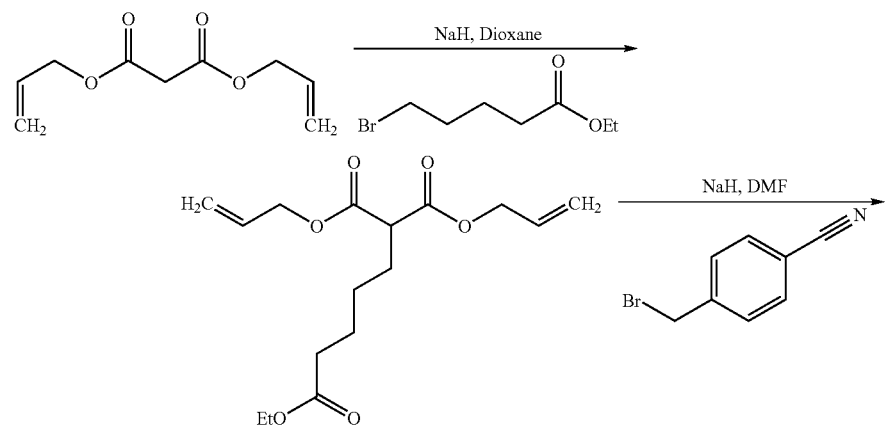
Scheme 5

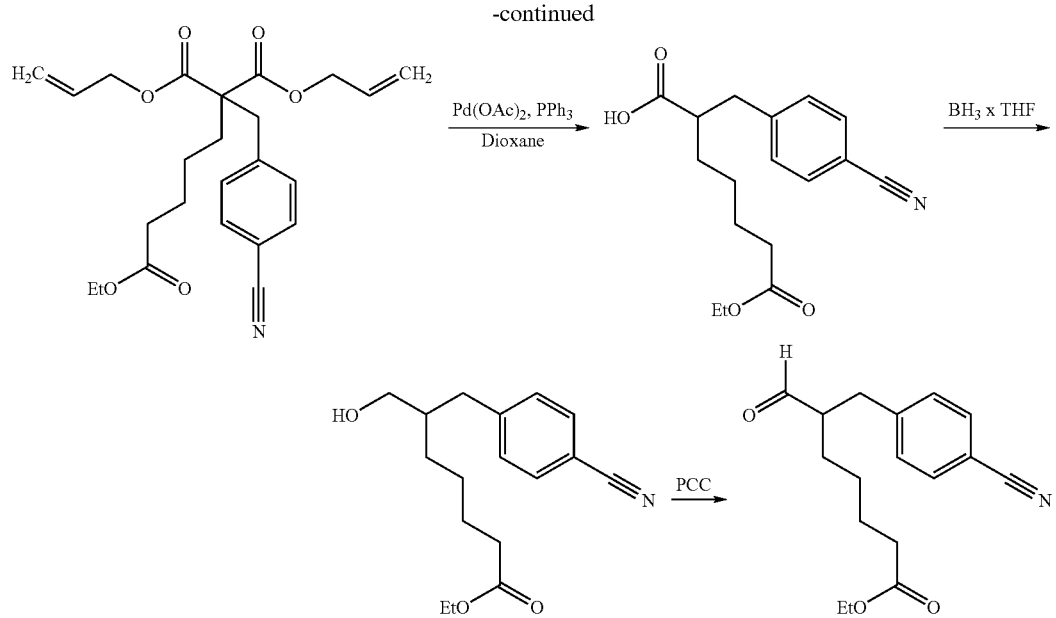
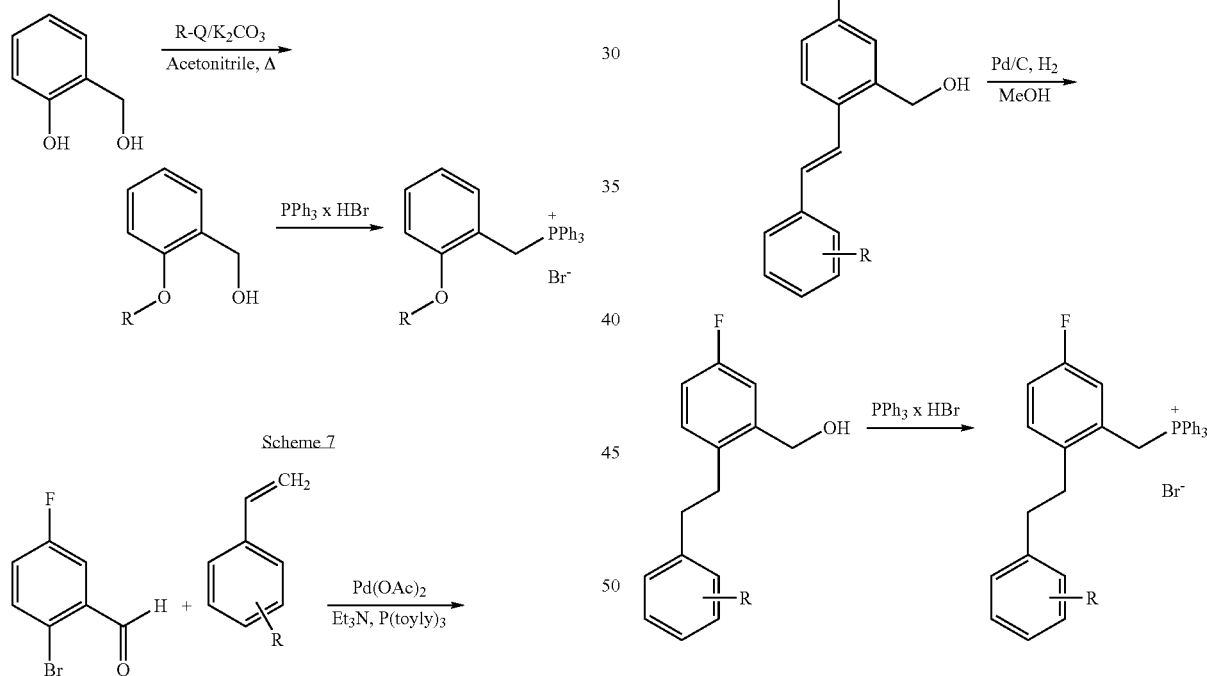
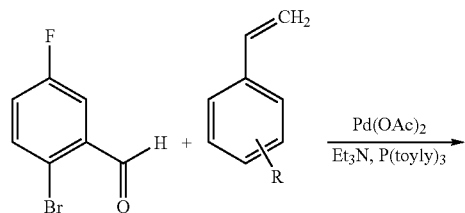
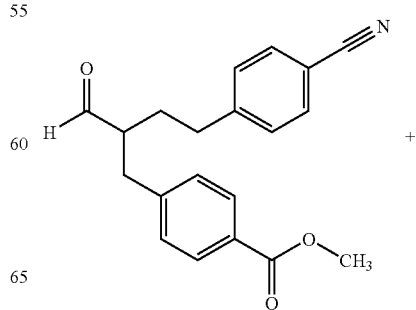

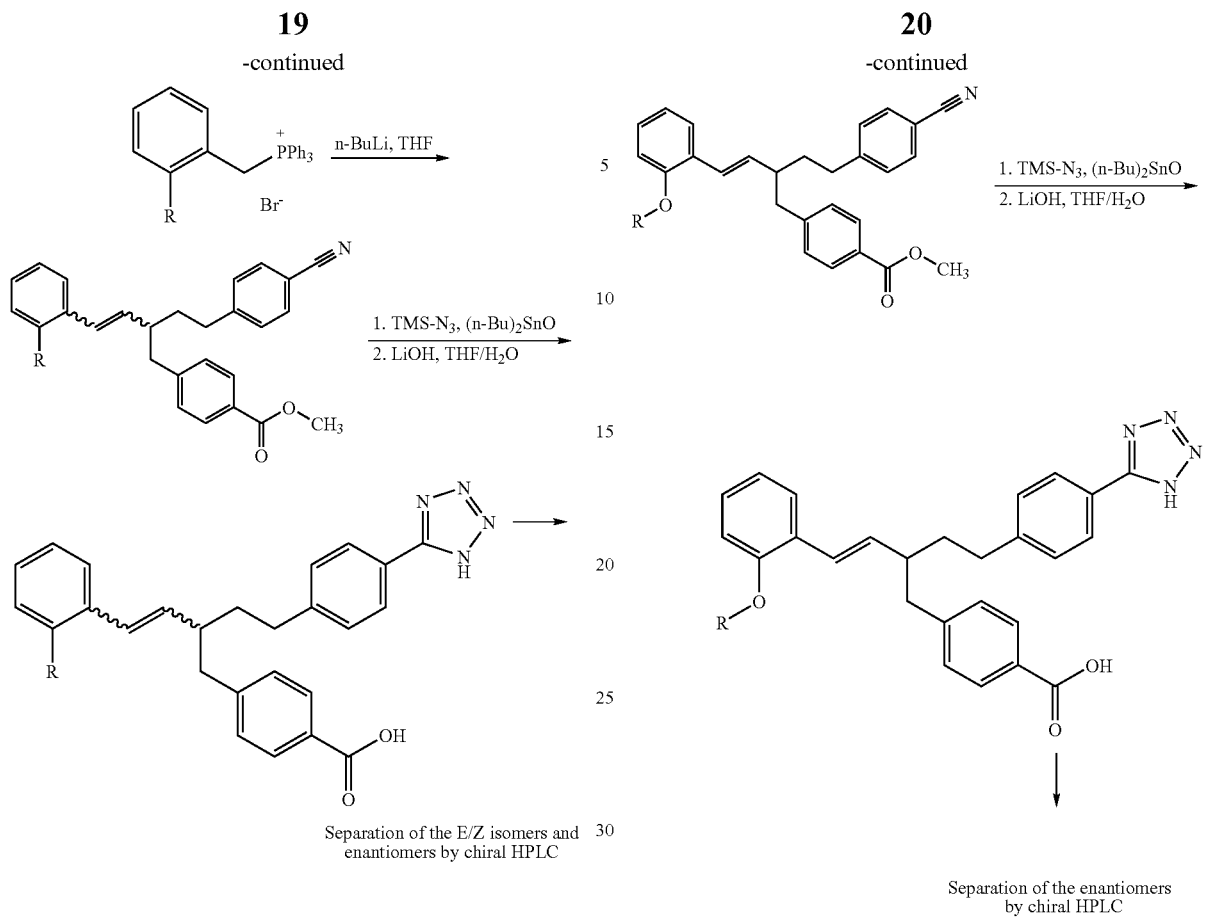
Separation of the E/Z isomers and enantiomers by chiral HPLC
Separation of the enantiomers by chiral HPLC
Scheme 9
Scheme 10
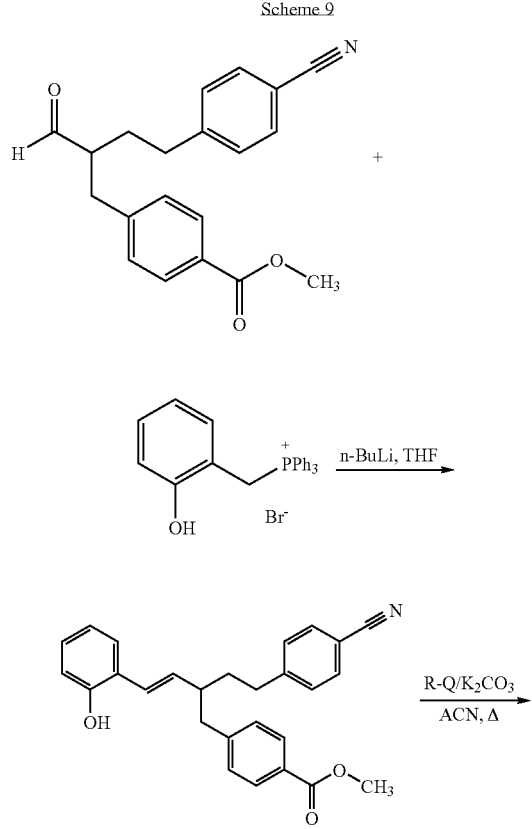

21
-continued
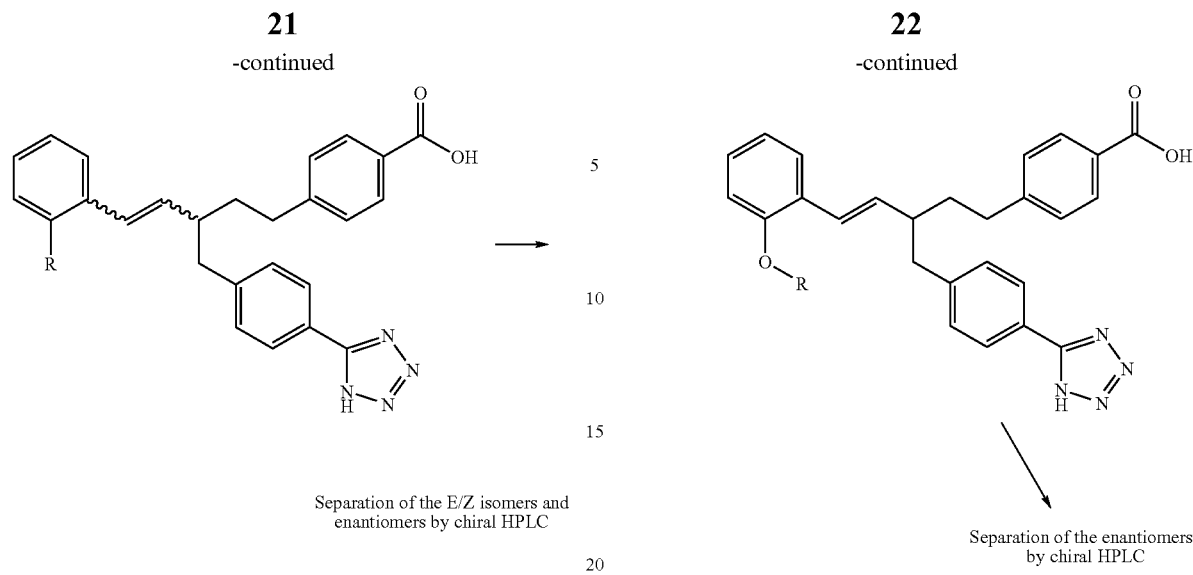
Separation of the E/Z isomers and enantiomers by chiral HPLC
22
-continued
Separation of the enantiomers by chiral HPLC
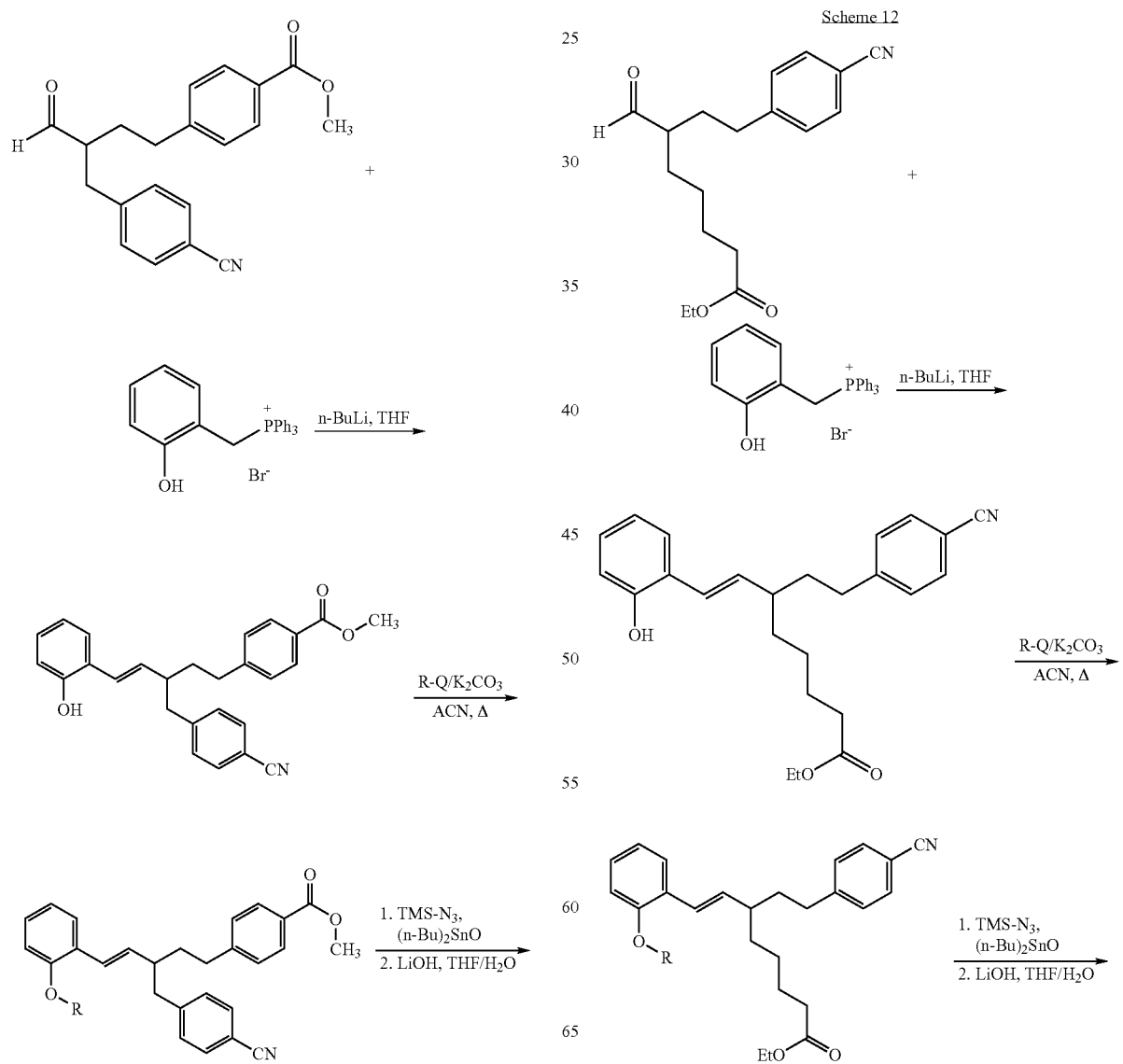

23
-continued
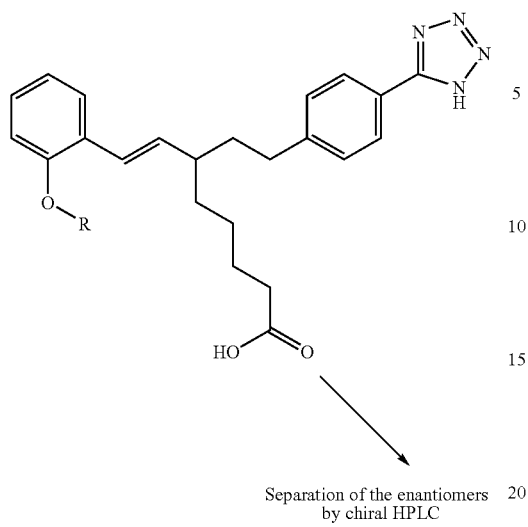
24
-continued
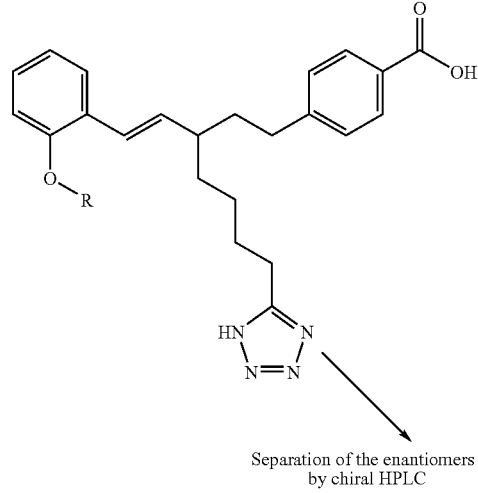
Separation of the enantiomers by chiral HPLC
Separation of the enantiomers by chiral HPLC
Scheme 13
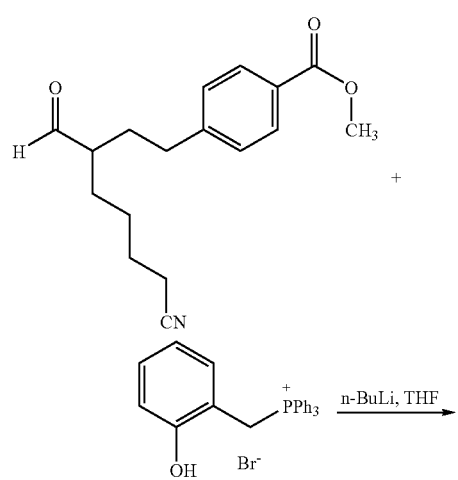
Scheme 14
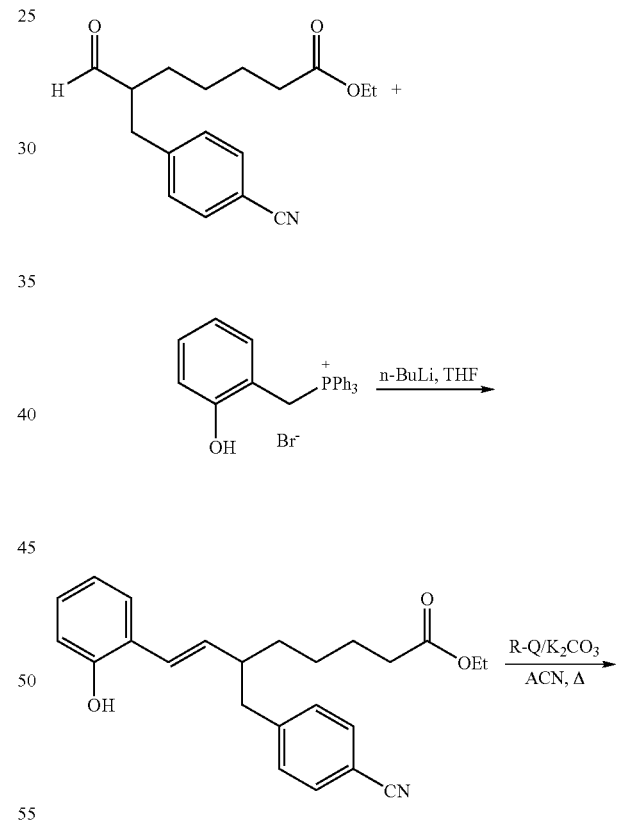
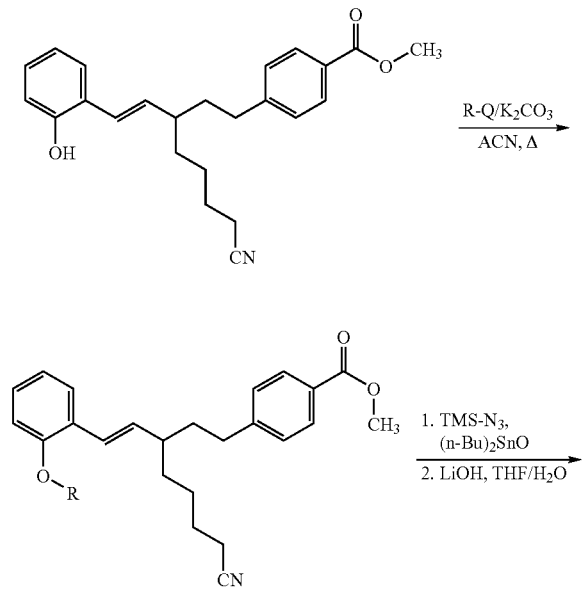
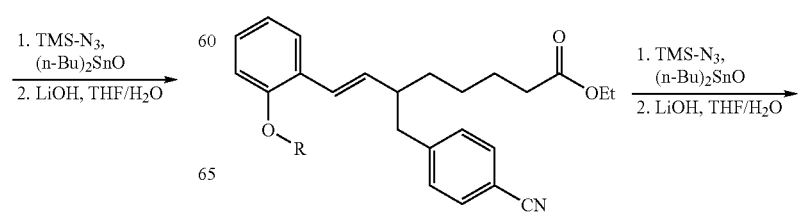

-continued

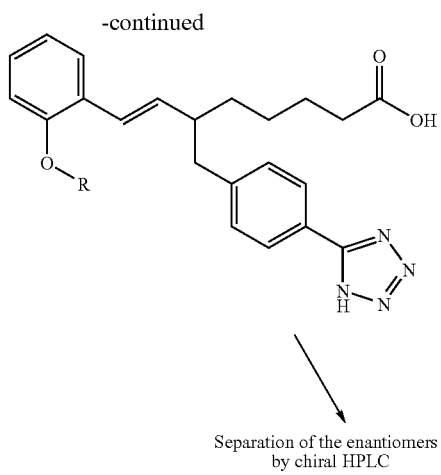

Separation of the enantiomers by chiral HPLC

[Abbreviations: Ac=acetyl; ACN=acetonitrile; (Boc)₂O=di-tert-butyl pyrocarbonate; Bu=butyl; DME=1,2-dimethoxyethane; DMF=dimethylformamide; DMSO=dimethyl sulfoxide; Et=ethyl; cat.=catalyst; Me=methyl; PCC=pyridinium chlorochromate; Ph=phenyl; Q=leaving group, e.g. halogen; THF=tetrahydrofuran; TMS=trimethylsilyl].

The compounds according to the invention have valuable pharmacological properties and can be used for the prevention and treatment of disorders in humans and animals.

The compounds of the present invention exhibit, as particular and surprising feature, advantageous pharmacokinetic properties such as, for example, an increased bioavailability and/or a prolonged duration of action after oral administration.

The compounds according to the invention lead to vasorelaxation, to an inhibition of platelet aggregation and to a reduction in blood pressure, and to an increase in coronary blood flow. These effects are mediated by direct activation of soluble guanylate cyclase and an intracellular increase in cGMP.

The compounds according to the invention can therefore be employed in medicaments for the treatment of cardiovascular disorders such as, for example, for the treatment of high blood pressure and heart failure, stable and unstable angina pectoris, pulmonary hypertension, peripheral and cardiac vascular disorders, arrhythmias, for the treatment of thromboembolic disorders and ischemeias such as myocardial infarction, stroke, transistoric and ischemeic attacks, disturbances of peripheral blood flow, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, CREST syndrome, erythematosis, onychomycosis and rheumatic disorders.

The compounds according to the invention are furthermore suitable for the treatment of respiratory distress syndromes and chronic obstructive airway disorders (COPD), of acute and chronic renal failure and for promoting wound healing.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions such as stroke, cerebral ischemeias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:

organic nitrates and NO donors such as, for example, sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;

NO-independent but heme-dependent stimulators of guanylate cyclase, such as, in particular, the compounds described in WO 00/06568, WO 00/06569, WO 02/42301 and WO 03/095451;

agents having antithrombotic activity, for example and preferably from the group of platelet aggregation inhibitors, of anticoagulants or of profibrinolytic substances;

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, BAY 59-7939, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein(a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, Cholesta-Gel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations
abs. Absolute
aq. Aqueous
CI Chemical ionization (in MS)
DCI Direct chemical ionization (in MS)
DMF Dimethylformamide
DMSO Dimethyl sulfoxide
ee Enantiomeric excess EI Electron impact ionization (in MS)
eq. Equivalent(s)
ESI Electrospray ionization (in MS)
Ex. Example
GC Gas chromatography
h Hour(s)
HPLC High pressure, high performance liquid chromatography
LC/MS Coupled liquid chromatography-mass spectroscopy
Min Minute(s)
MS Mass spectroscopy
NMR Nuclear magnetic resonance spectroscopy
$R_f$ Retention index (in TLC)
RT Room temperature
$R_t$ Retention time (in HPLC)
THF Tetrahydrofuran
TLC Thin-layer chromatography
UV Ultraviolet spectroscopy
v/v Volume to volume ratio (of a solution)

LC/MS Methods:
Method 1 (LC-MS)
MS instrument type: Micromass ZQ; HPLC instrument type: HP 1100 series; UV DAD; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC-MS)
MS instrument type: Micromass ZQ; HPLC instrument type: Waters Alliance 2795; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min 2.5 min/3.0 min/4.5 min 2 ml/min; oven: 50° C.; UV detection: 210 nm.

Method 3 (LC-MS)
Instrument: Micromass Platform LCZ with HPLC Agilent Series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A o 4.5 min 5% A; flow rate: 0.0 min 1 ml/min o 2.5 min/3.0 min/4.5 min 2 ml/min; oven: 50° C.; UV detection: 210 nm.

Method 4 (LC-MS)
Instrument: Micromass Quattro LCZ with HPLC Agilent Series 1100; column: Phenomenex Synergi 21µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min ~2.5 min/3.0 min/4.5 min 2 ml/min; oven: 50° C.; UV detection: 208-400 nm.

Method 5 (LC-MS)
Instrument: Micromass Platform LCZ with HPLC Agilent Series 1100; column: Thermo Hypersil GOLD 3µ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A o 3.1 min 10% A→5.5 min 10% A; oven: 50° C.; flow rate: 0.8 ml/min; UV detection: 210 nm.

Method 6 (LC-MS)
MS instrument type: Micromass ZQ; HPLC instrument type: Waters Alliance 2795; column: Merck Chromolith SpeedROD RP-18e 100 mm×4.6 mm; eluent A: water+500 µl of 50% formic acid/l, eluent B: acetonitrile+500 µl of 50% formic acid/l; gradient: 0.0 min 10% B→7.0 min 95% B→9.0 min 95% B; flow rate: 0.0 min 1.0 ml/min ~7.0 min 2.0 ml/min ~9.0 min 2.0 ml/min; oven: 35° C.; UV detection: 210 nm.

GC/MS Methods:
Method 1 (GC-MS)
Instrument: Micromass GCT, GC6890; column: Restek RTX-35MS, 30 m×250 µm×0.25 µm; constant helium flow: 0.88 ml/min; oven: 60° C.; inlet: 250° C.; gradient: 60° C. (hold for 0.30 min), 50° C./min ~120° C., 16° C./min ~250° C., 30° C./min ~300° C. (hold for 1.7 min).

Method 2 (GC-MS)
Instrument: Micromass GCT, GC6890; column: Restek RTX-35MS, 30 m×250 µm×0.25 µm; constant helium flow: 0.88 ml/min; oven: 60° C.; inlet: 250° C.; gradient: 60° C. (hold for 0.30 min), 50° C./min ~120° C., 16° C./min ~250° C., 30° C./min ~300° C. (hold for 8.7 min).

HPLC Methods:
Method 1 (HPLC)
Instrument: HP 1100 with DAD detection; column: Kromasil 100 RP-18, 60 mm×2.1 mm, 3.5 µm; eluent A: 5 ml of $HClO_4$ (70%)/l of water, eluent B: acetonitrile; gradient: 0 min 2% B→0.5 min 2% B→4.5 min 90% B→9 min 90% B→9.2 min 2% B→10 min 2% B; flow rate: 0.75 ml/min; column temperature: 30° C.; UV detection: 210 nm.

Method 2 (HPLC)
Instrument: HP 1100 with DAD detection; column: Kromasil 100 RP-18, 60 mm×2.1 mm, 3.5 µm; eluent A: 5 ml of $HClO_4$ (70%)/l of water, eluent B: acetonitrile; gradient: 0 min 2% B→0.5 min 2% B→4.5 min 90% B→15 min 90% B→15.2 min 2% B→16 min 2% B; flow rate: 0.75 ml/min; column temperature: 30° C.; UV detection: 210 nm.

Starting Compounds and Intermediates

Example 1A

Example 26A (5-Bromopentyl)benzene

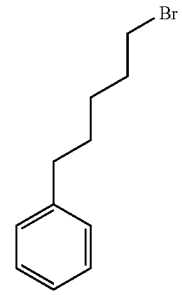

A solution of 416.7 ml (1.83 mol) 48% strength hydrobromic acid is mixed with 50 g (0.304 mol) of 5-phenylpentan-1-ol at 0° C. and stirred at 0° C. for 30 min. The reaction solution is then stirred at 100° C. for 12 hours. After reaction is complete, the mixture is cooled to room temperature and 200 ml of ethyl acetate are added. After extraction, the organic phase is separated off, washed with saturated sodium bicarbonate solution and dried over sodium sulfate. After filtration, the filtrate is is concentrated to dryness. The resulting crude product is purified by flash chromatography on silica gel (mobile phase: cyclohexane). 59.4 g (0.26 mol, 86% of theory) of a colorless liquid are obtained.

$^1$H-NMR (300 MHz, CDCl$_3$, δ/ppm): 7.32-7.22 (2H, m), 7.21-7.11 (3H, m), 3.40 (2H, t), 2.61 (2H, t), 1.97-1.81 (2H, m), 1.72-1.58 (2H, m), 1.56-1.39 (2H, m).

MS (CI): 226 (M$^+$).

Example 2A

[4-(2-Bromoethyl)phenyl]methanol

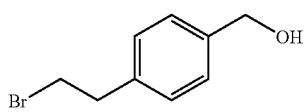

13.1 ml (13.1 mmol) of 1M borane-THF complex are added dropwise to a solution of 2 g (8.73 mmol) of 4-(2-bromoethyl)benzoic acid in 50 ml of dry THF at −10° C. After warming to room temperature, the mixture is stirred for one hour. After the reaction is complete, the mixture is mixed with saturated ammonium chloride solution and taken up in ethyl acetate, the organic phase is separated off and dried over sodium sulfate. After filtration, the solvent is removed in vacuo. 1.67 g (7.76 mmol, 79% of theory) of a colorless oil are obtained and are employed in the next stage without further purification.

$^1$H-NMR (300 MHz, DMSO-d$_6$, δ/ppm): 7.33-7.28 (4H, m), 5.14 (1H, t), 4.48 (2H, d), 3.77 (2H, t), 3.11 (2H, t).

MS (DCI, NH$_3$): 232 (M+NH$_4^+$).

Example 3A 4-(2-Bromoethyl)benzaldehyde

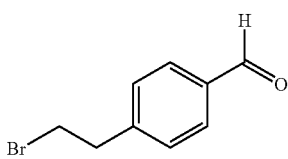

Process 1.

A solution of 200 mg (0.93 mmol) of [4-(2-bromoethyl)phenyl]methanol in 20 ml of dichloromethane is mixed with 240.5 mg (1.12 mmol) of pyridinium chlorochromate (PCC) and stirred at room temperature for 3 hours. The reaction solution is then mixed with about 2 g of silica gel and concentrated to dryness. The residue is purified by flash chromatography on silica gel (mobile phase: cyclohexane/ethyl acetate 4:1). 183 mg (0.85 mmol, 82% of theory) of a colorless solid are obtained.

Process 2:

42.26 ml of titanium tetrachloride are added over the course of 10 min to a solution of 44.4 g (0.38 mol) of dichloromethyl methyl ether in 230 ml of dichloromethane while cooling (4-5° C.), and the mixture is stirred for 1 hour. Then 64.89 g (0.34 mol) of 2-bromoethylbenzene, dissolved in 24 ml of dichloromethane, are metered into the reaction solution over the course of 50 min at 5-7° C. The reaction solution is then warmed slowly to room temperature and the mixture is stirred overnight. After reaction is complete, 140 ml of water are very cautiously added dropwise over the course of 1 hour (caution: initially endothermic reaction through evolution of gas, then exothermic reaction up to 30° C., cooling necessary). The reaction solution is then extracted three times with dichloromethane, and the combined organic phases are washed with 170 ml of water, neutralized with 115 ml of sodium bicarbonate solution and dried over sodium sulfate. After filtration, the solvent is removed in vacuo. The resulting residue is purified by flash chromatography on silica gel (mobile phase: dichloromethane/petroleum ether 1:2→1:1). 29.3 g (0.14 mol, 37% of theory) of a colorless solid are obtained.

$^1$H-NMR (300 MHz, DMSO-d$_6$, δ/ppm): 9.99 (1H, s), 7.88 (2H, d), 7.52 (2H, d), 3.80 (2H, t), 3.24 (2H, t).

MS (EI): 212 (M$^+$).

Example 4A 4-(2-Bromoethyl)benzonitrile

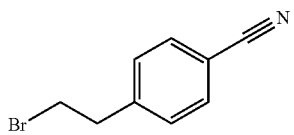

A solution of 29.3 g (0.14 mol) of 4-(2-bromoethyl)benzaldehyde in 112.4 ml of formic acid is mixed with 12.42 g (0.18 mol) of hydroxylamine hydrochloride and heated under reflux for 2 hours. After slow cooling to room temperature, 670 ml of water are added, and the reaction mixture is slowly neutralized with 6 N sodium hydroxide solution while cooling. The mixture is then extracted three times with methyl tert-butyl ether. The combined organic phases are dried over magnesium sulfate and concentrated. The resulting residue is purified by flash chromatography on silica gel (mobile phase: dichloromethane). 21.3 g (0.10 mol, 74% of theory) of a yellowish solid are obtained.

$^1$H-NMR (400 MHz, DMSO-d$_6$, δ/ppm): 7.80 (2H, d), 7.51 (2H, d), 3.77 (2H, t), 3.22 (2H, t).

MS (DCI, NH$_3$): 227 (M+NH$_4^+$).

Example 5A

Diallyl 2-(4-methoxycarbonylbenzyl)malonate

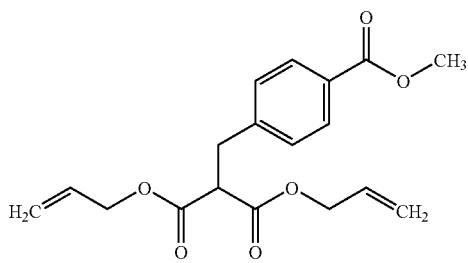

14.42 g (0.36 mol) of sodium hydride are added in portions to a solution of 56.7 g (0.3 mol) of diallyl malonate in 375 ml of dioxane and 75 ml of THF at 0° C. (caution: evolution of hydrogen). After warming to room temperature, the mixture is stirred at 40° C. for 1 hour. Subsequently, 111.88 g (0.6 mol) of methyl 4-chloromethylbenzoate, dissolved in 375 ml of dioxane, are slowly added dropwise at 40° C., and the reaction solution is stirred at 110° C. overnight. After cooling to room temperature, the reaction mixture is added to 1200 ml of water. Care must be taken during this that the pH is <7 (where appropriate, a few ml of 1 M hydrochloric acid are metered in to about pH 2). The mixture is then extracted three times with ethyl acetate, and the combined organic phases are washed with saturated sodium chloride solution and dried over sodium sulfate. After filtration, the solvent is concentrated to dryness in vacuo. The resulting crude product is purified by flash chromatography (mobile phase: petroleum ether/ethyl acetate 10:1; 3 kg of silica gel). 85.4 g (0.26 mol, 85% of theory) of a colorless solid are obtained.

$^1$H-NMR (300 MHz, CDCl$_3$, δ/ppm): 7.96 (2H, d), 7.29 (2H, d), 5.91-5.74 (2H, m), 5.32-5.17 (4H, m), 4.59 (4H, d), 3.93 (3H, s), 3.74 (1H, t), 3.31 (2H, d).

MS (DCI): 349 (M+NH$_4^+$).

Example 6A

Diallyl 2-[2-(4-cyanophenyl)ethyl]-2-(4-methoxycarbonylbenzyl)malonate

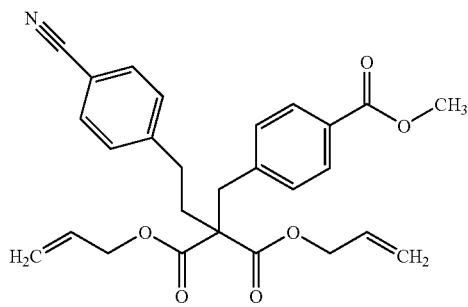

6.70 g (0.17 mol) of sodium hydride are added in portions to a solution of 55.71 g (0.17 mol) of diallyl 2-(4-methoxycarbonylbenzyl)malonate in 34 ml of DMF at 0° C. The reaction solution is then allowed to reach room temperature and is stirred for 1 hour. The reaction solution is then cooled to 0° C. again, 42.98 g (0.20 mol) of 4-(2-bromoethyl)benzonitrile in 21 ml of DMF are added, and the mixture is stirred at this temperature for 30 min. The mixture is then stirred at room temperature overnight. Water is added dropwise to the reaction mixture, which is then extracted three times with ethyl acetate, and the combined organic phases are washed with saturated sodium chloride solution and dried over sodium sulfate. After filtration, the solvent is concentrated to dryness in vacuo. The resulting crude product is purified by flash chromatography (mobile phase: petroleum ether/ethyl acetate 3:1; 3 kg of silica gel). 36 g (78 mmol, 46% of theory) of a colorless solid are obtained.

$^1$H-NMR (300 MHz, CDCl$_3$, δ/ppm): 7.95 (2H, d), 7.55 (2H, d), 7.21 (4H, t), 5.97-5.69 (2H, m), 5.40-5.23 (4H, m), 4.62 (4H, d), 3.92 (3H, s), 3.40 (2H, s), 2.72-2.61 (2H, m), 2.13-2.01 (2H, m).

MS (DCI): 479 (M+NH$_4^+$).

Example 7A

Methyl 4-[2-carboxy-4-(4-cyanophenyl)butyl]benzoate

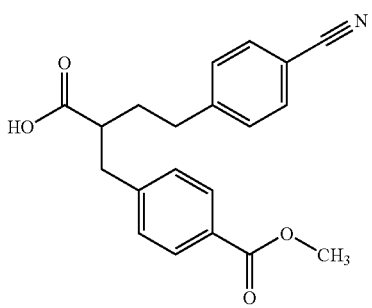

A solution of 41.8 ml (0.3 mol) of triethylamine and 8.6 ml (0.23 mol) of formic acid in 500 ml of dioxane is added to a solution of 43.5 g (0.09 mol) of diallyl 2-[2-(4-cyanophenyl)ethyl]-2-(4-methoxycarbonylbenzyl)malonate, 1.67 g (0.01 mol) of triphenylphosphine and 410 mg of palladium acetate in 505 ml of dioxane at room temperature. The reaction mixture is then stirred at 100° C. for 2 hours. After conversion is complete, the reaction solution is cooled and the solvent is removed in vacuo. The resulting residue is purified by flash chromatography on silica gel (mobile phase: dichloromethane/methanol 50:1). 25 g (74 mmol, 82% of theory) of a colorless solid are obtained.

$^1$H-NMR (400 MHz, DMSO-d$_6$, δ/ppm): 12.55-12.24 (1H, broad), 7.86 (2H, d), 7.72 (2H, d), 7.38 (2H, d), 7.32 (2H, d), 3.84 (3H, s), 2.99-2.81 (2H, m), 2.78-2.55 (3H, m), 1.90-1.67 (2H, m).

MS (ESI): 338 (M+H$^+$).

Example 8A

Methyl 4-[4-(4-cyanophenyl)-2-hydroxymethylbutyl]benzoate

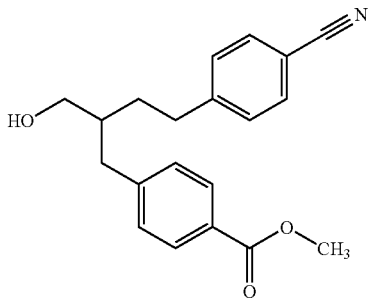

26 ml (26 mmol) of a 1 M borane-THF complex solution are added dropwise to a solution of 4.2 g (12.98 mmol) of methyl 4-[2-carboxy-4-(4-cyanophenyl)butyl]benzoate in 40 ml of THF at −15° C., and the mixture is stirred at this temperature for 3 h. A further 13 ml (13 mmol) of 1 M borane-THF complex solution is then added dropwise and stirring is continued for a further 30 min at −15° C. After reaction is complete, saturated sodium bicarbonate solution is added to the reaction mixture, and the solvent is concentrated to dryness. The residue is taken up in dichloromethane, dried over sodium sulfate and again freed of solvent. The resulting crude product is purified by flash chromatography (mobile phase: ethyl acetate/petroleum ether 1:1, 150 g silica gel). 3.1 g (90% purity, 83% of theory) of a colorless solid are obtained.

$^1$H-NMR (300 MHz, DMSO-$d_6$, δ/ppm): 7.88 (2H, d), 7.71 (2H, d), 7.46 (4H, t), 4.54 (1H, t), 3.83 (3H, s), 3.41 (2H, t), 2.80-2.55 (4H, m), 1.79-1.39 (3H, m).

MS (ESI): 324 (M+H$^+$).

Example 9A

Methyl 4-[4-(4-cyanophenyl)-2-formylbutyl]benzoate

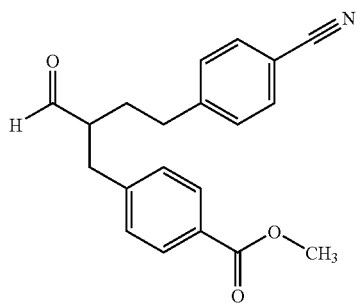

A solution of 5.7 g (17.63 mmol) of methyl 4-[4-(4-cyanophenyl)-2-hydroxymethylbutyl]benzoate in 250 ml of dichloromethane is mixed with 4.56 g (21.15 mmol) of pyridinium chlorochromate (PCC) and stirred at room temperature for 5 hours. After conversion is complete, about 10 g of silica gel are added, and the solvent is removed to dryness in vacuo. The residue is purified by flash chromatography on silica gel (mobile phase: cyclohexane/ethyl acetate 10:1→4:1). 4.16 g (12.94 mmol, 73% of theory) of a colorless solid are obtained.

$^1$H-NMR (300 MHz, DMSO-$d_6$, δ/ppm): 9.68 (1H, s), 7.88 (2H, d), 7.73 (2H, d), 7.47 (4H, dd), 3.86 (3H, s), 3.14-3.02 (1H, m), 2.92-2.80 (1H, m), 2.78-2.54 (3H, m), 1.98-1.81 (1H, m), 1.76-1.60 (1H, m).

MS (DCI): 339 (M+NH$_4^+$).

Example 10A

Methyl E-4-[2-[2-(4-cyanophenyl)ethyl]-4-(2-hydroxyphenyl)but-3-enyl]benzoate

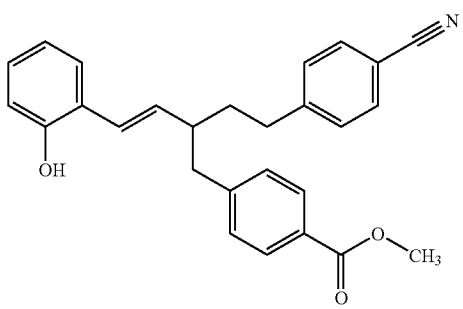

5.9 ml (9.45 mmol) of a 1.6 M solution of n-butyllithium in hexane are slowly added to a solution of 1820 mg (4.05 mmol) of (2-hydroxybenzyl)triphenylphosphonium bromide in 50 ml of anhydrous THF at 0° C. Then, at this temperature, 1085 mg (3.38 mmol) of methyl 4-[4-(4-cyanophenyl)-2-formylbutyl]benzoate, dissolved in 40 ml of THF, are added slowly. After warming to room temperature, the reaction solution is stirred for 12 hours and then, after addition of some water, concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 4:1→2:1). 1150 mg (2.79 mmol, 83% of theory) of a colorless solid are obtained.

$^1$H-NMR (300 MHz, DMSO-$d_6$, δ/ppm): 9.39 (1H, s), 7.82 (2H, d), 7.60 (2H, d), 7.41-7.27 (5H, m), 7.01 (1H, t), 6.81-6.68 (2H, m), 6.45 (1H, d), 6.13-5.99 (1H, m), 3.81 (3H, s), 2.92-2.58 (5H, m), 1.86-1.56 (2H, m).

MS (DCI): 429 (M+NH$_4^+$).

Example 11A 4-tert-Butyl-2-chloro-1-methylbenzene

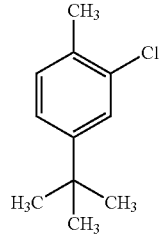

A solution of 2 g (13.49 mmol) of 4-tert-butyltoluene is mixed with 5.65 g (13.49 mmol) of benzyltrimethylammonium tetrachloroiodate and stirred at 70° C. for 24 hours. After cooling, the precipitate is filtered off with suction and the filtrate is concentrated. The resulting residue is purified over silica gel (mobile phase: cyclohexane). 1.53 g (8.4 mmol) of the title compound are obtained.

GC-MS (method 1): R$_f$=5.27 min

MS (ESI): m/z=182 (M)$^+$.

Example 12A

2-Chloro-4-(tert-butyl)benzyl bromide

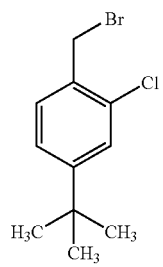

1.75 g (9.85 mmol) of N-bromosuccinimide and 10.8 mg (0.006 mmol) of 2,2'-azobis-2-methylpropanenitrile are added to a solution of 2 g (10.95 mmol) of 4-tert-butyl-2-chloro-1-methylbenzene in 10 ml of tetrachloromethane, and the mixtures is stirred under reflux for 4 hours. After cooling, the mixture is concentrated. The residue is purified by flash chromatography on silica gel (mobile phase, cyclohexane). 2.1 g (38% of theory) of the title compound are obtained with a purity of 52%.

GC-MS (method 1): R$_f$=8.13 min

MS (EI): m/z=262 (M+H)$^+$.

Example 13A

Methyl 4-{(3E)-4-{2-[(4-tert-butyl-2-chlorobenzyl)oxy]phenyl}-2-[2-(4-cyanophenyl)ethyl]but-3-en-1-yl}benzoate

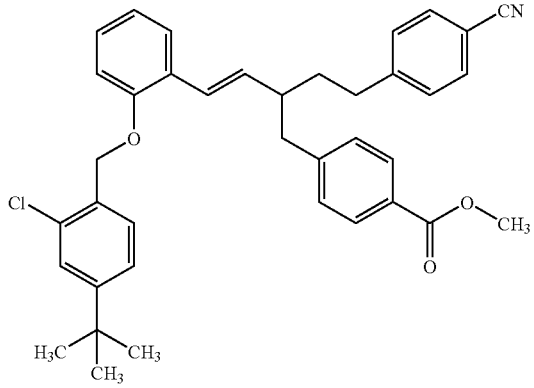

A solution of 450 mg (1.09 mmol) of methyl 4-[(3E)-2-[2-(4-cyanophenyl)ethyl]-4-(2-hydroxyphenyl)but-3-en-1-yl]benzoate in 10 ml of dry acetonitrile is mixed with 825.2 mg (1.64 mmol) of 2-chloro-4-(tert-butyl)benzyl bromide and 453.4 mg (3.28 mmol) of anhydrous potassium carbonate and heated under reflux for 12 h. The mixture is then concentrated to dryness. The residue is taken up in ethyl acetate, washed with water and saturated sodium chloride solution and dried over sodium sulfate. The organic phase is concentrated. The resulting crude product is purified by preparative HPLC. 518 mg (0.87 mmol, 73.9% of theory) of a colorless foam are obtained.

$^1$H-NMR (400 MHz, CDCl$_3$, δ/ppm): 7.91 (2H, d), 7.47 (2H, d), 7.43-7.34 (3H, m), 7.29-7.23 (1H, m), 7.23-7.14 (5H, m), 7.0-6.9 (2H, m), 6.67 (1H, d), 5.99 (1H, dd), 5.18-5.08 (2H, m), 3.88 (3H, s), 2.85-2.71 (3H, m), 2.66-2.54 (1H, m), 2.54-2.42 (1H, m), 1.85-1.75 (1H, m), 1.71-1.59 (1H, m), 1.31 (9H, s).

LC-MS (method 2): R$_t$=3.46 min.
MS (ESIpos): m/z=592 (M+H)$^+$.

Example 14A

Methyl 4-((3E)-4-{2-[(4-tert-butyl-2-chlorobenzyl)oxy]phenyl}-2-{2-[4-(1H-tetrazol-5-yl)phenyl]ethyl}but-3-en-1-yl)benzoate

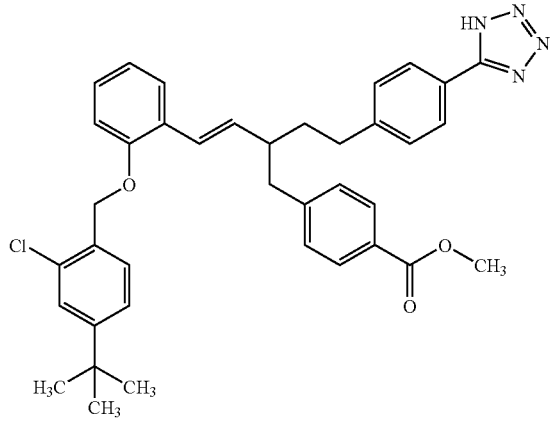

A solution of 478 mg (0.81 mmol) of methyl 4-{(3E)-4-{2-[(4-tert-butyl-2-chlorobenzyl)oxy]-phenyl}-2-[2-(4-cyanophenyl)ethyl]but-3-en-1-yl}benzoate in 10 ml of toluene is mixed with 1116 mg (9.69 mmol) of trimethylsilyl azide and 351 mg (1.21 mmol) of di-n-butyltin oxide and then heated at 80° C. for 12 h. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by chromatography on a silica gel column (mobile phase: cyclohexane/ethyl acetate 2:1→1:2). 144 mg (0.23 mmol, 28% of theory) of a white foam are obtained.

$^1$H-NMR (300 MHz, DMSO-d$_6$, δ/ppm): 7.9 (2H, d), 7.81 (2H, d), 7.48-7.24 (8H, m), 7.24-7.14 (1H, m), 7.06 (1H, m), 6.92 (1H, t), 6.48 (1H, d), 6.11 (1H, dd), 5.1 (2H, s), 3.79 (3H, s), 2.93-2.82 (1H, m), 2.80-2.57 (3H, m), 1.88-1.74 (1H, m), 1.74-1.57 (2H, m).

LC-MS (method 2): R$_t$=3.28 min.
MS (ESIpos): m/z=635 (M+H)$^+$.

Example 15A

Methyl 4-{(3E)-4-{2-[(4-tert-butylbenzyl)oxy]phenyl}-2-[2-(4-cyanophenyl)ethyl]but-3-en-1-yl}-benzoate

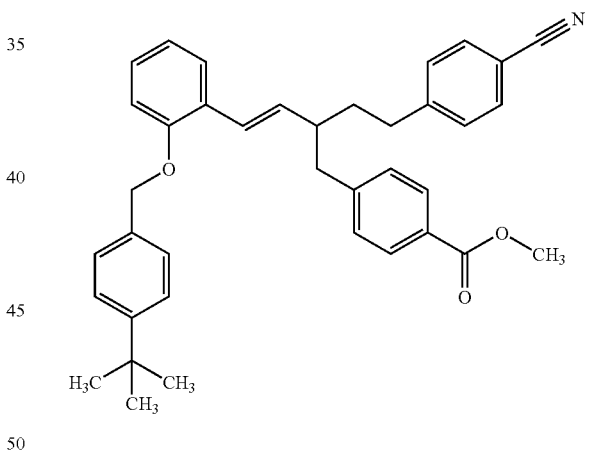

A solution of 2 g (3.6 mmol) of methyl E-4-[2-(4-cyanophenyl)ethyl]-4-(2-hydroxyphenyl)but-3-enyl]benzoate (example 17A) in 8 ml of dry acetonitrile is mixed with 2.20 g (9.71 mmol) of 4-(tert-butyl)benzyl bromide and 2.02 g (14.59 mmol) of anhydrous potassium carbonate and heated under reflux for 12 hours. The mixture is then filtered, and the filtrate is concentrated to dryness. The residue is purified by chromatography on silica gel (mobile phase: cyclohexane/ethyl acetate 10:1). 1.9 g (3.30 mmol, 97% purity, 92% of theory) of an oil are isolated.

$^1$H-NMR (400 MHz, CDCl$_3$, δ/ppm): 7.94-7.89 (2H, m), 7.49-7.30 (7H, m), 7.21-7.12 (5H, m), 6.97-6.90 (2H, m), 6.68-7.62 (1H, m), 5.06-5.02 (2H, m), 3.89 (3H, s), 2.83-2.69 (3H, m), 2.65-2.39 (2H, m), 1.86-1.59 (2H, m), 1.33 (9H, s).

LC-MS (method 2): R$_t$ 3.37 min; m/z 575 (M+NH$_4^+$), 557 (M$^+$).

Example 16A

Methyl 4-((3E)-4-{2-[(4-tert-butylbenzyl)oxy]phenyl}-2-{2-[4-(1H-tetrazol-5-yl)phenyl]ethyl}-but-3-en-1-yl)benzoate

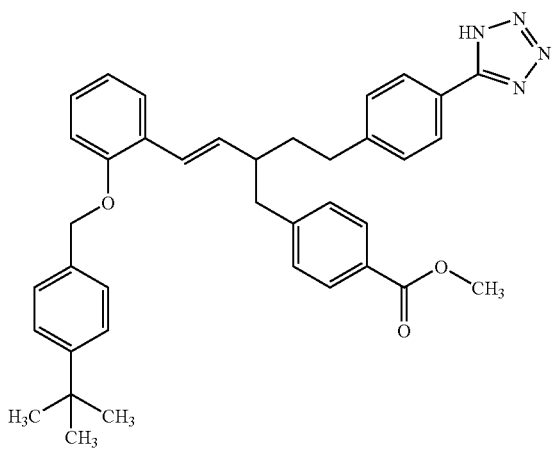

A solution of 1000 mg (1.79 mmol) of methyl 4-{(3E)-4-{2-[(4-tert-butylbenzyl)oxy]phenyl}-2-[2-(4-cyanophenyl)ethyl]but-3-en-1-yl}benzoate in 10 ml of toluene is mixed with 2851 mg (24.7 mmol) of trimethylsilyl azide and 618 mg (2.47 mmol) of di-n-butyltin oxide and heated at 80° C. for 12 h. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by chromatography on a silica gel column (mobile phase: cyclohexane/ethyl acetate 2:1→1:2). 648 mg (1.08 mmol, 60% of theory) of a colorless oil are obtained.

$^1$H-NMR (400 MHz, DMSO-d$_6$, δ/ppm): 16.75 (1H, broad), 7.92 (2H, d), 7.83 (2H, d), 7.42-7.25 (9H, m), 7.18 (1H, t), 7.04 (1H, d), 6.9 (1H, t), 6.5 (1H, d), 6.12 (1H, dd), 5.05 (2H, s), 3.8 (3H, s), 2.93-2.86 (1H, m), 2.8-2.7 (2H, m), 2.69-2.59 (1H, m), 1.89-1.78 (1H, m), 1.75-1.58 (2H, m), 1.22 (9H, s).

Example 17A

Methyl 4-{(3E)-4-{2-[(2-chlorobenzyl)oxy]phenyl}-2-[2-(4-cyanophenyl)ethyl]but-3-en-1-yl}-benzoate

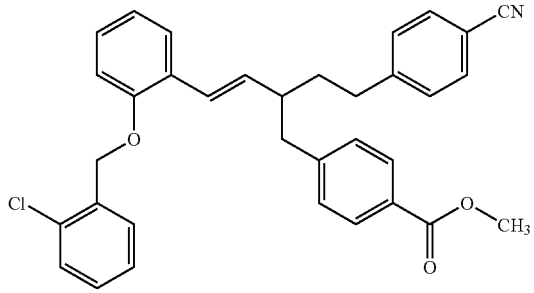

A solution of 200 mg (0.49 mmol) of methyl 4-[(3E)-2-[2-(4-cyanophenyl)ethyl]-4-(2-hydroxyphenyl)but-3-en-1-yl]benzoate in 10 ml of dry acetonitrile is mixed with 149.8 mg (0.73 mmol) of 2-chlorobenzyl bromide and 201 mg (1.46 mmol) of anhydrous potassium carbonate and heated under reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by preparative HPLC. 94 mg (0.17 mmol, 36% of theory) of a colorless foam are obtained.

LC-MS (method 2): R$_t$=3.28 min.
MS (ESIpos): m/z=536 [M+H$^+$].

Example 18A

Methyl 4-((3E)-4-{2-[(2-chlorobenzyl)oxy]phenyl}-2-{2-[4-(1H-tetrazol-5-yl)phenyl]ethyl}but-3-en-1-yl)benzoate

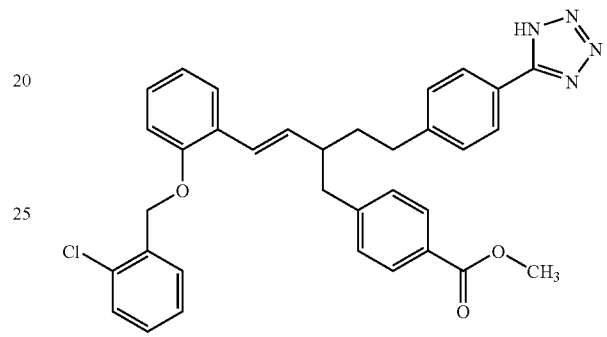

A solution of 94 mg (0.18 mmol) of methyl 4-{(3E)-4-{2-[2-chlorobenzyl)oxy]phenyl}-2-[2-(4-cyanophenyl)ethyl]but-3-en-1-yl}benzoate in 2 ml of toluene is mixed with 303 mg (2.63 mmol) of trimethylsilyl azide and 65.7 mg (0.26 mmol) of di-n-butyltin oxide and heated at 80° C. for 12 h. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by chromatography on a silica gel column (mobile phase: cyclohexane/ethyl acetate 1:1). 95 mg (0.16 mmol, 78.4% of theory) of a colorless foam are obtained.

$^1$H-NMR (300 MHz, CDCl$_3$, δ/ppm): 7.83 (2H, d), 7.79 (2H, d), 7.52-7.38 (4H, m), 7.24-7.1 (6H, m), 7.0-6.9 (2H, m), 6.71 (1H, d), 5.06 (1H, dd), 5.18 (2H, s), 3.92 (3H, s), 2.87-2.51 (5H, m), 2.5-2.35 (1H, m).

Example 19A

Methyl 4-[(3E)-2-[2-(4-cyanophenyl)ethyl]-4-(2-{[2-(trifluoromethyl)benzyl]oxy}phenyl)but-3-en-1-yl]benzoate

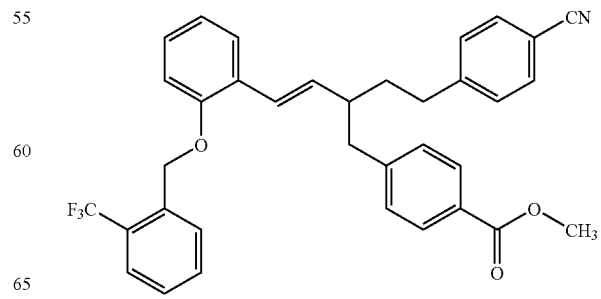

A solution of 438 mg (1.02 mmol) of methyl 4-[(3E)-2-[2-(4-cyanophenyl)ethyl]-4-(2-hydroxyphenyl)but-3-en-1-yl]benzoate in 20 ml of dry acetonitrile is mixed with 382 mg (1.6 mmol) of 2-trifluoromethylbenzyl bromide and 441.3 mg (3.19 mmol) of anhydrous potassium carbonate and heated under reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by preparative HPLC. 181 mg (0.32 mmol, 31.3% of theory) of a colorless foam are obtained.

$^1$H-NMR (300 MHz, CDCl$_3$, δ/ppm): 7.91 (2H, d), 7.71 (1H, d), 7.62 (1H, d), 7.53 (1H, t), 7.47 (3H, d), 7.4 (1H, d), 7.22-7.15 (5H, m), 6.98 (1H, t), 6.88 (1H, d), 6.66 (1H, d), 6.0 (1H, dd), 5.28 (2H, s), 3.88 (3H, s), 2.82-2.71 (3H, m), 2.68-2.42 (2H, m), 1.89-1.72 (1H, m), 1.72-1.62 (1H, m).

Example 20A

Methyl 4-[(3E)-2-{2-[4-(1H-tetrazol-5-yl)phenyl]ethyl}-4-(2-{[2-(trifluoromethyl)benzyl]oxy}-phenyl)but-3-en-1-yl)benzoate

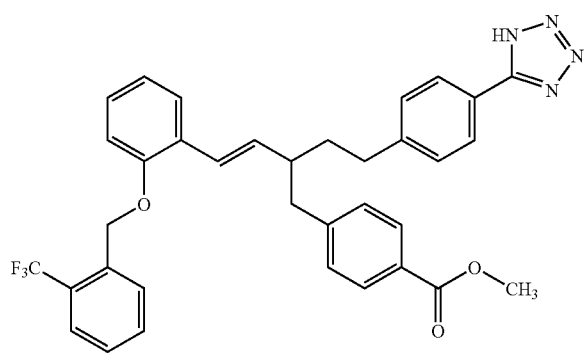

A solution of 212 mg (0.26 mmol) of methyl 4-[(3E)-2-[2-(4-cyanophenyl)ethyl]-4-(2-{[2-(trifluoromethyl)benzyl]oxy}phenyl)but-3-en-1-yl)benzoate in 3 ml of toluene is mixed with 450 mg (3.91 mmol) of trimethylsilyl azide and 97.3 mg (0.39 mmol) of di-n-butyltin oxide and heated at 80° C. for 12 hours. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by chromatography on a silica gel column (mobile phase: cyclohexane/ethyl acetate 1:1). 120 mg (0.19 mmol, 75% of theory) of a colorless foam are obtained.

LC-MS (method 1): R$_f$=3.23 min.

MS (ESIpos): m/z=613 (M+H)$^+$.

Example 21A

[2-(5-Phenylpentyloxy)phenyl]methanol

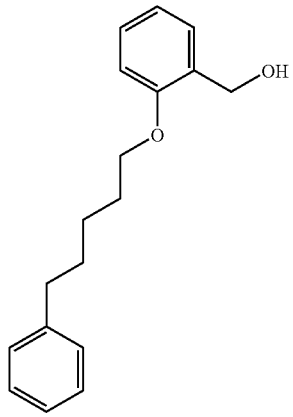

A solution of 10 g (80.56 mmol) of 2-hydroxybenzyl alcohol in 200 ml of dry acetonitrile is mixed with 27.45 g (120.83 mmol) of (5-bromopentyl)benzene and 12.25 g (88.61 mmol) of anhydrous potassium carbonate and heated under reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by flash chromatography on silica gel (mobile phase: cyclohexane/ethyl acetate 10:1). 18.7 g (81% of theory) of a colorless solid are obtained.

$^1$H-NMR (300 MHz, DMSO-d$_6$, δ/ppm): 7.38 (1H, d), 7.31-7.10 (6H, m), 6.91 (2H, t), 4.92 (1H, t), 4.50 (2H, d), 3.95 (2H, t), 2.59 (2H, t), 1.81-1.68 (2H, m), 1.67-1.55 (2H, m), 1.52-1.36 (2H, m).

MS (CI): 288 (M+NH$_4^+$), 270 (M$^+$).

Example 22A

Triphenyl[2-(5-phenylpentyloxy)benzyl]phosphonium bromide

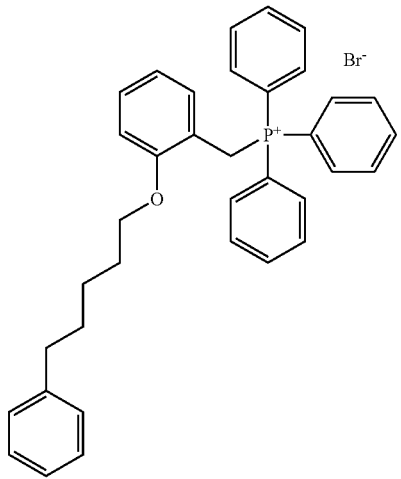

A solution of 18.7 g (69.16 mmol) of [2-(5-phenylpentyloxy)phenyl]methanol in 120 ml of acetonitrile is mixed with 22.55 g (65.71 mmol) of triphenylphosphonium bromide and heated under reflux for 3 hours. The reaction solution is then concentrated to dryness. 36.6 g (61.45 mmol, 83% of theory) of crystalline product are obtained and are reacted without further purification.

$^1$H-NMR (400 MHz, DMSO-$d_6$, δ/ppm): 7.89 (3H, t), 7.78-7.66 (6H, m), 7.64-7.52 (6H, m), 7.32-7.24 (3H, m), 7.21-7.12 (3H, m), 7.01 (1H, d), 6.89-6.77 (2H, m), 4.90 (2H, d), 3.44 (2H, t), 2.56 (2H, t), 1.59-1.46 (2H, m), 1.38-1.25 (2H, m), 1.23-1.12 (2H, m).

MS (ESI): 515 (M$^+$–Br).

Example 23A

Methyl 4-((3E/Z)-2-[2-(4-cyanophenyl)ethyl]-4-{2-[(5-phenylpentyl)oxy]phenyl}but-3-en-1-yl)benzoate

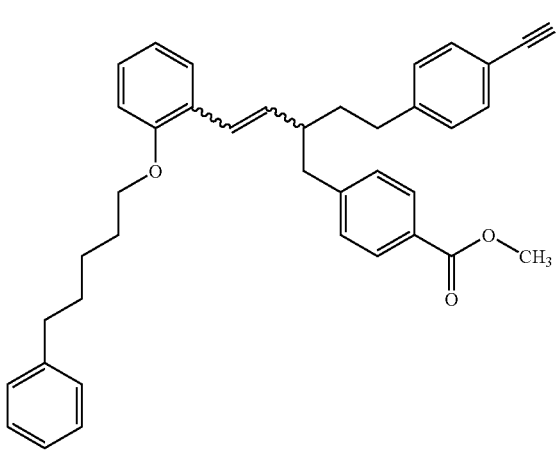

2.36 ml (3.78 mmol) of a 1.6 M solution of n-butyllithium in hexane are slowly added to a solution of 1.8 g (3.02 mmol) of triphenyl {2-[(5-phenylpentyl)oxy]benzyl}phosphonium bromide in 30 ml of THF at 0° C. Then, at this temperature, 810 mg (2.52 mmol) of methyl 4-[4-(4-cyanophenyl)-2-formylbutyl]benzoate in 10 ml of THF are rapidly metered in and the mixture is stirred at 0° C. for 1 h. After warming to room temperature, the reaction solution is stirred for a further 3 h and then mixed with ammonium chloride solution and concentrated to dryness. The residue is taken up in ethyl acetate, washed with water and saturated sodium chloride solution and dried over sodium sulfate. After filtration, the solvent is concentrated to dryness. The resulting crude product is purified by flash chromatography (mobile phase: cyclohexane/ethyl acetate 10:1). 1.27 g (2.28 mmol, 90% of theory) of the title compound are obtained in the form of a solid foam.

$^1$H-NMR (300 MHz, CDCl$_3$, δ/ppm): (E/Z=3.6:1) 7.9 (1.6H, d), 7.8 (0.36H, d), 7.52 (1.6H, d), 7.44 (0.36H, d), 7.37-7.31 (1H, m), 7.31-7.02 (9H, m), 6.99-6.62 (3H, m), 6.54 (1H, d), 6.01-5.89 (1.6H, m), 5.45-5.36 (0.36H, m), 4.0-3.91 (2H, t), 3.9 (3H, s), 2.88-2.7 (3H, m), 2.7-2.55 (4H, m), 2.54-3.39 (1H, m), 1.9-1.6 (7H, m), 1.59-1.45 (2H, m).

MS (DCI): m/z=575 (M+NH$_4$)$^+$.

Example 24A

Methyl 4-((3 E/Z)-4-{2-[(5-phenylpentyl)oxy]phenyl}-2-{2-[4-(1H-tetrazol-5-yl)phenyl]ethyl}but-3-en-1-yl)benzoate

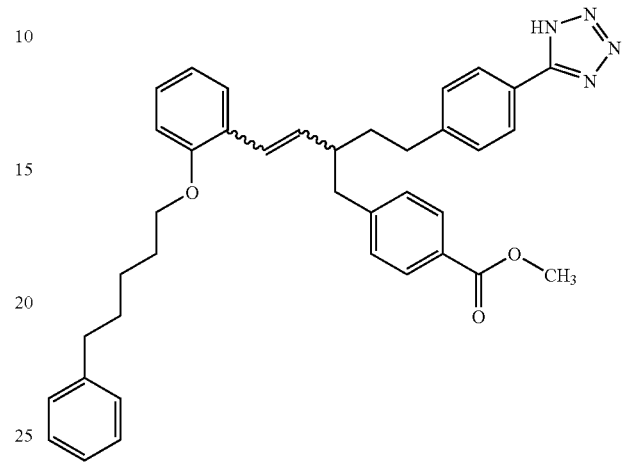

A solution of 160 mg (0.287 mmol) of methyl 4-((3E/Z)-2-[2-(4-cyanophenyl)ethyl]-4-{2-[(5-phenylpentyl)oxy]phenyl}but-3-en-1-yl)benzoate in 5 ml of toluene is mixed with 0.57 ml (4.3 mmol) of trimethylsilyl azide and 107 mg (0.43 mmol) of di-n-butyltin oxide and heated at 80° C. for 12 hours. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by flash chromatography on silica gel (mobile phase: dichloromethane e dichloromethane/methanol 10:1). 138 mg (0.23 mmol, 73.6% of theory) of a colorless oil are obtained.

LC-MS (method 4): R$_t$=3.37 min.

MS (ESIpos): m/z=601 (M+H)$^+$.

Example 25A

Diallyl 2-(4-cyanobenzyl)malonate

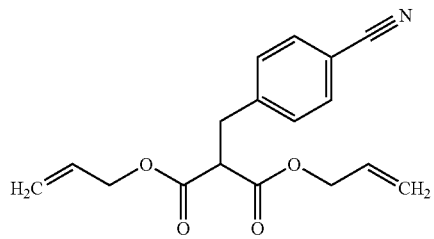

19.79 g (494 mmol) of sodium hydride are added in portions (caution: evolution of hydrogen) to a solution of 121.5 g (659 mmol) of diallyl malonate in 1.5 liters of dioxane at 0° C. The mixture is warmed to room temperature and then stirred at 40° C. for 1 hour. Subsequently, at 40° C., 50 g (0.329 mol)

of 4-chloromethylbenzonitrile, dissolved in 500 ml of dioxane, are slowly added dropwise, and the reaction solution is then stirred at 110° C. overnight. After cooling to room temperature, the reaction mixture is added to 1200 ml of water. Care must be taken during this that the pH is <7 (where appropriate, a few ml of 1 M hydrochloric acid are metered in to about pH 2). The mixture is then extracted three times with ethyl acetate, and the combined organic phases are washed with saturated sodium chloride solution and dried over sodium sulfate. After filtration, the solvent is concentrated to dryness in vacuo. Excess diallyl malonate is then removed by high vacuum distillation (boiling point: 57° C.; 0.074 mbar). The distillation residue is purified by flash chromatography on silica gel (mobile phase: petroleum ether/ethyl acetate 20:1). 67 g (0.22 mol, 67% of theory) of a colorless solid are obtained.

$^1$H-NMR (300 MHz, DMSO-$d_6$, δ/ppm): 7.77 (2H, d), 7.48 (2H, d), 5.90-5.73 (2H, m), 5.29-5.13 (4H, m), 4.64-4.50 (4H, m), 4.09 (1H, t), 3.21 (2H, d).

MS (DCI): 317 (M+NH$_4^+$).

Example 26A

Diallyl 2-(4-cyanobenzyl)-2-[2-(4-methoxycarbonylphenyl)ethyl]malonate

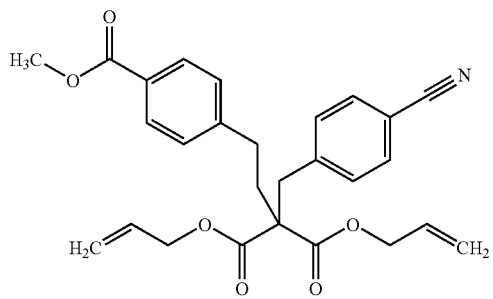

7.13 g (178.36 mmol) of sodium hydride are added in portions to a solution of 48.53 g (162.14 mmol) of diallyl 2-(4-cyanobenzyl)malonate in 180 ml of DMF at 0° C. The reaction solution is then allowed to reach room temperature and is stirred for 30 min. The reaction solution is then cooled to 0° C. again and, after addition of 55 g (194.6 mmol) of methyl 4-(2-bromoethyl)benzoate [CAS No. 136333-97-6] in 195 ml of DMF, stirred at this temperature for 30 min. The mixture is then stirred at room temperature overnight. Water is added dropwise to the reaction mixture, which is then extracted three times with ethyl acetate, and the combined organic phases are washed with saturated sodium chloride solution and dried over sodium sulfate. After filtration, the solvent is concentrated to dryness in vacuo. The resulting crude product is purified by flash chromatography on silica gel (mobile phase: petroleum ether/ethyl acetate 10:1). 33.4 g (72.37 mol, 44% of theory) of a colorless solid are obtained.

$^1$H-NMR (300 MHz, CDCl$_3$, δ/ppm): 7.89 (2H, d), 7.79 (2H, d), 7.38 (2H, d), 7.32 (2H, d), 5.97-5.81 (2H, m), 5.38-5.20 (4H, m), 4.61 (4H, d), 3.82 (3H, s), 3.39 (2H, s), 2.77-2.61 (2H, m), 1.99-1.84 (2H, m).

MS (DCI): 479 (M+NH$_4^+$).

Example 27A

Methyl 4-[3-carboxy-4-(4-cyanophenyl)butyl]benzoate

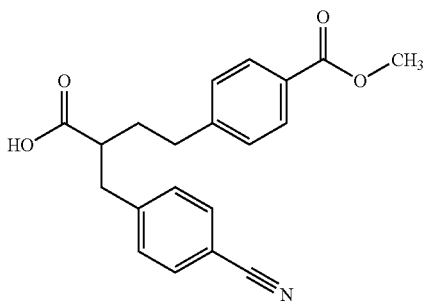

A solution of 7.5 ml (53.6 mmol) of triethylamine and 1.5 ml (40.6 mmol) of formic acid in 170 ml of dioxane is added to a solution of 7.5 g (16.25 mmol) of diallyl 2-(4-cyanobenzyl)-2-[2-(4-methoxycarbonylphenyl)ethyl]malonate, 0.3 g (1.14 mmol) of triphenylphosphine and 70 mg of palladium acetate in 170 ml of dioxane at room temperature. The reaction mixture is then stirred at 100° C. for 2 hours. After conversion is complete, the reaction solution is cooled and the solvent is removed in vacuo. The residue is taken up in ethyl acetate and water and acidified with 1 N hydrochloric acid, and the organic phase is separated off. The aqueous phase is extracted three times more with ethyl acetate, and the organic phases are then combined, washed with saturated sodium chloride solution and dried over sodium sulfate. After filtration, the solution is concentrated in vacuo. 5.48 g (89% of theory, 90% purity) of a colorless solid are obtained.

$^1$H-NMR (400 MHz, DMSO-$d_6$, δ/ppm): 12.46-12.29 (1H, broad), 7.88 (2H, d), 7.74 (2H, d), 7.39 (2H, d), 7.31 (2H, d), 3.83 (3H, s), 2.99-2.83 (2H, m), 2.79-2.56 (3H, m), 1.93-1.67 (2H, m).

MS (DCI): 355 (M+NH$_4^+$).

Example 28A

Methyl 4-[3-(4-cyanobenzyl)-4-hydroxybutyl]benzoate

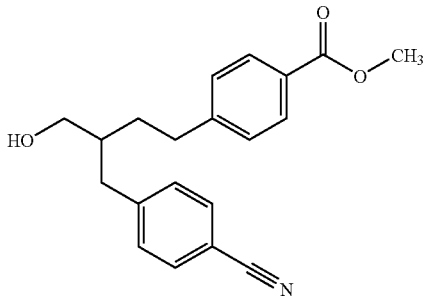

47.43 ml (47.73 mmol) of a 1 M borane-THF complex solution are added dropwise to a solution of 8 g (23.71 mmol) of methyl 4-[3-carboxy-4-(4-cyanophenyl)butyl]benzoate in 200 ml of THF at −10° C. After warming to −5° C., the mixture is stirred at this temperature for a further 4 hours. After reaction is complete, the reaction mixture is mixed with saturated sodium bicarbonate solution, and the solvent is concentrated to dryness. The residue is taken up in dichloromethane, dried over sodium sulfate and again freed of solvent. The resulting crude product is purified by flash chromatography on silica gel (mobile phase: ethyl acetate/cyclohexane 1:10). 5.8 g (98% purity, 74% of theory) of a colorless solid are obtained.

$^1$H-NMR (300 MHz, DMSO-d$_6$, δ/ppm): 7.86 (2H, d), 7.73 (2H, d), 7.38 (2H, d), 7.30 (2H, d), 4.60 (1H, t), 3.83 (3H, s), 3.32 (2H, t), 2.81-2.57 (4H, m), 1.79-1.56 (2H, m), 1.54-1.39 (1H, m).

MS (DCI): 341 (M+NH$_4^+$).

Example 29A

Methyl 4-[3-(4-cyanobenzyl)-4-oxobutyl]benzoate

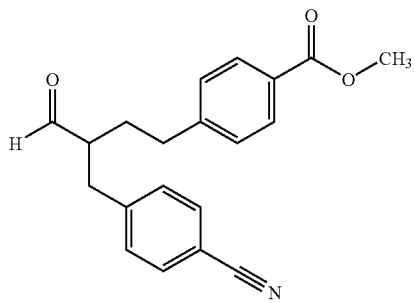

A solution of 400 mg (1.24 mmol) of methyl 4-[3-(4-cyanobenzyl)-4-hydroxybutyl]benzoate in 7 ml of dichloromethane is mixed with 320 mg (1.48 mmol) of pyridinium chlorochromate (PCC) and stirred at room temperature for 5 hours. After conversion is complete, about 1 g of silica gel is added, and the solvent is removed to dryness in vacuo. The residue is purified by flash chromatography on silica gel (mobile phase: cyclohexane/ethyl acetate 10:1→4:1). 302 mg (90% purity, 69% of theory) of a colorless solid are obtained.

$^1$H-NMR (300 MHz, DMSO-d$_6$, δ/ppm): 9.68 (1H, s), 7.87 (2H, d), 7.77 (2H, d), 7.43 (2H, d), 7.31 (2H, d), 3.86 (3H, s), 3.16-3.03 (1H, m), 2.94-2.81 (1H, m), 2.80-2.55 (3H, m), 1.99-1.81 (1H, m), 1.78-1.61 (1H, m).

MS (DCI): 339 (M+NH$_4^+$).

Example 30A

Methyl (4E)-4-[3-(4-cyanobenzyl)-5-(2-hydroxyphenyl)pent-4-enyl]benzoate

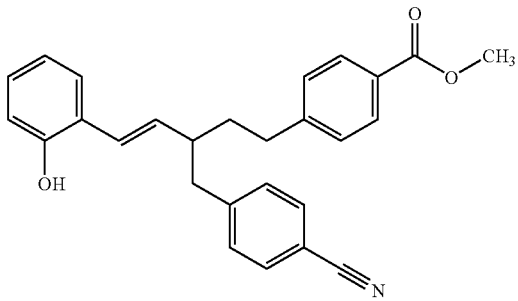

5.91 ml (9.45 mmol) of a 1.6 M solution of n-butyllithium in hexane are slowly added to a solution of 1820 mg (4.05 mmol) of (2-hydroxybenzyl)triphenylphosphonium bromide in 10 ml of anhydrous THF at 0° C. Then, at this temperature, 1085 mg (3.38 mmol) of methyl 4-[3-(4-cyanobenzyl)-4-oxobutyl]benzoate, dissolved in 10 ml of THF, are slowly metered in. After warming to room temperature, the reaction solution is stirred for 12 hours, then some water is added and the mixture is concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 4:1→2:1). 1150 mg (2.79 mmol, 83% of theory) of a colorless solid are obtained.

$^1$H-NMR (300 MHz, DMSO-d$_6$, δ/ppm): 9.47 (1H, s), 7.88 (2H, d), 7.71 (2H, d), 7.42-7.27 (5H, m), 7.01 (1H, t), 6.81-6.68 (2H, m), 6.45 (1H, d), 6.12-6.00 (1H, m), 3.84 (3H, s), 3.42 (2H, m), 2.95-2.56 (3H, m), 1.88-1.56 (2H, m).

MS (DCI): 429 (M+NH$_4^+$).

Example 31A

Methyl 4-((4E)-3-(4-cyanobenzyl)-5-{2-[phenylpentyl)oxy]phenyl}pent-4-en-1-yl)benzoate

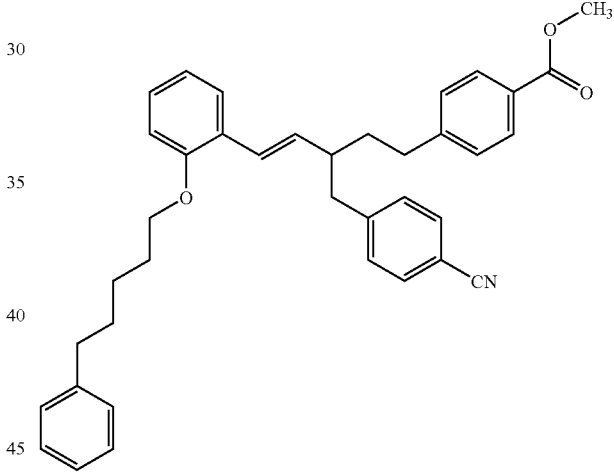

A solution of 300 mg (0.73 mmol) of methyl 4-[(4E)-3-(4-cyanobenzyl)-5-(2-hydroxyphenyl)pent-4-en-1-yl]benzoate in 30 ml of dry acetonitrile is mixed with 198.72 mg (0.87 mmol) of (5-bromopentyl)benzene and 151 mg (1.09 mmol) of anhydrous potassium carbonate and heated under reflux for 12 h. The mixture is then concentrated to dryness. The residue is taken up in ethyl acetate, washed with water and saturated sodium chloride solution and dried over sodium sulfate. The organic phase is concentrated. The resulting crude product is purified by flash chromatography on silica gel (mobile phase: cyclohexane/ethyl acetate 7:3). 295 mg (0.53 mmol, 72.6% of theory) of an oil are obtained.

$^1$H-NMR (400 MHz, DMSO-d$_6$, δ/ppm): 7.83 (2H, d), 7.71 (2H, d), 7.4-7.33 (2H, m), 7.29 (2H, d), 7.27-7.21 (2H, m), 7.2-7.1 (5H, m), 6.95-6.83 (2H, m), 6.44-6.35 (1H, m), 6.11-6.03 (1H, m), 3.95-3.83 (2H, m), 3.79 (3H, s), 2.91-2.79 (1H, m), 2.79-2.57 (3H, m), 2.57-2.39 (4H, m), 1.84-1.73 (1H, m), 1.72-1.5 (6H, m).

LC-MS (method 1): R$_t$=3.57 min.

MS (ESIpos): m/z=558 (M+H)$^+$.

Example 32A

Methyl 4-{(4E)-5-{2-[(5-phenylpentyl)oxy]phenyl}-3-[4-(1H-tetrazol-5-yl)benzyl]pent-4-en-1-yl}benzoate

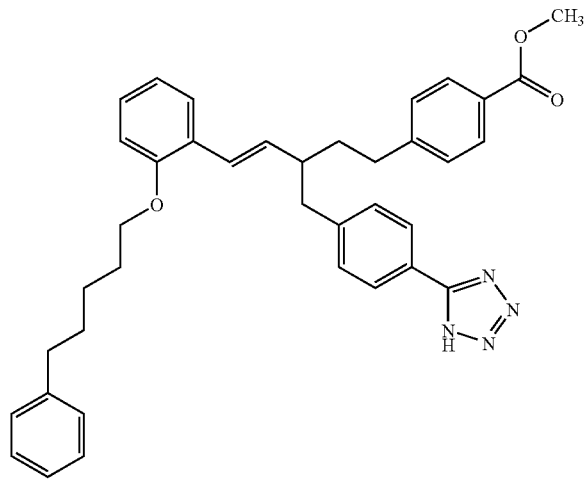

A solution of 295 mg (0.53 mmol) of methyl 4-((4E)-3-(4-cyanobenzyl)-5-{2-[(5-phenylpentyl)oxy]phenyl}pent-4-en-1-yl)benzoate in 20 ml of toluene is mixed with 1.05 ml (7.93 mmol) of trimethylsilyl azide and 198 mg (0.79 mmol) of di-n-butyltin oxide and heated at 80° C. for 12 hours. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by flash chromatography on silica gel (mobile phase: dichloromethane→dichloromethane/methanol 10:1). 284 mg (0.47 mmol, 89% of theory) of a white foam are obtained.

LC-MS (method 1): $R_f$=3.40 min.

MS (ESIpos): m/z=601 (M+H)$^+$.

Example 33A

E-5-Fluoro-2-[2-(4-methoxyphenyl)vinyl]benzaldehyde

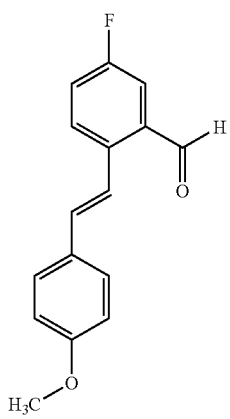

A solution of 10 g (49.26 mmol) of 2-bromo-5-fluorobenzaldehyde in 200 ml of dry DMF is mixed with 7.27 g (54.18 mmol) of 4-methoxystyrene, 1.5 g (4.93 mmol) of tri-2-tolylphosphine, 330 mg (1.48 mmol) of palladium(II) acetate and 10.3 ml (73.89 mmol) of triethylamine under argon and stirred at 100° C. for 12 hours. After reaction is complete, the reaction solution is cooled to room temperature and concentrated to dryness. The residue is taken up in 100 ml of water and extracted three times with 50 ml of diethyl ether each time. The combined organic phases are dried over sodium sulfate. After filtration, the solution is concentrated to dryness, and the residue is purified by flash chromatography on silica gel (mobile phase: cyclohexane/ethyl acetate 10:1). 7.79 g (55% of theory) of a colorless solid are obtained.

$^1$H-NMR (400 MHz, DMSO-d$_6$, δ/ppm): 10.40 (1H, s), 8.01-7.89 (2H, m), 7.68-7.49 (4H, m), 7.22 (1H, d), 6.99 (2H, d), 3.80 (3H, s).

MS (DCI): 274 (M+NH$_4^+$).

Example 34A

E-{5-Fluoro-2-[2-(4-methoxyphenyl)vinyl]phenyl}methanol

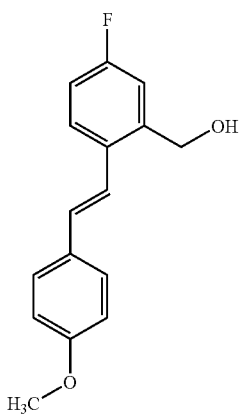

1.73 g (45.60 mmol) of sodium borohydride are added in portions to a solution of 7.79 g (30.40 mmol) of E-5-fluoro-2-[2-(4-methoxyphenyl)vinyl]benzaldehyde in 500 ml of methanol at 0° C., and the mixture is stirred at room temperature for 2 hours. After reaction is complete, the mixture is concentrated to dryness and the residue is taken up in water and dichloromethane. The aqueous phase is extracted twice more with dichloromethane. The combined organic phases are dried over sodium sulfate, filtered and concentrated to dryness. The resulting residue is purified by flash chromatography on silica gel (mobile phase: cyclohexane/ethyl acetate 4:1→1:1). 6.8 g (85% of theory) of a colorless solid are obtained.

$^1$H-NMR (400 MHz, DMSO-d$_6$, δ/ppm): 7.71 (1H, m), 7.54 (2H, d), 7.27-7.12 (2H, m), 7.11-6.99 (2H, m), 6.97 (2H, d), 5.47 (1H, t), 4.67 (2H, d), 3.79 (3H, s).

LC-MS (method 1): $R_t$ 2.49 min; m/z 259 (M+H$^+$).

Example 35A

{5-Fluoro-2-[2-(4-methoxyphenyl)ethyl]phenyl}methanol

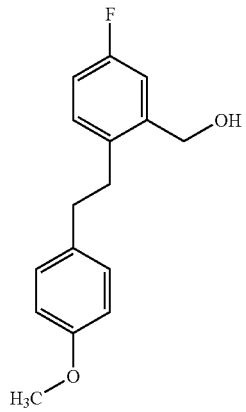

A mixture of 6.8 g (26.33 mmol) of E-{5-fluoro-2-[2-(4-methoxyphenyl)vinyl]phenyl}methanol and 0.5 g of 10% palladium on carbon in 50 ml of methanol and 250 ml of ethanol is hydrogenated under atmospheric pressure at room temperature for 1 hour. After reaction has stopped, the mixture is filtered through kieselguhr and the filtrate is then concentrated to dryness. The resulting residue is purified by flash chromatography on silica gel (mobile phase: cyclohexane/ethyl acetate 10:1→4:1→1:1). 5.95 g (87% of theory) of a colorless solid are obtained.

$^1$H-NMR (400 MHz, DMSO-d$_6$, δ/ppm): 7.21-7.09 (4H, m), 6.97 (1H, t), 6.83 (2H, d), 5.24 (1H, t), 4.51 (2H, d), 3.72 (3H, s), 2.81-2.68 (4H, m). LC-MS (method 1): R$_t$ 2.49 min; m/z 278 (M+NH$_4^+$).

Example 36A

{5-Fluoro-2-[2-(4-methoxyphenyl)ethyl]benzyl}triphenylphosphonium bromide

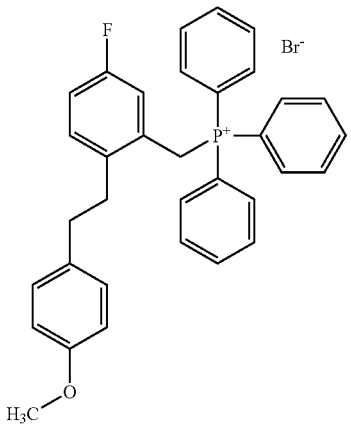

A solution of 5.95 g (22.86 mmol) of {5-fluoro-2-[2-(4-methoxyphenyl)ethyl]phenyl}methanol in 130 ml of acetonitrile is mixed with 7.45 g (21.71 mmol) of triphenylphosphonium bromide and heated under reflux for 3 hours. The reaction solution is then concentrated to dryness, and the resulting oil is triturated in diethyl ether. The product crystallizes as a white solid during this. After filtration, the solid is dried in a drying oven at 50° C. overnight. 11.5 g (77% of theory) of the title compound are obtained.

$^1$H-NMR (300 MHz, DMSO-d$_6$, δ/ppm): 7.92 (3H, t), 7.81-7.69 (6H, m), 7.68-7.57 (6H, m), 7.30-7.21 (1H, m), 7.19-7.08 (1H, m), 6.94 (2H, d), 6.81 (2H, d), 6.70-6.58 (1H, m), 4.94 (2H, d), 3.71 (3H, s), 2.57-2.46 (2H, t), 2.18 (2H, t).

Example 37A

Methyl 4-((4E/Z)-3-(4-cyanobenzyl)-5-{5-fluoro-2-[2-(4-methoxyphenyl)ethyl]phenyl}pent-4-en-1-yl)benzoate

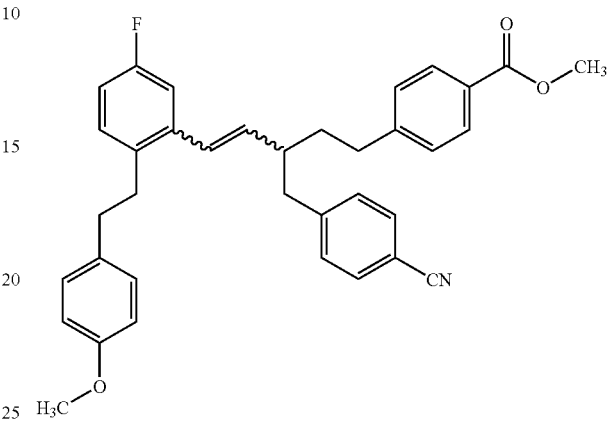

4.38 ml (7 mmol) of a 1.6 M solution of n-butyllithium in hexane are slowly added to a solution of 1.5 g (4.67 mmol) of {5-fluoro-2-[2-(4-methoxyphenyl)ethyl]benzyl}(triphenyl)phosphonium bromide at 0° C. Then, at this temperature, 3.280 g (5.6 mmol) of methyl 4-[3-(4-cyanobenzyl)-4-oxobutyl]benzoate are slowly metered in. After warming to room temperature, the reaction solution is stirred for 12 h then mixed with a little water and concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 50:1→20:1). 2.17 g (3.9 mmol, 84% of theory) of a white foam are obtained.

MS (ESIpos): m/z=548 (M+H)$^+$.

Example 38A

Methyl 4-{(4E/Z)-5-{5-fluoro-2-[2-(4-methoxyphenyl)ethyl]phenyl}-3-[4-(1H-tetrazol-5-yl)benzyl]pent-4-en-1-yl}benzoate

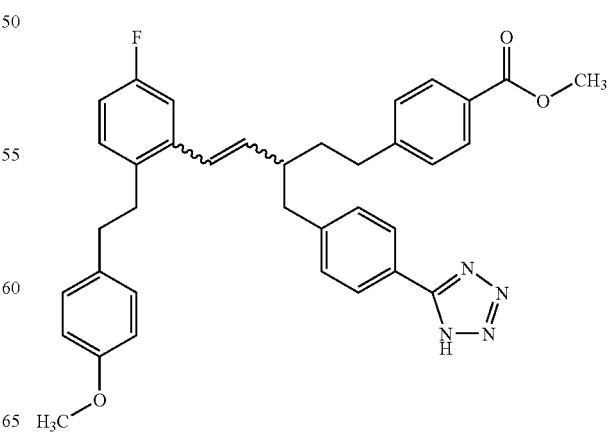

A solution of 600 mg (1.1 mmol) of methyl 4-((4E/Z)-3-(4-cyanobenzyl)-5-{5-fluoro-2-[2-(4-methoxyphenyl)ethyl]phenyl}pent-4-en-1-yl)benzoate in 30 ml of toluene is mixed with 2.18 ml (16.43 mmol) of trimethylsilyl azide and 409 mg (1.64 mmol) of di-n-butyltin oxide and heated at 80° C. for 12 h. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. 642 mg (1.01 mmol, 99% of theory) of a white foam are obtained.

LC-MS (method 1): $R_t$=3.19 min.
MS (ESIpos): m/z=591 (M+H)$^+$.

Example 39A

Ethyl 4'-trifluoromethylbiphenyl-4-carboxylate

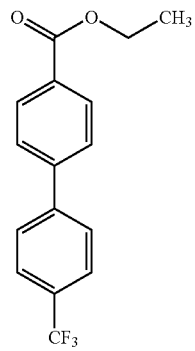

7 g (30.56 mmol) of ethyl 4-bromobenzoate are dissolved in 60 ml of 1,2-dimethoxyethane and, under argon, 6.96 g (36.67 mmol) of 4-trifluoromethylphenylboronic acid, 271 mg of bis(triphenylphosphine)palladium(II) chloride and 40.7 ml of a 2 M sodium carbonate solution in water are added. The reaction mixture is then stirred under reflux for 12 hours. The mixture is subsequently cooled, filtered through 1 g of Extrelute, washed with dichloromethane and concentrated. The resulting crude product is purified by flash chromatography on silica gel (mobile phase: cyclohexane/dichloromethane 2:1). 6.31 g (21.4 mmol, 70% of theory) of a colorless solid are obtained.

$^1$H-NMR (300 MHz, CDCl$_3$, δ/ppm): 8.17 (2H, d), 7.72 (4H, s), 7.67 (2H, d), 4.41 (2H, q), 1.43 (3H, t).
MS (EI): 294 (M$^+$).

Example 40A (4'-Trifluoromethylbiphenyl-4-yl)methanol

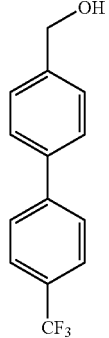

12.73 ml (12.73 mmol) of a 1 M solution of lithium aluminum hydride in THF are added dropwise to a solution of 6.24 g (21.21 mmol) of ethyl 4'-trifluoromethylbiphenyl-4-carboxylate in 60 ml of dry THF at 0° C. After the reaction is complete, the mixture is mixed with saturated ammonium chloride solution and taken up in ethyl acetate, and the organic phase is separated off and dried over sodium sulfate. After filtration, the solvent is removed in vacuo. The resulting crude product is purified by flash chromatography on silica gel (mobile phase: cyclohexane/ethyl acetate 5:1). 5.1 g (20.21 mmol, 95% of theory) of a colorless solid are obtained.

$^1$H-NMR (300 MHz, DMSO-d$_6$, δ/ppm): 7.88 (2H, d), 7.82 (2H, d), 7.71 (2H, d), 7.46 (2H, d), 5.23 (1H, t), 4.58 (2H, d).
MS (EI): 252 (M$^+$).

Example 41A

4-Chloromethyl-4'-trifluoromethylbiphenyl

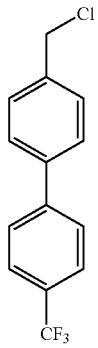

A solution of 5.0 g (19.82 mmol) of (4'-trifluoromethylbiphenyl-4-yl)methanol in 40 ml of chloroform is mixed with 2.89 ml (39.65 mmol) of thionyl chloride dissolved in 10 ml of chloroform, and the mixture is stirred at room temperature for 12 hours. After reaction is complete, the reaction mixture is concentrated to dryness, and the residue is taken up in ethyl acetate and washed with saturated sodium carbonate solution. The organic phase is subsequently separated off, dried over sodium sulfate and concentrated after filtration. The resulting crude product is purified by flash chromatography on silica gel (mobile phase: cyclohexane/ethyl acetate 9:1). 5.26 g (19.43 mmol, 98% of theory) of a colorless solid are obtained.

$^1$H-NMR (300 MHz, DMSO-d$_6$, δ/ppm): 7.91 (2H, d), 7.82 (2H, d), 7.78 (2H, d), 7.58 (2H, d), 4.83 (2H, s).
MS (EI): 270 (M$^+$).

Example 42A

Methyl 4-[(4E)-3-(4-cyanobenzyl)-5-(2-{[4'-(trifluoromethyl)biphenyl-4-yl]methoxy}phenyl)pent-4-en-1-yl]benzoate

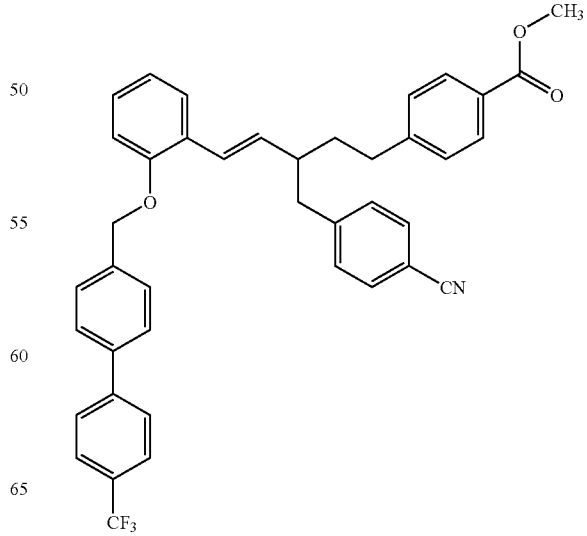

A solution of 300 mg (0.73 mmol) of methyl 4-[(4E)-3-(4-cyanobenzyl)-5-(2-hydroxyphenyl)pent-4-en-1-yl]benzoate in 30 ml of dry acetonitrile is mixed with 236.8 mg (0.87 mmol) of 4-(chloromethyl)-4'-(trifluoromethyl)biphenyl and 151 mg (1.09 mmol) of anhydrous potassium carbonate and heated under reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by flash chromatography on silica gel (mobile phase: cyclohexane/ethyl acetate 7:3). 331 mg (0.51 mmol, 70% of theory) of a solid are obtained.

LC-MS (method 1): $R_f$=3.57 min.

MS (ESIpos): m/z=646 (M+H$^+$).

Example 43A

Methyl 4-[(4E)-3-[4-(1H-tetrazol-5-yl)benzyl]-5-(2-{[4'-(trifluoromethyl)biphenyl-4-yl]methoxy}-phenyl)pent-4-en-1-yl]benzoate

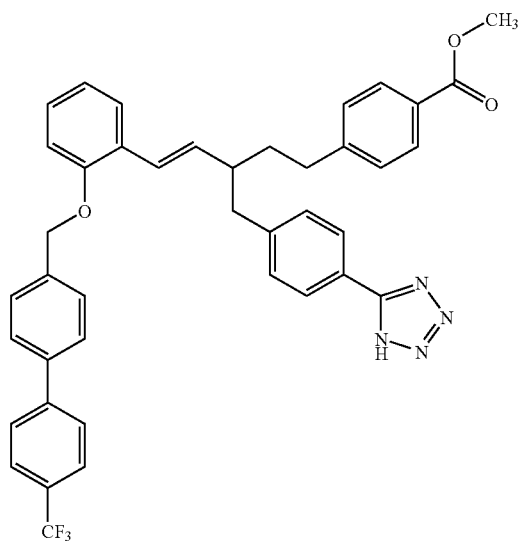

A solution of 295 mg (0.53 mmol) of methyl 4-[(4E)-3-(4-cyanobenzyl)-5-(2-{[4'-(trifluoromethyl)biphenyl-4-yl]methoxy}phenyl)pent-4-en-1-yl]benzoate in 20 ml of toluene is mixed with 1.33 ml (9.99 mmol) of trimethylsilyl azide and 249 mg (1 mmol) of di-n-butyltin oxide and heated at 80° C. for 12 hours. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by flash chromatography on silica gel (mobile phase: dichloromethane→dichloromethane/methanol 10:1). 387 mg (0.56 mmol, 64% of theory) of a white foam are obtained.

LC-MS (method 1): $R_f$=3.42 min.

MS (ESIpos): m/z=689 (M+H$^+$).

Example 44A

Methyl 4-[(4E)-5-{2-[(4-tert-butylbenzyl)oxy]phenyl}-3-(4-cyanobenzyl)pent-4-en-1-yl]benzoate

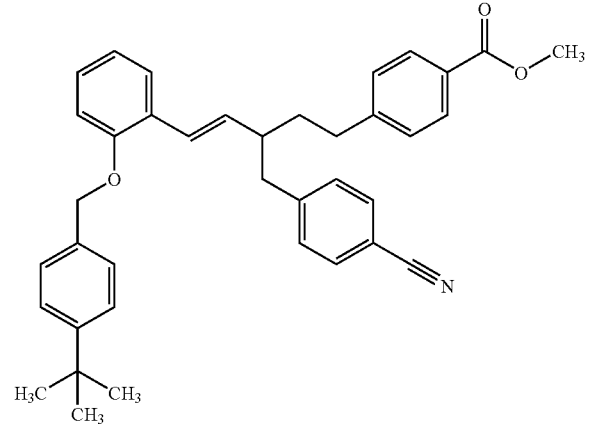

A solution of 1.4 g (3.13 mmol, 92% pure) of methyl E-4-[3-(4-cyanobenzyl)-5-(2-hydroxyphenyl)pent-4-enyl]benzoate in 7 ml of dry acetonitrile is mixed with 1.42 g (6.26 mmol) 4-(tert-butyl)benzyl bromide and 1.30 g (9.39 mmol) of anhydrous potassium carbonate and heated under reflux for 12 hours. The mixture is then filtered and concentrated to dryness. The residue is directly purified by chromatography on silica gel (mobile phase: cyclohexane/ethyl acetate 10:1, then 1:5). 1.85 g (3.32 mmol, 93% purity, 98% of theory) of an oil are isolated.

$^1$H-NMR (300 MHz, CDCl$_3$, δ/ppm): 7.94-7.88 (2H, m), 7.52-7.14 (12H, m), 6.97-6.89 (2H, m), 6.67-6.57 (1H, m), 6.02-5.92 (1H, m), 5.05-5.02 (2H, m), 3.90 (3H, s), 2.85-2.67 (3H, m), 2.67-2.55 (1H, m), 2.54-2.42 (1H, m), 1.88-1.61 (2H, m), 1.33 (9H, s).

LC-MS (method 4): $R_t$ 3.53 min; m/z 557 (M$^+$).

Example 45A

Methyl 4-{(4E)-5-{2-[(4-tert-butylbenzyl)oxy]phenyl}-3-[4-(1H-tetrazol-5-yl)benzyl]pent-4-en-1-yl}benzoate

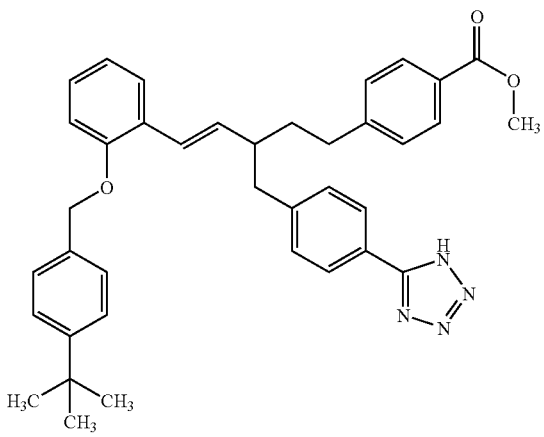

A solution of 180 mg (0.32 mmol) of methyl 4-[(4E)-5-{2-[(4-tert-butylbenzyl)oxy]phenyl}-3-(4-cyanobenzyl)pent-4-en-1-yl]benzoate in 10 ml of toluene is mixed with 557.3 mg (4.84 mmol) of trimethylsilyl azide and 120.51 mg (0.48 mmol) of di-n-butyltin oxide and heated at 80° C. for 12 hours. After cooling to room temperature, the mixture is washed with saturated sodium bicarbonate solution. The organic phase is separated off, washed with saturated sodium chloride solution and dried over sodium sulfate. After filtration the filtrate is concentrated to dryness. The resulting crude product is purified on a silica gel column (mobile phase: cyclohexan/ethyl acetate 2:1→1:2). 88 mg (0.14 mmol, 43% of theory) of a white foam are obtained.

$^1$H-NMR (300 MHz, CDCl$_3$, δ/ppm): 13.15 (1H, broad), 7.87-7.73 (4H, m), 7.49-7.31 (6H, m), 7.18 (2H, d), 7.09 (2H, d), 6.99-6.9 (2H, m), 6.7 (1H, d), 6.05 (1H, dd), 5.03 (2H, s), 3.94 (3H, s), 2.86-2.66 (3H, m), 2.66-2.51 (1H, m), 2.49-2.34 (1H, m), 1.85-1.62 (2H, m), 1.32 (9H, s).

Example 46A

Diallyl 2-(4-cyanobutyl)malonate

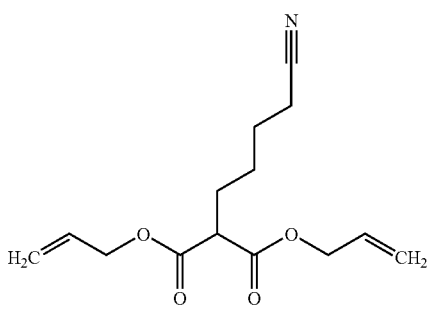

21.71 g (542.9 mmol; 60% pure) of sodium hydride are added in portions to a solution of 100 g (542.9 mmol) of diallyl malonate in 700 ml of dry dioxane at 0° C. After gas evolution ceases, the reaction mixture is warmed to 40° C. and stirred for 1 hour. Then 43.98 g (271.5 mmol) of 5-bromovaleronitrile in 350 ml of dry dioxane are added dropwise, and the mixture is stirred at 110° C. for 12 hours. After the reaction is complete, the mixture is cooled to room temperature, mixed with 400 ml of saturated ammonium chloride solution and extracted with ethyl acetate. After phase separation, the aqueous phase is extracted three further times with 250 ml of ethyl acetate each time. After the organic phases have been combined they are washed with saturated sodium chloride solution and dried over sodium sulfate, and then the solvent is stripped off in vacuo. Excess diallyl malonate is subsequently removed by high vacuum distillation (boiling point: 57° C.; 0.074 mbar). The resulting distillation residue is purified by flash chromatography on silica gel (mobile phase: cyclohexane/ethyl acetate 2:1). 105 g (233 mmol, approx. 60% purity, 43% of theory) of the title compound are obtained, which compound is reacted without further purification in the subsequent stage. A small amount is purified by preparative HPLC for analytical characterization.

$^1$H-NMR (300 MHz, DMSO-d$_6$, δ/ppm): 5.96-5.83 (2H, m), 5.35-5.19 (4H, m), 4.64-4.59 (4H, m), 3.66-3.61 (1H, t), 2.54-2.47 (2H, t), 1.86-1.75 (2H, m), 1.62-1.50 (2H, m), 1.42-1.29 (2H, m).

LC-MS (method 1): R$_t$ 2.44 min, m/z 266 (M+H)$^+$.

Example 47A

Diallyl 2-(4-cyanobutyl)-2-[2-(4-methoxycarbonylphenyl)ethyl]malonate

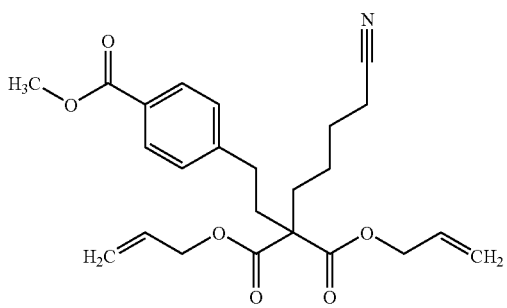

5.62 g (140 mmol; 60% pure) of sodium hydride are added in portions to a solution of 48.64 g (127.73 mmol) of diallyl 2-(4-cyanobutyl)malonate in 160 ml of dry DMF at 0° C. The reaction solution is then allowed to reach room temperature and is stirred for 90 min. The reaction solution is then cooled to 0° C. again and, after addition of 45.72 g (153.3 mmol) of methyl 4-(2-bromoethyl)benzoate in 80 ml of dry DMF, stirred at this temperature for 45 min. The mixture is then stirred at room temperature overnight. The reaction mixture is mixed with water and extracted with ethyl acetate. After phase separation, the aqueous phase is extracted three more times with 200 ml of ethyl acetate each time. After combining the combined organic phases, the mixture is washed with saturated sodium chloride solution and dried over sodium sulfate, and then the solvent is stripped off in vacuo. The resulting crude product is purified by silica gel chromatography (mobile phase: cyclohexane/ethyl acetate 10:1→100% ethyl acetate). 18.53 g (43.3 mmol, 34% of theory) of a colorless liquid are obtained.

$^1$H-NMR (300 MHz, DMSO-d$_6$, δ/ppm): 7.90-7.88 (2H, d), 7.36-7.34 (2H, d), 5.97-5.83 (2H, m), 5.35-5.21 (4H, m), 4.64-4.59 (4H, m), 3.84 (3H, s), 2.57-2.48 (4H, t), 2.15-2.09 (2H, m), 1.98-1.89 (2H, m), 1.63-1.52 (2H, m), 1.34-1.21 (2H, m).

LC-MS (method 2): R$_t$ 2.59 min; m/z 428 (M+H)$^+$.

Example 48A

Methyl 4-(3-carboxy-7-cyanoheptyl)benzoate

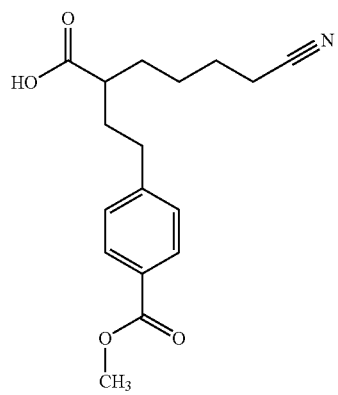

A solution of 7.45 ml (53.42 mmol) of triethylamine and 1.53 ml (40.47 mmol) of formic acid in 67 ml of dioxane is added to a solution of 6.92 g (16.19 mmol) of diallyl 2-(4-cyanobutyl)-2-[2-(4-methoxycarbonylphenyl)ethyl]malonate, 594 mg (2.26 mmol) of triphenylphosphine and 145 mg (0.64 mmol) of palladium acetate in 67 ml of dioxane at room temperature. The reaction mixture is then stirred at 100° C. for 12 hours. After conversion is complete, the reaction solution is cooled and the solvent is removed in vacuo. The residue is taken up in ethyl acetate and water and acidified with 1 N hydrochloric acid, and the organic phase is separated off. The aqueous phase is extracted three more times with ethyl acetate, and the organic phases are then combined, washed with saturated sodium chloride solution and dried over sodium sulfate. After filtration, the solution is concentrated in vacuo. The resulting crude product is purified by flash chromatography on silica gel [mobile phase: cyclohexane/ethyl acetate (with 1% formic acid) 2:1→1:3]. 2.1 g (43% of theory) of a colorless solid are obtained.

LC-MS (method 2): $R_t$ 1.88 min; m/z 303 (M+).

Example 49A

Methyl 4-(7-cyano-3-hydroxymethylheptyl)benzoate

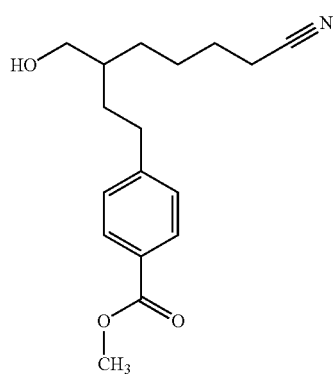

33 ml (33 mmol) of a 1 M borane-THF complex solution are added dropwise to a solution of 5 g (16.48 mmol) of methyl 4-(3-carboxy-7-cyanoheptyl)benzoate in 62 ml of THF at −15° C., and the solution is stirred at this temperature for 2 hours. Then a further 16 ml (16 mmol) of 1 M borane-THF complex solution are added dropwise at −15° C., and stirring is continued for 45 minutes. The reaction mixture is then warmed to 0° C. and stirred at this temperature for 1 hour. After reaction is complete, 100 ml of saturated bicarbonate solution are added to the reaction mixture, and the solvent is concentrated to dryness. The residue is taken up in ethyl acetate and water, and the aqueous phase is extracted again with ethyl acetate. The combined organic phases are dried over sodium sulfate and again freed of solvent. The resulting crude product is purified by flash chromatography on silica gel (mobile phase: cyclohexane/ethyl acetate 2:1→1:3→100% ethyl acetate). 2.4 g (93% purity, 47% of theory) of a colorless solid are obtained.

$^1$H-NMR (400 MHz, DMSO-$d_6$, δ/ppm): 7.88-7.86 (2H, d), 7.36-7.34 (2H, d), 4.43-4.40 (1H, t), 3.83 (3H, s), 3.37-3.34 (2H, t), 2.68-2.64 (2H, t), 2.49-2.46 (2H, t), 1.67-1.57 (1H, m), 1.56-1.45 (3H, m), 1.42-1.25 (5H, m).

LC-MS (method 2): $R_t$ 1.93 min; m/z 290 (M+H)+.

Example 50A

Methyl 4-(7-cyano-3-formylheptyl)benzoate

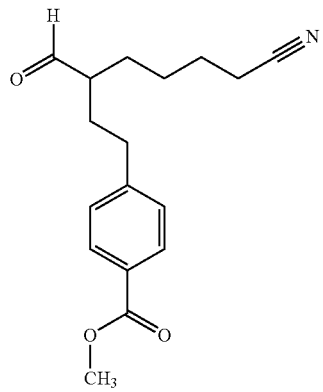

A solution of 2.23 g (7.71 mmol) of methyl 4-(7-cyano-3-hydroxymethylheptyl)benzoate in 100 ml of dichloromethane is mixed with 1.99 g (9.26 mmol) of pyridinium chlorochromate (PCC) and stirred at room temperature for 6 hours. After conversion is complete, the solvent is concentrated to dryness in vacuo. The resulting residue is purified by flash chromatography on silica gel (mobile phase: cyclohexane/ethyl acetate 10:1→4:1). 1.50 g (9.09 mmol, 68% of theory) of an oil are obtained.

$^1$H-NMR (400 MHz, CDCl$_3$, δ/ppm): 9.62 (1H, d), 7.98-7.96 (2H, d), 7.25-7.23 (2H, d), 3.91 (3H, s), 2.77-2.62 (2H, m), 2.35 (2H, t), 2.38-2.29 (1H, m), 2.07-1.98 (1H, m), 1.82-1.63 (4H, m), 1.55-1.47 (3H, m).

MS (ESI): 310 (M+Na)+.

Example 51A

Methyl E-4-{7-cyano-3-[2-(2-hydroxyphenyl)vinyl]heptyl}benzoate

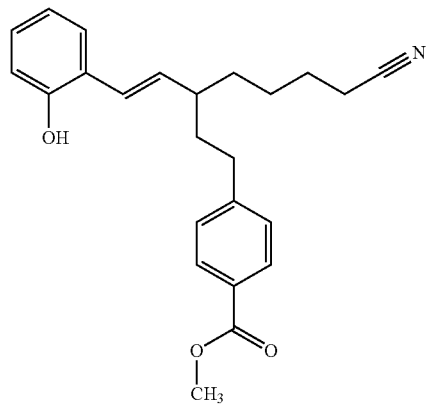

9.07 ml (14.52 mmol) of a 1.6 M solution of n-butyllithium in hexane are slowly added dropwise to a suspension of 3.26 g (7.26 mmol) of 2-hydroxyphenyltriphenylphosphonium bromide in 40 ml of dry THF at 0° C., and the mixture is stirred for 5 minutes. Then, at this temperature, a solution of 1.49 g (5.19 mmol) of methyl 4-(7-cyano-3-formylheptyl)benzoate in 10 ml of dry THF is slowly added dropwise. The reaction mixture is stirred at 0° C. for 10 minutes. The cooling is then removed, and the reaction solution is stirred at room temperature for 10 minutes and then mixed with silica gel and concentrated to dryness. The resulting residue is purified directly by flash chromatography on silica gel (mobile phase: cyclohexane/ethyl acetate 1:2→1:5). 1.71 g (75% purity, 3.40 mmol, 65% of theory) of an oil are obtained.

$^1$H-NMR (300 MHz, DMSO-d$_6$, δ/ppm): 9.50 (1H, s), 7.88-7.86 (2H, d), 7.40-7.34 (3H, m), 7.05-7.00 (1H, m), 6.84-6.68 (2H, m), 6.62-6.56 (1H, m), 6.05-5.97 (1H, dd), 3.83 (3H, s), 2.75-2.56 (2H, m), 2.52-2.44 (3H, m), 2.18-2.06 (1H, m), 1.81-1.28 (7H, m).

LC-MS (method 2): R$_t$ 2.60 min; m/z 377 (M$^+$).

Example 52A

Methyl E-4-(3-{2-[2-(4-tert-butylbenzyloxy)phenyl]vinyl}-7-cyanoheptyl)benzoate

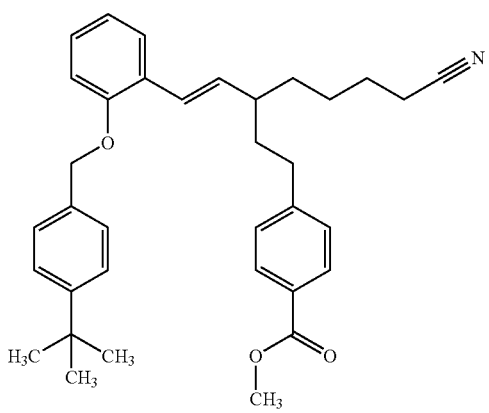

A solution of 1.70 g (3.38 mmol, 75% pure) of methyl 4-{7-cyano-3-[2-(2-hydroxyphenyl)vinyl]-heptyl}benzoate in 20 ml of dry acetonitrile is mixed with 1.53 g (7.76 mmol) of 4-(tert-butyl)benzyl bromide and 1.4 g (10.13 mmol) of anhydrous potassium carbonate and heated under reflux for 12 hours. The mixture is then filtered and the filtrate is concentrated to dryness. The resulting crude product is taken up on silica gel and purified by flash chromatography (mobile phase: cyclohexane/ethyl acetate 10:1). 1700 mg (3.12 mmol, 96% purity, 92% of theory) of an oil are obtained.

$^1$H-NMR (400 MHz, CDCl$_3$, δ/ppm): 7.93-7.71 (2H, d), 7.46-7.35 (5H, m), 7.24-7.18 (3H, m), 6.97-6.93 (2H, m), 6.77-6.73 (1H, d), 5.98-5.92 (1H, dd), 5.11-5.05 (2H, m), 3.90 (3H, s), 2.79-2.70 (1H, m), 2.66-2.57 (1H, m), 3.36 (2H, t), 2.20-2.11 (1H, m), 1.82-1.73 (1H, m), 1.70-1.56 (3H, m), 1.56-1.35 (9H, s).

LC-MS (method 4): R$_t$ 3.36 min; m/z 523 (M$^+$).

Example 53A

Methyl 4-[3-((E)-2-{2-[(4-tert-butylbenzyl)oxy]phenyl}vinyl)-7-(1H-tetrazol-5-yl)heptyl]benzoate

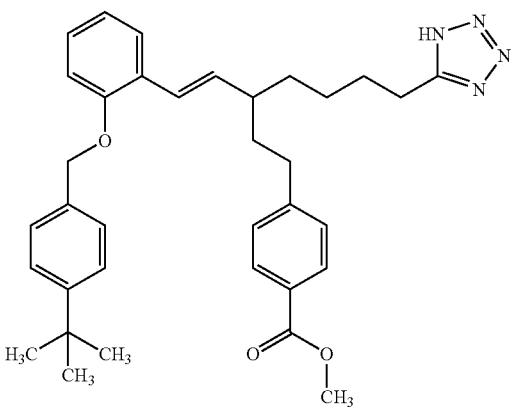

A solution of 200 mg (0.38 mmol) of methyl 4-[3-((E)-2-{2-[(4-tert-butylbenzyl)oxy]phenyl}vinyl)-7-cyanoheptyl)benzoate in 3 ml of toluene is mixed with 660 mg (5.73 mmol) of trimethylsilyl azide and 142.6 mg (0.57 mmol) of di-n-butyltin oxide and heated to 80° C. for 12 hours. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by chromatography on a silica gel column (mobile phase: cyclohexane/ethyl acetate 1:1). 103 mg (0.18 mmol, 46% of theory) of a white foam are obtained.

$^1$H-NMR (300 MHz, CDCl$_3$, δ/ppm): 12.34 (1H, broad), 7.93 (2H, d), 7.47-7.33 (6H, m), 7.22 (3H, d), 7.06-6.93 (2H, m), 6.74 (1H, d), 5.91 (1H, dd), 5.18-5.02 (2H, m), 3.90 (3H, s), 2.89-2.54 (4H, m), 2.22-2.06 (1H, m), 1.83-1.53 (4H, m), 1.52-1.19 (13H, m).

Example 54A

1-Allyl 7-ethyl 2-allyloxycarbonylheptanedioate

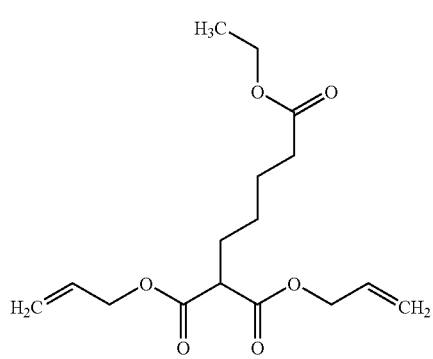

16.29 g (407.19 mmol) of sodium hydride are added in portions to a solution of 100 g (542.92 mmol) of diallyl malonate in 900 ml of dry dioxane at 5° C. After gas evolution ceases, the reaction mixture is warmed to 40° C. and stirred for 30 min. Then 56.76 g (271.46 mmol) of ethyl 5-bromovalerate in 100 ml of dry dioxane are added dropwise, and the mixture is stirred at 110° C. for 12 hours. After the reaction is complete, the mixture is cooled to room temperature and added to about 400 ml of ice-water. After neutralization with 1 N hydrochloric acid, the organic phase is separated off, and the aqueous phase is extracted three times with 250 ml of ethyl acetate each time. After the organic phases have been combined they are washed with saturated sodium chloride solution and dried over sodium sulfate. After filtration, the solution is concentrated in vacuo. Subsequently excess diallyl malonate is removed by high vacuum distillation (boiling point: 57° C., 0.074 mbar). The resulting distillation residue is purified by flash chromatography on silica gel (mobile phase: cyclohexane/ethyl acetate 2:1). 73.92 g (236.65 mmol, 44% of theory) of a colorless liquid are obtained.

$^1$H-NMR (400 MHz, DMSO-d$_6$, δ/ppm): 5.99-5.81 (2H, m), 5.38-5.16 (4H, m), 4.68-4.51 (4H, m), 4.04 (2H, q), 3.59 (1H, t), 2.28 (2H, t), 1.86-1.71 (2H, m), 1.61-1.45 (2H, m), 1.35-1.20 (2H, m), 1.17 (3H, t).

MS (DCI): 330 (M+NH$_4^+$).

Example 55A

1-Allyl 7-ethyl 2-allyloxycarbonyl-2-[2-(4-cyanophenyl)ethyl]heptandioate

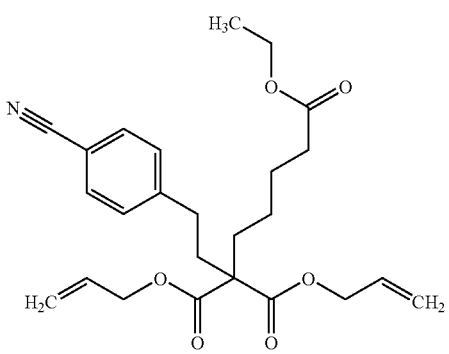

6.37 g (159.27 mmol; 60% pure) of sodium hydride are added in portions to a solution of 45.23 g (144.79 mmol) of 1-allyl 7-ethyl 2-allyloxycarbonylheptanedioate in 250 ml of DMF at 0° C. The reaction solution is then allowed to reach room temperature and is stirred for 30 min. The reaction solution is then cooled to 0° C. and, after addition of 36.50 g (173.75 mmol) of 4-(2-bromoethyl)benzonitrile in 250 ml DMF, stirred at this temperature for 30 min. The mixture is then stirred at room temperature overnight. Water is added dropwise to the reaction mixture and, after extraction three times with ethyl acetate, the combined organic phases are washed with saturated sodium chloride solution and dried over sodium sulfate. After filtration, the solvent is concentrated to dryness in vacuo. The resulting crude product is purified by flash chromatography on silica gel (mobile phase: cyclohexane/ethyl acetate 10:1→4:1→1:1). 17.85 g (40.43 mol, 28% of theory) of a colorless solid are obtained.

$^1$H-NMR (400 MHz, DMSO-d$_6$, δ/ppm): 7.77 (2H, d), 7.42 (2H, d), 5.97-5.82 (2H, m), 5.37-5.18 (4H, m), 4.60 (4H, d), 4.04 (2H, q), 2.59-2.45 (2H, m), 2.30 (2H, t), 2.14-2.02 (2H, m), 1.96-1.83 (2H, m), 1.60-1.47 (2H, m), 1.24-1.07 (5H, m).

MS (DCI): 459 (M+NH$_4^+$).

Example 56A

2-[2-(4-Cyanophenyl)ethyl]heptandioc acid 7-ethyl ester

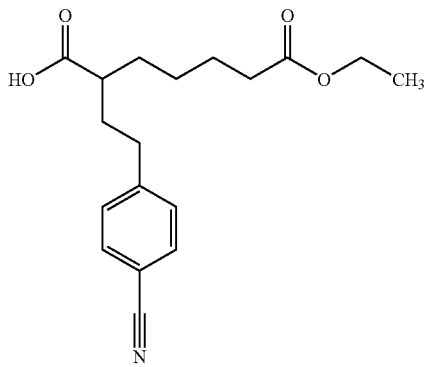

A solution of 18.6 ml (133.4 mmol) of triethylamine and 3.81 ml (101.1 mmol) of formic acid in 175 ml of dioxane is added to a solution of 21 g (40.43 mmol) of 1-allyl 7-ethyl 2-allyloxycarbonyl-2-[2-(4-cyanophenyl)ethyl]heptanedioate, 742 mg (2.83 mmol) of triphenylphosphine and 181 mg (0.81 mmol) of palladium acetate in 175 ml of dioxane at room temperature. The reaction mixture is then stirred at 100° C. for 12 hours. After conversion is complete, the reaction solution is cooled and the solvent is removed in vacuo. The residue is taken up in ethyl acetate and water and acidified with 1 N hydrochloric acid, and the organic phase is separated off. The aqueous phase is extracted three more times with ethyl acetate, and the organic phases are then combined, washed with saturated sodium chloride solution and dried over sodium sulfate. After filtration, the solution is concentrated in vacuo. The resulting crude product is purified by flash chromatography on silica gel (mobile phase: cyclohexane/ethyl acetate 4:1→1:1). 8.6 g (64% of theory) of a colorless solid are obtained.

$^1$H-NMR (400 MHz, DMSO-d$_6$, δ/ppm): 12.25-12.09 (1H, broad), 7.76 (2H, d), 7.40 (2H, d), 4.04 (2H, q), 2.71-2.57 (2H, m), 2.30-2.14 (4H, m), 1.87-1.74 (1H, m), 1.73 (1H, m), 1.58-1.38 (3H, m), 1.31-1.19 (2H, m), 1.18 (3H, t).

MS (EI): 316 (M-H$^-$).

Example 57A

Ethyl 8-(4-cyanophenyl)-6-hydroxymethyloctanoate

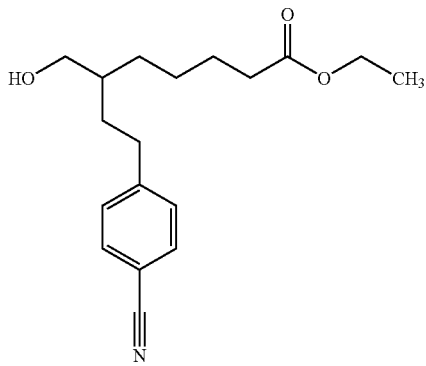

54.19 ml (54.19 mmol) of a 1 M borane-THF complex solution are added dropwise to a solution of 8.6 g (27.1 mmol) of 2-[2-(4-cyanophenyl)ethyl]heptanedioic acid 7-ethyl ester in 200 ml of THF at −10° C. After warming to 0° C., the mixture is stirred at this temperature for 2 hours. After reaction is complete, saturated sodium bicarbonate solution is added to the reaction mixture, and the solvent is concentrated to dryness. The residue is taken up in dichloromethane, dried over sodium sulfate and again freed of solvent. The resulting crude product is purified by flash chromatography on silica gel (mobile phase: ethyl acetate/cyclohexane 1:10→1:4). 5.1 g (97%, 60% of theory) of a colorless solid are obtained.

$^1$H-NMR (300 MHz, DMSO-$d_6$, δ/ppm): 7.74 (2H, d), 7.41 (2H, d), 4.41 (1H, t), 4.03 (2H, q), 3.41-3.29 (2H, m), 2.67 (2H, t), 2.28 (2H, t), 1.69-1.11 (9H, m), 1.18 (3H, t).

MS (DCI): 321 (M+NH$_4^+$).

Example 58A

Ethyl 8-(4-cyanophenyl)-6-formyloctanoate

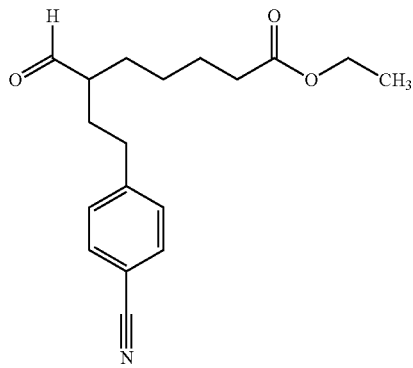

A solution of 4 g (13.18 mmol) of ethyl 8-(4-cyanophenyl)-6-hydroxymethyloctanoate in 100 ml of dichloromethane is mixed with 3.41 g (15.82 mmol) of pyridinium chlorochromate (PCC) and stirred at room temperature for 12 hours. After conversion is complete, the solvent is concentrated to dryness in vacuo. The resulting residue is purified by flash chromatography on silica gel (mobile phase: cyclohexane/ethyl acetate 10:1→4:1). 2.74 g (9.09 mmol, 69% of theory) of a colorless solid are obtained.

LC-MS (method 2): R$_t$ 2.38 min; m/z 302 (M+H$^+$).

Example 59A

Ethyl E-6-[2-(4-cyanophenyl)ethyl]-8-(2-hydroxyphenyl)oct-7-enoate

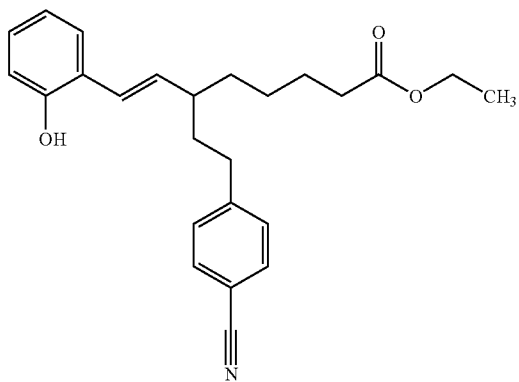

5.91 ml (9.45 mmol) of a 1.6 M solution of n-butyllithium in hexane are slowly added to a solution of 1820 mg (4.05 mmol) of (2-hydroxybenzyl)triphenylphosphonium bromide in 15 ml of anhydrous THF at 0° C. Then, at this temperature, a solution of 1085 mg (3.38 mmol) of ethyl 8-(4-cyanophenyl)-6-formyloctanoate in 15 ml of THF is slowly metered in. After the reaction solution has been warmed to room temperature it is stirred for 12 hours and, after addition of some water, concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 4:1→2:1). 1150 mg (2.79 mmol, 83% of theory) of a colorless solid are obtained.

$^1$H-NMR (400 MHz, DMSO-$d_6$, δ/ppm): 9.48 (1H, s), 7.73 (2H, d), 7.42 (2H, d), 7.38 (1H, d), 7.03 (1H, t), 6.80 (1H, d), 6.74 (1H, t), 6.57 (1H, d), 6.06-5.93 (1H, m), 4.03 (2H, q), 2.76-2.57 (2H, m), 2.26 (2H, t), 2.17-2.02 (1H, m), 1.80-1.68 (1H, m), 1.67-1.56 (1H, m), 1.56-1.39 (3H, m), 1.38-1.19 (3H, m), 1.13 (3H, t).

MS (DCI): 409 (M+NH$_4^+$).

Example 60A

Ethyl E-8-[2-(4-tert-butylbenzyloxy)phenyl]-6-[2-(4-cyanophenyl)ethyl]oct-7-enoate

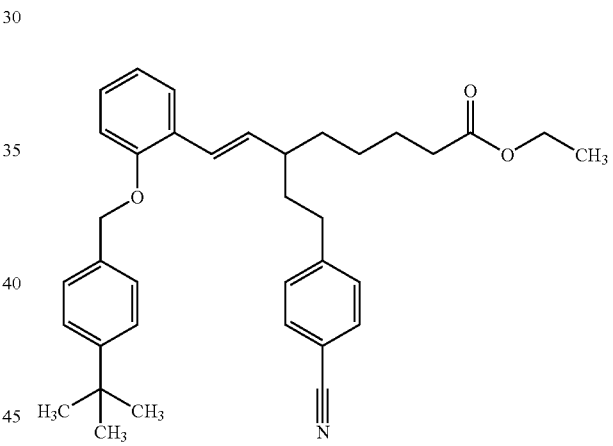

A solution of 2300 mg (5.87 mmol) of ethyl E-6-[2-(4-cyanophenyl)ethyl]-8-(2-hydroxyphenyl)oct-7-enoate in 160 ml of dry acetonitrile is mixed with 1600 mg (7.05 mmol) of 4-(tert-butyl)benzyl bromide and 1220 mg (8.81 mmol) of anhydrous potassium carbonate and heated under reflux for 12 hours. The mixture is then concentrated to dryness. The residue is taken up in ethyl acetate, washed with water and saturated sodium chloride solution, dried over sodium sulfate and the organic phase concentrated. The resulting crude product is purified by flash chromatography an silica gel (mobile phase: cyclohexane/ethyl acetate 10:1). 2800 mg (5.21 mmol, 88% of theory) of a solid are obtained.

$^1$H-NMR (300 MHz, DMSO-$d_6$, δ/ppm): 7.68 (2H, d), 7.45 (1H, d), 7.41-7.32 (6H, m), 7.20 (1H, t), 7.09 (1H, d), 6.91 (1H, t), 6.61 (1H, d), 6.08-5.95 (1H, m), 5.10 (2H, s), 4.00 (2H, q), 2.77-2.45 (3H, m), 2.23 (2H, t), 2.12-1.98 (1H, m), 1.78-1.37 (5H, m), 1.32-1.19 (2H, m), 1.28 (9H, s), 1.13 (3H, t).

MS (DCI): 555 (M+NH$_4^+$).

Example 61A

Ethyl (7E)-8-{2-[(4-tert-butylbenzyl)oxy]phenyl}-6-{2-[4-(1H-tetrazol-5-yl)phenyl]ethyl}oct-7-enoate

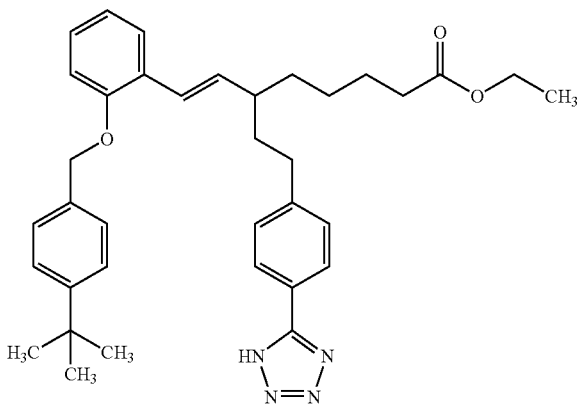

A solution of 1 g (1.86 mmol) of ethyl (7E)-8-{2-[(4-tert-butylbenzyl)oxy]phenyl}-6-[2-(4-cyanophenyl)ethyl]-oct-7-enoate in 70 ml of toluene is mixed with 3.7 ml (27.9 mmol) of trimethylsilyl azide and 694 mg (2.79 mmol) of di-n-butyltin oxide and heated at 80° C. for 12 hours. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by flash chromatography on silica gel (mobile phase: cyclohexane/ethyl acetate 4:1→1:1). 622 mg (1.1 mmol, 34% of theory) of a white foam are obtained.

$^1$H-NMR (300 MHz, DMSO-$d_6$, δ/ppm): 7.90 (2H, d), 7.48 (1H, d), 7.40-7.30 (6H, m), 7.22-7.10 (1H, m), 7.09 (1H, d), 6.90 (1H, t), 6.55 (1H, d), 6.06 (1H, dd), 5.10 (2H, s), 4.00 (2H, q), 2.77-2.52 (2H, m), 2.30-2.00 (2H, m), 1.80-1.38 (9H, m), 1.20 (9H, s), 1.10 (3H, t).

Example 62A

Ethyl (7E)-6-[2-(4-cyanophenyl)ethyl]-8-{2-[(5-phenylpentyl)oxy]phenyl}oct-7-enoate

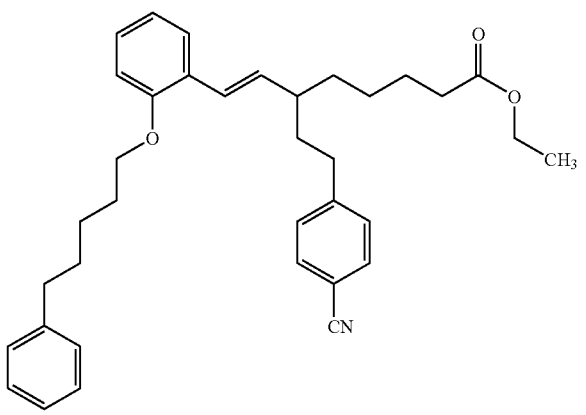

A solution of 127 mg (0.32 mmol) of ethyl (7E)-6-[2-(4-cyanophenyl)ethyl]-8-(2-hydroxyphenyl)oct-7-enoate in 10 ml of acetonitrile is mixed with 88.42 mg (0.39 mmol) of (5-bromopentyl)benzene and 67.25 mg (0.49 mmol) of potassium carbonate and stirred under reflux for 12 hours. After cooling, the mixture is concentrated. The residue is taken up in ethyl acetate and extracted with water. The organic phase is washed with saturated sodium chloride solution, dried over sodium sulfate and concentrated. The resulting residue is purified by preparative HPLC. 128 mg (0.24 mmol, 73.4% of theory) of the title compound are obtained.

LC-MS (method 2): $R_t$=3.42 min.
MS (ESIpos): m/z=538 (M+H)$^+$.

Example 63A

Ethyl (7E)-8-{2-[(5-phenylpentyl)oxy]phenyl}-6-{2-[4-(1H-tetrazol-5-yl)phenyl]ethyl}oct-7-enoate

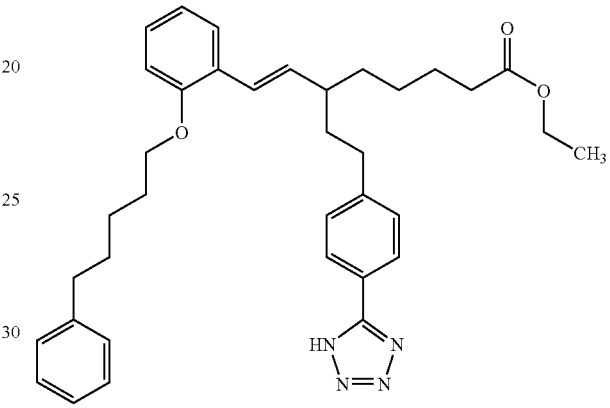

A solution of 128 mg (0.24 mmol) of ethyl (7E)-6-[2-(4-cyanophenyl)ethyl]-8-{2-[(5-phenylpentyl)oxy]phenyl}oct-7-enoate in 10 ml of toluene is mixed with 0.47 ml (3.57 mmol) of trimethylsilyl azide and 88.9 mg (0.36 mmol) of di-n-butyltin oxide and heated at 80° C. for 12 hours. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by preparative HPLC. 62 mg (0.11 mmol, 44.8% of theory) of a colorless foam are obtained.

LC-MS (method 2): $R_t$=3.23 min.
MS (ESIpos): m/z=581 (M+H)$^+$.

Example 64A

1-Allyl 7-ethyl 2-allyloxycarbonyl-2-(4-cyanobenzyl)heptanedioate

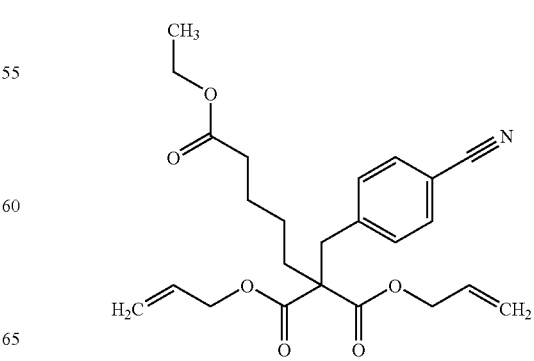

1.69 g (70.43 mmol) of sodium hydride are added in portions to a solution of 20 g (64.03 mmol) of 1-allyl 7-ethyl 2-allyloxycarbonylheptanedioate in 140 ml of DMF at 0° C. The reaction mixture is then allowed to reach room temperature and is stirred for 30 min. The reaction solution is cooled to 0° C. again and, after addition of 16.32 g (83.24 mmol) of 4-bromomethylbenzonitrile in 140 ml of DMF, stirred at this temperature for 30 min. The mixture is then stirred at room temperature overnight. Water is added dropwise to the reaction mixture and, after extraction three times with ethyl acetate, the combined organic phases are washed with saturated sodium chloride solution and dried over sodium sulfate. After filtration, the solvent is concentrated to dryness in vacuo. The resulting crude product is purified by flash chromatography an silica gel (mobile phase: cyclohexane/ethyl acetate 10:1→4:1→1:1). 20.08 g (46.97 mmol, 73% of theory) of a colorless solid are obtained.

$^1$H-NMR (400 MHz, CDCl$_3$, δ/ppm): 7.56 (2H, d), 7.22 (2H, d), 5.91-5.78 (2H, m), 5.37-5.18 (4H, m), 4.66-4.54 (4H, m), 4.13 (2H, q), 3.29 (2H, s), 2.31 (2H, t), 1.87-1.77 (2H, m), 1.69-1.57 (2H, m), 1.39-1.28 (2H, m), 1.26 (3H, t).

MS (DCI): 445 (M+NH$_4$$^+$).

Example 65A 2-(4-Cyanobenzyl)-heptanedioic acid 7-ethyl ester

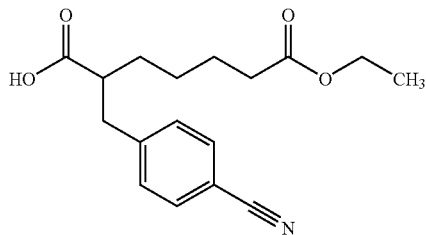

A solution of 24.21 ml (173.69 mmol) of triethylamine and 4.96 ml (131.58 mmol) of formic acid in 500 ml of dioxane is added to a solution of 22.5 g (52.63 mmol) of 1-allyl 7-ethyl 2-allyloxycarbonyl-2-(4-cyanobenzyl)-heptanedioate, 970 mg (3.68 mmol) of triphenylphosphine and 240 mg (1.05 mmol) of palladium acetate in 500 ml of dioxane at room temperature. The reaction mixture is then stirred at 100° C. for 2 hours. After conversion is complete, the reaction solution is cooled, and the solvent is removed in vacuo. The residue is taken up in ethyl acetate and water and acidified with 1 N hydrochloric acid, and the organic phase is separated off. The aqueous phase is extracted three times more with ethyl acetate, and the organic phases are then combined, washed with saturated sodium chloride solution and dried over sodium sulfate. After filtration, the solution is concentrated in vacuo. 17.5 g (87% of theory, 80% purity) of a colorless solid are obtained.

LC-MS (method 2): R$_t$=1.97 min; m/z=304 (M+H$^+$).

Example 66A

Ethyl 6-(4-cyanobenzyl)-7-hydroxyheptanoate

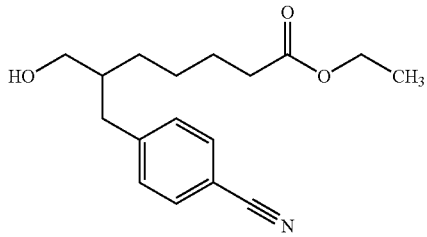

34.42 ml of a 1 M borane-THF complex solution (34.42 mmol) are added dropwise to a solution of 6.64 g (22.94 mmol) of 2-(4-cyanobenzyl)heptanedioic acid 7-ethyl ester in 260 ml of THF at −10° C. After warming to 0° C., the mixture is stirred at this temperature for 2 hours. After the reaction is complete, saturated sodium bicarbonate solution is added to the reaction mixture, and the solvent is concentrated to dryness. The residue is taken up in dichloromethane, dried over sodium sulfate and again freed of solvent. The resulting crude product is purified by flash chromatography on silica gel (mobile phase: ethyl acetate/cyclohexane 1:8→1:2). 5.84 g (88% of theory, 20.19 mmol) of a colorless solid are obtained.

$^1$H-NMR (400 MHz, DMSO-d$_6$, δ/ppm): 8.14 (2H, d), 7.80 (2H, d), 4.91 (1H, t), 4.44 (2H, q), 3.69-3.58 (2H, m), 3.16-3.06 (1H, m), 3.01-2.92 (1H, m), 2.62 (2H, t), 2.14-2.01 (1H, m), 1.92-1.78 (2H, m), 1.77-1.60 (3H, m), 1.59-1.48 (1H, m), 1.57 (3H, t).

MS (DCI): 307 (M+NH$_4$$^+$).

Example 67A

Ethyl 6-(4-cyanobenzyl)-7-oxoheptanoate

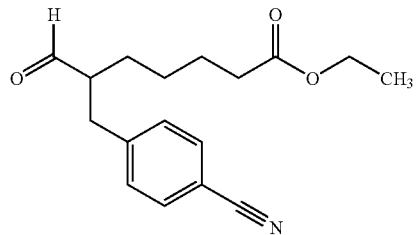

A solution of 4.6 g (15.90 mmol) of ethyl 6-(4-cyanobenzyl)-7-hydroxyheptanoate in 250 ml of dichloromethane is mixed with 4.11 g (19.08 mmol) of pyridinium chlorochromate (PCC) and stirred at room temperature for 12 hours. After conversion is complete, 10 g of silica gel are added, and the solvent is cautiously concentrated to dryness in vacuo. The resulting residue is purified by flash chromatography on silica gel (mobile phase: cyclohexane/ethyl acetate 1:1). 4.09 g (14.23 mmol, 89% of theory) of a colorless solid are obtained.

$^1$H-NMR (400 MHz, DMSO-d$_6$, δ/ppm): 9.60 (1H, s), 7.75 (2H, d), 7.41 (2H, d), 4.03 (2H, q), 3.08-2.97 (1H, m), 2.82-2.64 (2H, m), 2.24 (2H, t), 1.63-1.19 (6H, m), 1.17 (3H, t).

MS (DCI): 305 (M+NH$_4$$^+$).

Example 68A

Ethyl E-6-(4-cyanobenzyl)-8-(2-hydroxyphenyl)oct-7-enoate

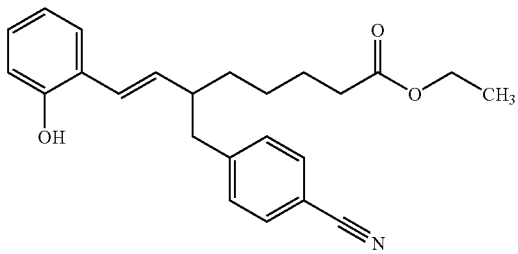

15.98 ml (39.95 mmol) of a 2.5 M solution of n-butyllithium in hexane are slowly added to a solution of 6.411 g (14.27 mmol) of (2-hydroxybenzyl)triphenylphosphonium bromide in 300 ml of anhydrous THF at 0° C. Then, at this temperature, 4.1 g (14.27 mmol) of ethyl 6-(4-cyanobenzyl)-7-oxoheptanoate are slowly metered in. After warming to room temperature, the reaction solution is stirred for 12 hours and then mixed with saturated ammonium chloride solution and concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 4:1). 1.75 g (4.64 mmol, 32% of theory) of a colorless solid are obtained.

$^1$H-NMR (400 MHz, DMSO-$d_6$, δ/ppm): 9.42 (1H, s), 7.72 (2H, d), 7.40 (2H, d), 7.29 (1H, d), 7.00 (1H, t), 6.79-6.67 (2H, m), 6.39 (1H, d), 6.04-5.94 (1H, m), 4.01 (2H, q), 2.87-2.77 (1H, m), 2.76-2.66 (1H, m), 2.48-2.38 (1H, m), 2.25 (2H, t), 1.57-1.39 (3H, m), 1.38-1.19 (3H, m), 1.13 (3H, t).
MS (DCI): 395 (M+NH$_4^+$).

Example 69A

Ethyl E-8-[2-(4-tert-butylbenzyloxy)phenyl]-6-(4-cyanobenzyl)oct-7-enoate

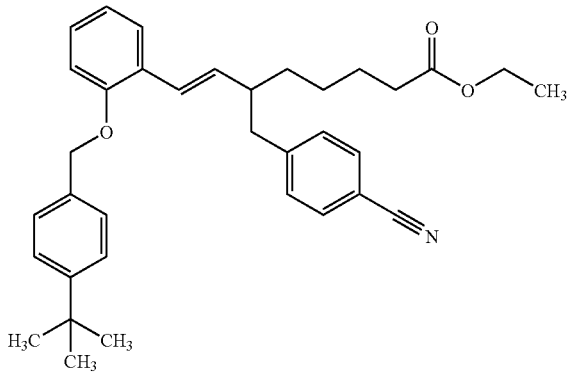

A solution of 1.75 g (4.64 mmol) of ethyl E-6-(4-cyanobenzyl)-8-(2-hydroxyphenyl)oct-7-enoate in 50 ml of dry acetonitrile is mixed with 1579 mg (6.95 mmol) of 4-(tert-butyl)benzyl bromide and 961 mg (6.95 mmol) of anhydrous potassium carbonate and heated under reflux for 12 hours. The mixture is then concentrated to dryness. The residue is taken up in ethyl acetate, washed with water and saturated sodium chloride solution and dried over sodium sulfate. The organic phase is concentrated. The resulting crude product is purified by flash chromatography on silica gel (mobile phase: cyclohexane/ethyl acetate 8:1→4:1). 2.24 g (4.28 mmol, 92% of theory) of a solid are obtained.

$^1$H-NMR (300 MHz, DMSO-$d_6$, δ/ppm): 7.68 (2H, d), 7.44-7.32 (5H, m), 7.28 (2H, d), 7.14 (1H, t), 7.01 (1H, d), 6.88 (1H, t), 6.42 (1H, d), 6.08-5.95 (1H, m), 5.04 (2H, s), 4.00 (2H, q), 2.89-2.78 (1H, m), 2.75-2.60 (2H, m), 2.54-2.40 (1H, m), 2.23 (2H, t), 1.60-1.21 (5H, m), 1.28 (9H, s), 1.13 (3H, t).
MS (DCI): 541 (M+NH$_4^+$).

Example 70A

Ethyl (7E)-8-{2-[(4-tert-butylbenzyl)oxy]phenyl}-6-[4-(1H-tetrazol-5-yl)benzyl]oct-7-enoate

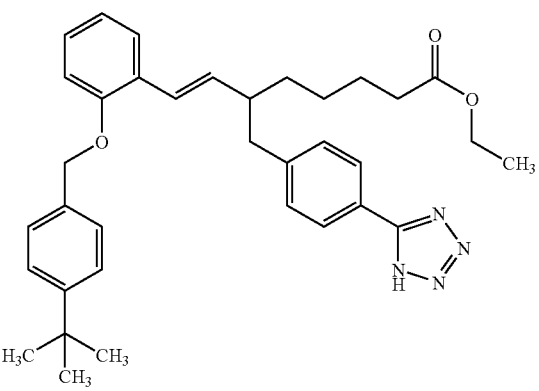

A solution of 1000 mg (1.91 mmol) of ethyl (7E)-8-{2-[(4-tert-butylbenzyl)oxy]phenyl}-6-(4-cyanobenzyl)oct-7-enoate in 70 ml of toluene is mixed with 3.8 ml (28.6 mmol) of trimethylsilyl azide and 713 mg (2.86 mmol) of di-n-butyltin oxide and heated at 80° C. for 12 hours. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by flash chromatography on silica gel (mobile phase: dichloromethane→dichloromethane/methanol 10:1). 800 mg (1.4 mmol, 74% of theory) of a white foam are obtained.
MS (DCI): m/z=541 (M+NH$_4$)$^+$.

Example 71A

Ethyl (7E/Z)-6-(4-cyanobenzyl)-8-{2-[(5-phenylpentyl)oxy]phenyl}oct-7-enoate

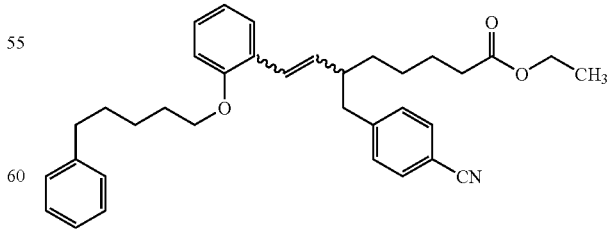

2.13 ml (3.42 mmol) of a 1.6 M solution of n-butyllithium in hexane are slowly added to a solution of 1695 mg (2.85 mmol) of triphenyl-{2-[(5-phenylpentyl)oxy]benzyl}phosphonium bromide in 15 ml of THF at 0° C. Then, at this temperature, 818 mg (2.85 mmol) of ethyl 6-(4-cyanobenzyl)-7-oxoheptanoate in 15 ml of THF are slowly metered in. After warming to room temperature, the reaction solution is stirred for 12 hours and then mixed with some water and concentrated to dryness. The residue is taken up in ethyl acetate, washed with water and saturated sodium chloride solution and dried over sodium sulfate. After filtration, the solvent is concentrated to dryness. The resulting crude product is purified by flash chromatography on silica gel (mobile phase: cyclohexane/ethyl acetate 50:1→20:1). 730 mg (1.4 mmol, 48% of theory) of a white foam are obtained.

MS (DCI): m/z=541 (M+NH$_4$)$^+$.

Example 72A

Ethyl (7E/Z)-8-{2-[(5-phenylpentyl)oxy]phenyl}-6-[4-(1H-tetrazol-5-yl)benzyl]oct-7-enoate

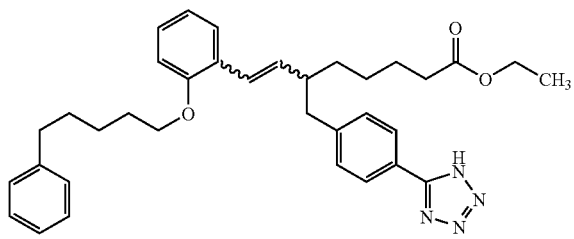

A solution of 100 mg (0.19 mmol) of ethyl (7E/Z)-6-(4-cyanobenzyl)-8-{2-[(5-phenylpentyl)oxy]-phenyl}oct-7-enoate in 10 ml of toluene is mixed with 0.05 ml (0.38 mmol) of trimethylsilyl azide and 4.75 mg (0.02 mmol) of di-n-butyltin oxide and heated at 80° C. for 12 hours. After cooling to room temperature, the mixture is washed with saturated sodium bicarbonate solution. The organic phase is separated off, washed with saturated sodium chloride solution and dried over sodium sulfate. After filtration, the filtrate is concentrated to dryness. The resulting crude product is purified by preparative HPLC. 19 mg (0.03 mmol, 16.9% of theory) of a colorless foam are obtained.

MS (ESIpos): m/z=584 (M+NH$_4$)$^+$.

EXEMPLARY EMBODIMENTS

Example 1

4-((3E)-4-{2-[(4-tert-Butyl-2-chlorobenzyl)oxy]phenyl}-2-{2-[4-(1H-tetrazol-5-yl)phenyl]ethyl}but-3-en-1-yl)benzoic acid

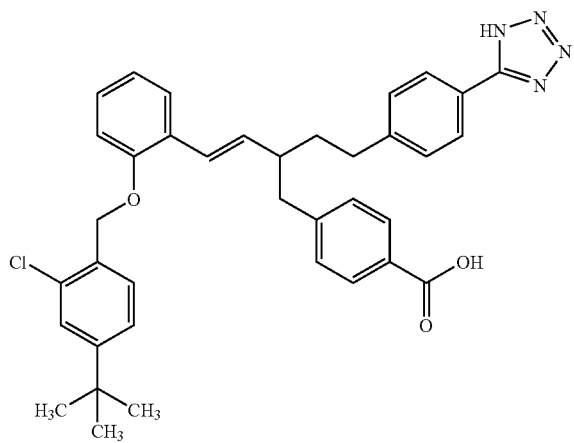

A solution of 500 mg (0.79 mmol) of methyl 4-((3E)-4-{2-[(4-tert-butyl-2-chlorobenzyl)oxy]phenyl}-2-{2-[4-(1H-tetrazol-5-yl)phenyl]ethyl}but-3-en-1-yl)benzoate in 3 ml of THF and 1.5 ml of water is mixed with 75.4 mg (3.15 mmol) of lithium hydroxide and stirred at 60° C. for 12 h. After cooling, the THF is stripped off and the aqueous phase is adjusted to pH 2 with 1 M hydrochloric acid. It is then extracted three times with ethyl acetate, and the combined organic phases are dried over sodium sulfate. The residue obtained after filtration and concentration is purified by chromatography on a silica gel column (mobile phase:ethyl acetate/cyclohexane 1:1). 372 mg (0.6 mmol, 76% of theory) of a white foam are obtained.

$^1$H-NMR (300 MHz, DMSO-d$_6$, δ/ppm): 12.76 (1H, broad), 7.9 (2H, d), 7.79 (2H, d), 7.48-7.15 (9H, m), 7.06 (1H, d), 6.93 (1H, t), 6.49 (1H, d), 6.12 (1H, dd), 5.11 (2H, s), 2.91-2.8 (1H, m), 2.79-2.57 (3H, m), 2.57-2.42 (1H, m), 1.88-1.58 (2H, m), 1.38 (9H, s).

350 mg (0.56 mmol) of 4-((3E)-4-{2-[(4-tert-butyl-2-chlorobenzyl)oxy]phenyl}-2-{2-[4-(1H-tetrazol-5-yl)phenyl]ethyl}but-3-en-1-yl)benzoic acid are further fractionated by preparative HPLC on a chiral phase. Respectively 156 mg and 132 mg of the two E isomers, each enantiopure, are obtained as colorless solids (see Examples 2 and 3).

Example 2

4-((3E)-4-{2-[(4-tert-Butyl-2-chlorobenzyl)oxy]phenyl}-2-{2-[4-(1H-tetrazol-5-yl)phenyl]ethyl}but-3-en-1-yl)benzoic acid (enantiomer 1)

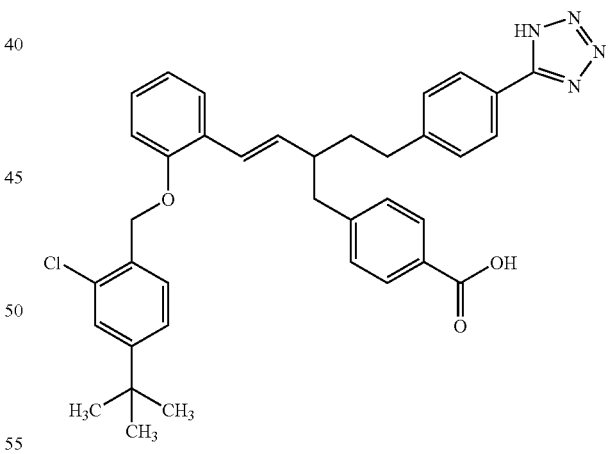

Enantiomer Separation Method:

Column: Daicel Chiralpak AD-H 250×20 mm; eluent: isohexane (with 1% water and 0.2% acetic acid)/isopropanol 70:30 (v/v); flow rate: 15 ml/min; UV detection: 220 nm; temperature: 27° C.

R$_t$ 6.73 min; purity 99%; >99% ee

Yield: 156 mg.

Example 3

4-((3E)-4-{2-[(4-tert-Butyl-2-chlorobenzyl)oxy]phenyl}-2-{2-[4-(1H-tetrazol-5-yl)phenyl]ethyl}but-3-en-1-yl)benzoic acid (enantiomer 2)

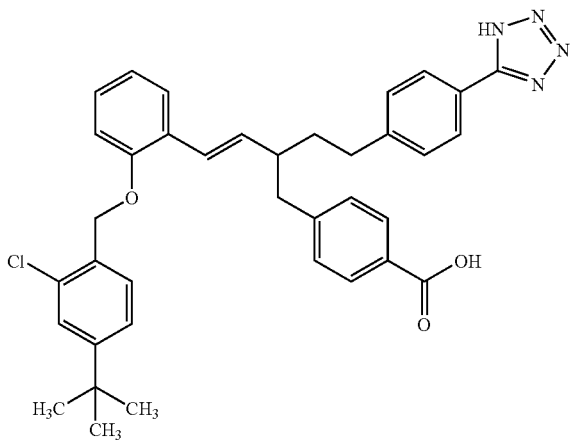

Enantiomer separation method: see Example 2.
R, 7.4 min; purity 99%; >99% ee
Yield: 132 mg.

Example 4

4-((3E)-4-{2-[(4-tert-Butylbenzyl)oxy]phenyl}-2-{2-[4-(1H-tetrazol-5-yl)phenyl]ethyl}but-3-en-1-yl)benzoic acid

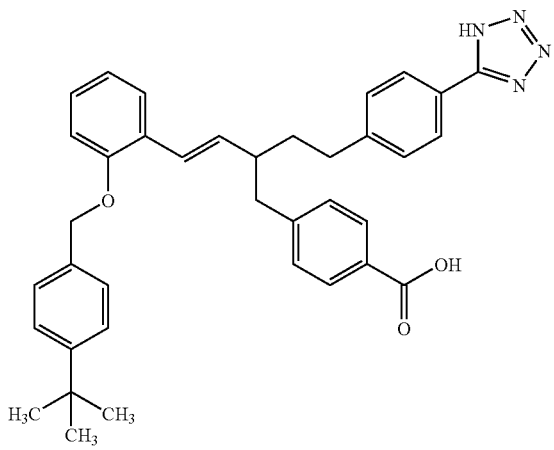

A solution of 150 mg (0.25 mmol) of 4-((3E)-4-{2-[(4-tert-butylbenzyl)oxy]phenyl}-2-{2-[4-(1H-tetrazol-5-yl)phenyl]ethyl}but-3-en-1-yl)benzoate in 1.5 ml of THF and 0.75 ml of water is mixed with 24 mg (1 mmol) of lithium hydroxide and stirred at 60° C. for 12 h. After cooling, the THF is stripped off and the aqueous phase is adjusted to pH 2 with 1 M hydrochloric acid. It is then extracted three times with ethyl acetate, and the combined organic phases are dried over sodium sulfate. The residue obtained after filtration and concentration is purified by chromatography on a silica gel column (mobile phase: cyclohexane/ethyl acetate 2.5:1). 108 mg (0.18 mmol, 68.6% of theory) of a white foam are obtained.

$^1$H-NMR (400 MHz, DMSO-$d_6$, δ/ppm): 12.75 (1H, broad), 7.91 (2H, d), 7.81 (2H, d), 7.45-7.25 (9H, m), 7.21-7.13 (1H, m), 7.02 (1H, d), 6.89 (1H, t), 6.5 (1H, d), 6.13 (1H, dd), 5.05 (2H, s), 2.92-2.83 (1H, m), 2.8-2.53 (4H, m), 1.9-1.76 (1H, m), 1.76-1.62 (1H, m), 1.23 (9H, s).

880 mg (1.5 mmol) of 4-((3E)-4-{2-[(4-tert-butylbenzyl)oxy]phenyl}-2-{2-[4-(1H-tetrazol-5-yl)phenyl]ethyl}but-3-en-1-yl)benzoic acid are further fractionated by preparative HPLC on a chiral phase. Respectively 208 mg and 236 mg of the two E isomers, each enantiopure, are obtained as colorless solids (see Examples 5 and 6).

Example 5

4-((3E)-4-{2-[(4-tert-Butylbenzyl)oxy]phenyl}-2-{2-[4-(1H-tetrazol-5-yl)phenyl]ethyl}but-3-en-1-yl)benzoic acid (enantiomer 1)

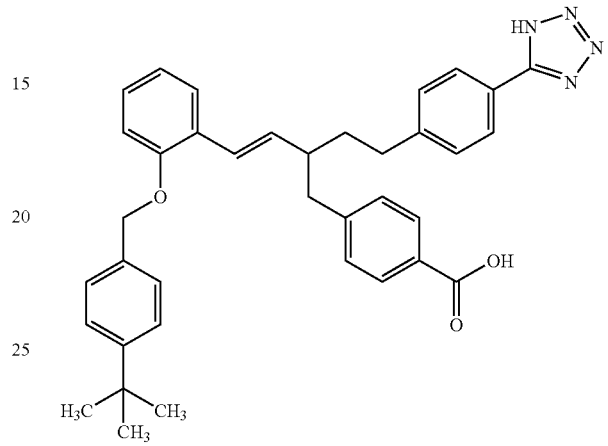

Enantiomer Separation Method:
Column: Daicel Chiralpak AD-H 250×20 mm; eluent: isohexane (with 1% water and 1% acetic acid)/isopropanol 70:30 (v/v); flow rate: 15 ml/min; UV detection: 215 nm; temperature: 25° C.
R, 8.27 min; purity 99%; >99% ee
Yield: 208 mg.

Example 6

4-((3E)-4-{2-[(4-tert-Butylbenzyl)oxy]phenyl}-2-{2-[4-(1H-tetrazol-5-yl)phenyl]ethyl}but-3-en-1-yl)benzoic acid (Enantiomer 2)

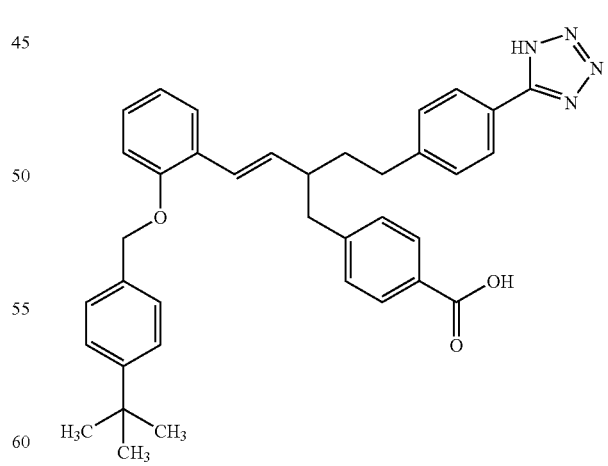

Enantiomer Separation Method: See Example 5.
R, 9.16 min; purity 99%; >98% ee
Yield: 236 mg
LC-MS (method 1): R$_t$=3.11 min.
MS (ESIneg): m/z=585 (M−H)$^-$.

Example 7

4-((3E)-4-{2-[(2-Chlorobenzyl)oxy]phenyl}-2-{2-[4-(1H-tetrazol-5-yl)phenyl]ethyl}but-3-en-1-yl) benzoic acid

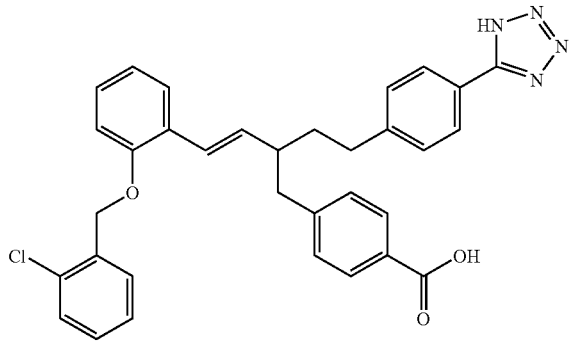

A solution of 95 mg (0.16 mmol) of methyl 4-((3E)-4-{2-[(2-chlorobenzyl)oxy]phenyl}-2-{2-[4-(1H-tetrazol-5-yl)phenyl]ethyl}but-3-en-1-yl)benzoate in 1 ml of THF and 0.5 ml of water is mixed with 15.7 mg (0.66 mmol) of lithium hydroxide and stirred at 60° C. for 12 h. After cooling, the THF is stripped off and the aqueous phase is adjusted to pH 2 with 1 M hydrochloric acid. It is then extracted three times with ethyl acetate, and the combined organic phases are dried over sodium sulfate. The residue obtained after filtration and concentration is purified chromatographically over a silica gel column (mobile phase: dichloromethane/methanol 10:1). 42.6 g (0.08 mmol, 41.4% of theory) of a white foam are obtained.

$^1$H-NMR (300 MHz, DMSO-$d_6$, δ/ppm): 12.75 (1H, broad), 7.9 (2H, d), 7.8 (2H, d), 7.55-7.48 (2H, m), 7.44 (1H, d), 7.4-7.3 (5H, m), 7.29-7.17 (2H, m), 7.06 (1H, d), 6.94 (1H, t), 6.5 (1H, d), 6.12 (1H, dd), 5.16 (2H, s), 2.9-2.8 (1H, m), 2.82-2.58 (3H, m), 2.58-2.42 (1H, m), 1.88-1.59 (2H, m).

85 mg (0.15 mmol) of 4-((3E)-4-{2-[(2-chlorobenzyl)oxy]phenyl}-2-{2-[4-(1H-tetrazol-5-yl)phenyl]ethyl}but-3-en-1-yl)benzoic acid are further fractionated by preparative HPLC on a chiral phase. Respectively 39.1 mg and 38.4 mg of the two E isomers, each enantiopure, are obtained as colorless solids (see Examples 8 and 9).

Example 8

4-((3E)-4-{2-[(2-Chlorobenzyl)oxy]phenyl}-2-{2-[4-(1H-tetrazol-5-yl)phenyl]ethyl}but-3-en-1-yl) benzoic acid (Enantiomer 1)

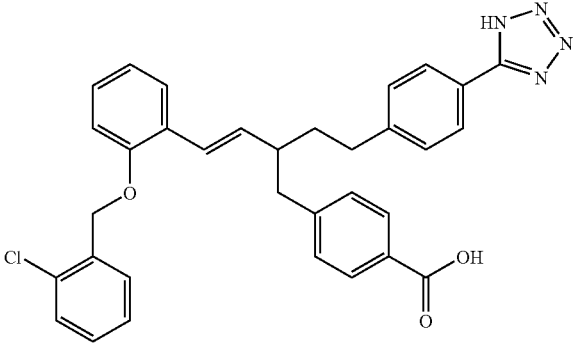

Enantiomer Separation Method:
Column: Daicel Chiralpak AD-H 250×20 mm; eluent: isohexane (with 1% water and 0.2% trifluoroacetic acid)/ethanol 85:15 (v/v); flow rate: 15 ml/min; UV detection: 220 nm; temperature: 30° C.
$R_t$ 20.47 min.
Yield: 39.1 mg
LC-MS (method 3): $R_t$=2.97 min.
MS (ESIpos): m/z=565 (M+H)$^+$.

Example 9

4-((3E)-4-{2-[(2-chlorobenzyl)oxy]phenyl}-2-{2-[4-(1H-tetrazol-5-yl)phenyl]ethyl}but-3-en-1-yl)benzoic acid (Enantiomer 2)

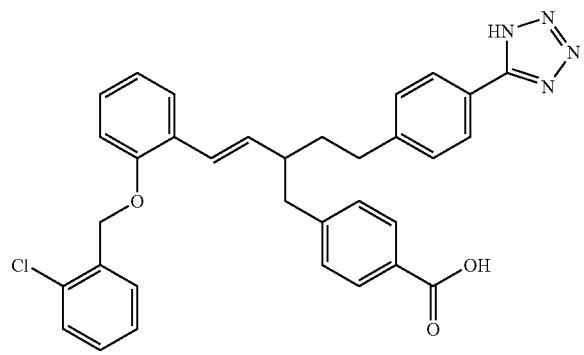

Enantiomer Separation Method: See Example 8.
$R_t$ 23.38 min.
Yield: 38.4 mg

Example 10

4-[(3E)-2-{2-[4-(1H-Tetrazol-5-yl)phenyl]ethyl}-4-(2{[2-(trifluoromethyl)benzyl]oxy}phenyl)but-3-en-1-yl)benzoic acid

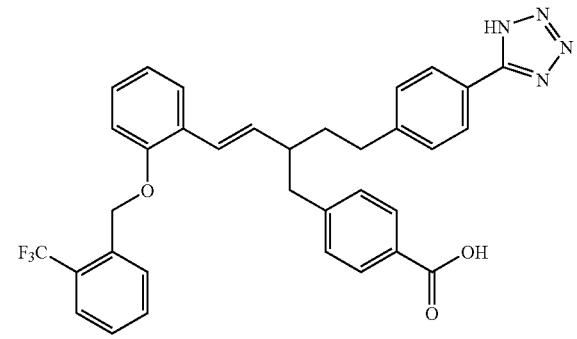

A solution of 120 mg (0.2 mmol) of methyl 4-[(3E)-2-{2-[4-(1H-tetrazol-5-yl)phenyl]ethyl}-4-(2{[2-(trifluoromethyl)benzyl]oxy}phenyl)but-3-en-1-yl)benzoate in 1 ml of THF and 0.5 ml of water is mixed with 18.8 mg (0.78 mmol) of lithium hydroxide and stirred at 60° C. for 12 h. After cooling, the THF is stripped off and the aqueous phase is adjusted to pH 2 with 1 M hydrochloric acid. It is then extracted three times with ethyl acetate, and the combined organic phases are dried over sodium sulfate. The residue obtained after filtration and concentration is purified chromatographically over a silica gel column (mobile phase: cyclohexane/ethyl acetate 3:1→100% ethyl acetate). 109 mg (0.18 mmol, 91.5% of theory) of a white foam are obtained.

1H-NMR (400 MHz, DMSO-d$_6$, δ/ppm): 16.72 (1H, broad), 12.72 (1H, broad), 7.88 (2H, d), 7.8 (3H, d), 7.69-7.62 (2H, m), 7.59-7.52 (1H, m), 7.45 (1H, d), 7.35 (2H, d), 7.26 (1H, d), 7.22-7.16 (1H, m), 6.95 (1H, t), 6.49 (1H, d), 6.1 (1H, dd), 5.22 (2H, s), 2.9-2.8 (1H, m), 2.76-2.65 (2H, m), 2.65-2.55 (1H, m), 1.87-1.72 (1H, m), 1.72-1.58 (1H, m), 1.37-1.2 (1H, m).

90 mg (0.15 mmol) of 4-[(3E)-2-{2-[4-(1H-tetrazol-5-yl)phenyl]ethyl}-4-(2{[2-(trifluoromethyl)benzyl]oxy}phenyl)but-3-en-1-yl)benzoic acid are further fractionated by preparative HPLC on a chiral phase. Respectively 44.3 mg and 41.8 mg of the two E isomers, each enantiopure, are obtained as colorless solids (see Examples 11 and 12).

Example 11

4-[(3E)-2-{2-[4-(1H-Tetrazol-5-yl)phenyl]ethyl}-4-(2-{[2-(trifluoromethyl)benzyl]oxy}phenyl)but-3-en-1-yl]benzoic acid (Enantiomer 1)

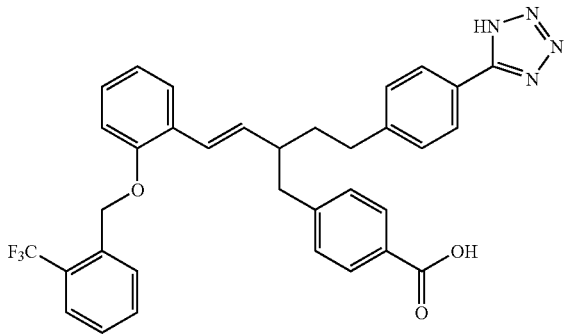

Enantiomer Separation Method:
Column: Daicel Chiralpak AD-H 250×20 mm; eluent: isohexane (with 1% water and 0.2% trifluoroacetic acid)/ethanol 85:15 (v/v); flow rate: 15 ml/min; UV detection: 220 nm; temperature: 30° C.
R$_t$ 13.14 min.
Yield: 44.3 mg
LC-MS (method 3): R$_t$=2.98 min.
MS (ESIpos): m/z=599 (M+H)$^+$.

Example 12

4-[(3E)-2-{2-[4-(1H-Tetrazol-5-yl)phenyl]ethyl}-4-(2-{[2-(trifluoromethyl)benzyl]oxy}phenyl)but-3-en-1-yl]benzoic acid (Enantiomer 2)

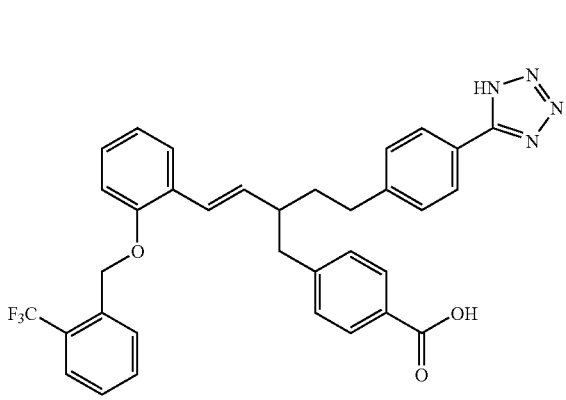

Enantiomer Separation Method: See Example 11.
R$_t$ 14.63 min.
Yield: 41.8 mg

Example 13

4-{(4E)-5-{2-[(5-Phenylpentyl)oxy]phenyl}-3-[4-(1H-tetrazol-5-yl)benzyl]pent-4-en-1-yl}benzoic acid

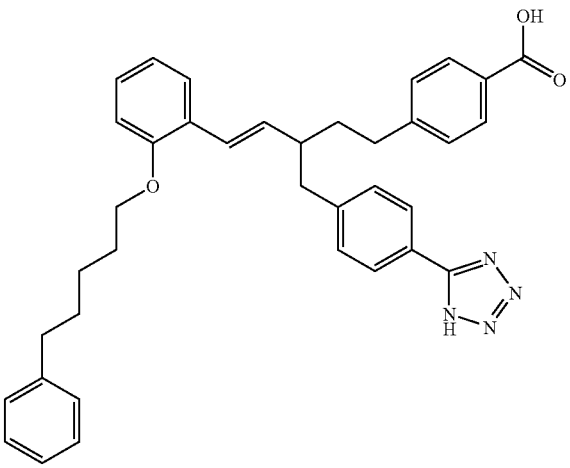

A solution of 284 mg (0.47 mmol) of methyl 4-{(4E)-5-{2-[(5-Phenylpentyl)oxy]phenyl}-3-[4-(1H-tetrazol-5-yl)benzyl]pent-4-en-1-yl}benzoate in 10 ml of THF and 10 ml of water is mixed with 22.6 mg (0.95 mmol) of lithium hydroxide and stirred at 50° C. for 12 h. After cooling, the THF is stripped off and the aqueous phase is adjusted to pH 3 with 1 M hydrochloric acid. It is then extracted three times with ethyl acetate, and the combined organic phases are dried over sodium sulfate. The residue obtained after filtration and concentration is purified by preparative HPLC. 78 mg (0.13 mmol, 26% of theory) of a white foam are obtained.
MS (ESIpos): m/z=587 (M+H)$^+$.

70 mg (0.12 mmol) of 4-{(4E)-5-{2-[(5-phenylpentyl)oxy]phenyl}-3-[4-(1H-tetrazol-5-yl)benzyl]pent-4-en-1-yl}benzoic acid are further fractionated by preparative HPLC on a chiral phase. Respectively 26 mg and 17 mg of the two E isomers, each enantiopure, are obtained as colorless solids (see Examples 14 and 15).

Example 14

4-{(4E)-5-{2-[(5-Phenylpentyl)oxy]phenyl}-3-[4-(1H-tetrazol-5-yl)benzyl]pent-4-en-1-yl}benzoic acid (Enantiomer 1)

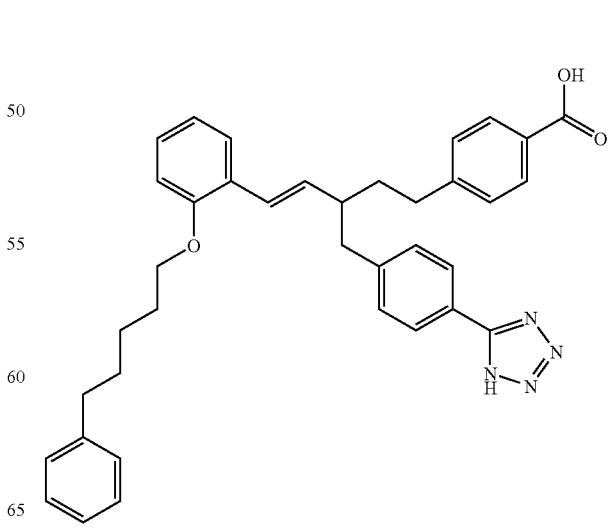

83

Enantiomer Separation Method:

Column: Daicel Chiralpak AD-H 250×20 mm; eluent: isohexane (with 1% water and 0.2% trifluoroacetic acid)/isopropanol 70:30 (v/v); flow rate: 15 ml/min; UV detection: 215 nm; temperature: 25° C.

$R_t$ 6.27 min; purity 98.5%; >99% ee

Yield: 26 mg $^1$H-NMR (300 MHz, DMSO-$d_6$, δ/ppm): 12.77 (1H, broad), 7.91 (2H, d), 7.85 (2H, d), 7.42-7.33 (4H, m), 7.3 (2H, d), 7.26-7.17 (2H, m), 7.17-7.1 (4H, m), 6.95-6.83 (2H, m), 6.44 (1H, d), 6.17-6.05 (1H, m), 3.96-3.82 (2H, m), 2.93-2.82 (1H, m), 2.81-2.69 (2H, m), 2.68-2.56 (2H, m), 1.90-1.76 (1H, m), 1.76-1.62 (3H, m), 1.62-1.48 (2H, m), 1.46-1.28 (2H, m), 1.27-1.19 (1H, s).

LC-MS (method 1): $R_t$=3.20 min.

MS (ESIpos): m/z=587 (M+H)$^+$.

Example 15

4-{(4E)-5-{2-[(5-Phenylpentyl)oxy]phenyl}-3-[4-(1H-tetrazol-5-yl)benzyl]pent-4-en-1-yl}benzoic acid (Enantiomer 2)

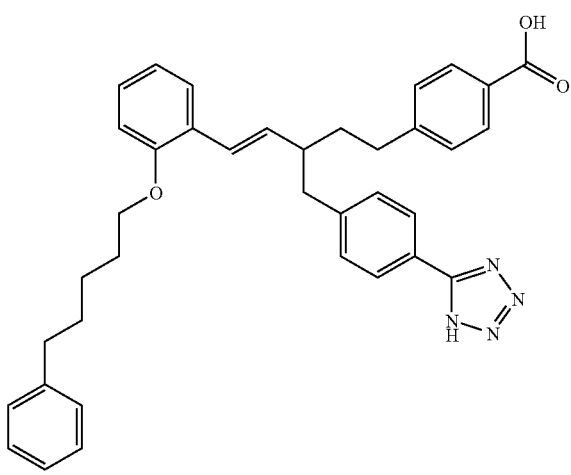

Enantiomer Separation Method: See Example 14.

$R_t$ 6.60 min; purity 99%; >98% ee

Yield: 17 mg $^1$H-NMR (300 MHz, DMSO-$d_6$, δ/ppm): 12.77 (1H, broad), 7.91 (2H, d), 7.85 (2H, d), 7.42-7.33 (4H, m), 7.3 (2H, d), 7.26-7.17 (2H, m), 7.17-7.1 (4H, m), 6.95-6.83 (2H, m), 6.44 (1H, d), 6.17-6.06 (1H, m), 3.96-3.82 (2H, m), 2.93-2.82 (1H, m), 2.81-2.69 (2H, m), 2.68-2.56 (2H, m), 1.90-1.76 (1H, m), 1.76-1.62 (3H, m), 1.62-1.48 (2H, m), 1.46-1.28 (2H, m), 1.27-1.19 (1H, s).

LC-MS (method 1): $R_t$=3.20 min.

MS (ESIpos): m/z=587 (M+H)$^+$.

84

Example 16

4-{(4E/Z)-5-{5-Fluoro-2-[2-(4-methoxyphenyl)ethyl]phenyl}-3-[4-(1H-tetrazol-5-yl)benzyl]pent-4-en-1-yl}benzoic acid

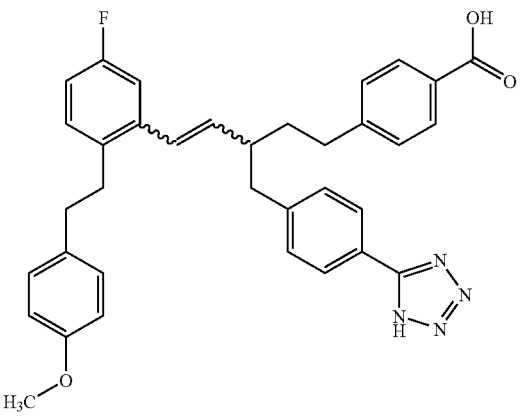

A solution of 92 mg (0.16 mmol) of methyl 4-{(4E/Z)-5-{5-fluoro-2-[2-(methoxyphenyl)ethyl]phenyl}-3-[4-(1H-tetrazol-5-yl)benzyl]pent-4-en-1-yl}benzoate in 5 ml of THF and 5 ml of water is mixed with 7.5 mg (0.31 mmol) of lithium hydroxide and stirred at 50° C. for 12 h. After cooling, the THF is stripped off and the aqueous phase is adjusted to pH 3 with 1 M hydrochloric acid. It is then extracted three times with ethyl acetate, and the combined organic phases are dried over sodium sulfate. After filtration and concentration 79 mg (0.14 mmol, 88% of theory) of a white foam are obtained.

MS (ESIpos): m/z=577 (M+H$^+$).

70 mg (0.12 mmol) of 4-{(4E/Z)-5{5-fluoro-2-[2-(4-methoxyphenyl)ethyl]phenyl}-3-[4-(1H-tetrazol-5-yl)benzyl]pent-4-en-1-yl}benzoic acid are fractionated further by preparative HPLC on a chiral phase. Respectively 23 mg and 44 mg of the Z and E isomers are obtained as colorless solids (see Examples 17 and 18).

Example 17

4-{(4Z)-5-{5-Fluoro-2-[2-(4-methoxyphenyl)ethyl]phenyl}-3-[4-(1H-tetrazol-5-yl)benzyl]pent-4-en-1-yl}benzoic acid

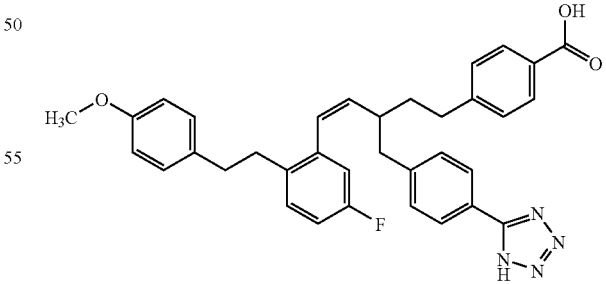

E/Z Isomer Separation Method:

Column: Daicel Chiralpak AD-H 250×20 mm; eluent: isohexane (with 1% water and 0.2% trifluoroacetic acid)/ethanol 60:40 (v/v); flow rate: 15 ml/min; UV detection: 215 nm; temperature: 25° C.

$R_t$ 5.276 min; purity 98.5%

Yield after separation: 23 mg

¹H-NMR (400 MHz, DMSO-d₆, δ/ppm): 16.9-16.5 (1H, broad), 13-12.5 (1H, broad), 7.87 (2H, d), 7.77 (2H, d), 7.26 (2H, d), 7.16 (2H, d), 7.14-7.07 (1H, m), 6.97-6.89 (3H, m), 6.73 (2H, d), 6.47 (1H, d), 6.22 (1H, d), 5.74-5.64 (1H, m), 3.68 (3H, s), 2.94-2.85 (1H, m), 2.76-2.61 (4H, m), 1.85-1.61 (2H, m).

Example 18

4-{(4E)-5-{5-Fluoro-2-[2-(4-methoxyphenyl)ethyl]phenyl}-3-[4-(1H-tetrazol-5-yl)benzyl]pent-4-en-1-yl}benzoic acid

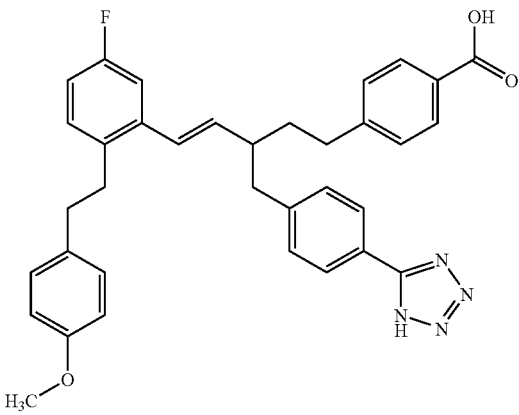

E/Z Isomer Separation Method: See Example 17.
R_t 5.286 min; purity 99%
Yield: 44 mg
¹H-NMR (400 MHz, DMSO-d₆, δ/ppm): 16.65 (1H, broad), 12.75 (1H, broad), 7.88 (2H, d), 7.84 (2H, d), 7.39 (2H, d), 7.31 (2H, d), 7.25-7.19 (1H, m), 7.12-7.06 (1H, m), 6.97-6.9 (1H, m), 6.88 (2H, d), 6.69 (2H, d), 6.37 (1H, d), 6.15-6.06 (1H, m), 3.67 (3H, s), 2.97-2.9 (1H, m), 2.8-2.6 (4H, m), 1.9-1.71 (2H, m).

Example 19

4-[(4E)-3-[4-(1H-Tetrazol-5-yl)benzyl]-5-(2-{[4'-(trifluoromethyl)biphenyl-4-yl]-methoxy}phenyl)pent-4-en-1-yl}benzoic acid

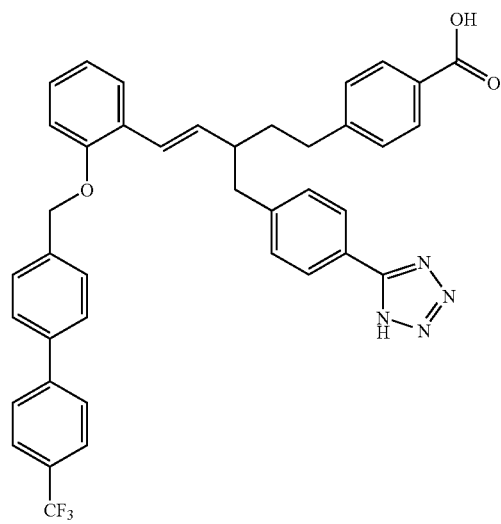

A solution of 384 mg (0.42 mmol) of methyl 4-[(4E)-3-[4-(1H-tetrazol-5-yl)benzyl]-5-(2-{[4'-(trifluoromethyl)biphenyl-4-yl]methoxy}phenyl)pent-4-en-1-yl]benzoate in 10 ml of THF and 10 ml of water is mixed with 20.3 mg (0.85 mmol) of lithium hydroxide and stirred at 50° C. for 12 h. After cooling, the THF is stripped off and the aqueous phase is adjusted to pH 3 with 1 M hydrochloric acid. It is then extracted three times with ethyl acetate, and the combined organic phases are dried over sodium sulfate. The residue obtained after filtration and concentration is purified by preparative HPLC. 141 mg (0.21 mmol, 46% of theory) of a white foam are obtained.

MS (ESIpos): m/z=675 (M+H⁺).

120 mg (0.12 mmol) of 4-[(4E)-3-[4-(1H-tetrazol-5-yl)benzyl]-5-(2-{[4'-(trifluoromethyl)biphenyl-4-yl]methoxy}phenyl)pent-4-en-1-yl]benzoic acid are further fractionated by preparative HPLC on a chiral phase. Respectively 50 mg and 35 mg of the two E isomers, each enantiopure, are obtained as colourless solids (see Examples 20 and 21).

Example 20

4-[(4E)-3-[4-(1H-Tetrazol-5-yl)benzyl]-5-(2-{[4'-(trifluoromethyl)biphenyl-4-yl]-methoxy}phenyl)pent-4-en-1-yl]benzoic acid (Enantiomer 1)

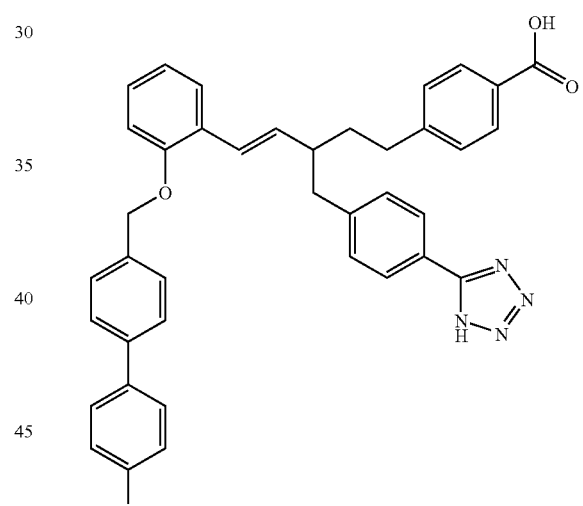

Enantiomer Separation Method:
Column: Daicel Chiralpak AD-H 250×20 mm; eluent: isohexane (with 1% water and 0.2% trifluoroacetic acid)/isopropanol 60:40 (v/v); flow rate: 15 mL/min; UV detection: 215 nm; temperature: 25° C.

R_t 6.65 min; purity 89%; >97.5% ee
Yield: 50 mg
¹H-NMR (400 MHz, DMSO-d₆, δ/ppm): 16.7 (1H, broad), 12.8 (1H, s), 7.91 (2H, d), 7.86-7.77 (6H, m), 7.66 (2H, d), 7.52-7.43 (3H, m), 7.39 (2H, d), 7.27 (2H, d), 7.23-7.16 (1H, m), 7.06 (1H, d), 6.95-6.89 (1H, m), 6.54 (1H, d), 6.21-6.12 (1H, m), 5.2-5.1 (2H, m), 2.92-2.85 (1H, m), 2.8-2.7 (2H, m), 2.69 (1H, m), 2.58 (1H, m), 1.88-1.77 (1H, m), 1.77-1.64 (1H, m).

Example 21

4-[(4E)-3-[4-(1H-Tetrazol-5-yl)benzyl]-5-(2-{[4'-(trifluoromethyl)biphenyl-4-yl]-methoxy}phenyl)pent-4-en-1-yl]benzoic acid (Enantiomer 2)

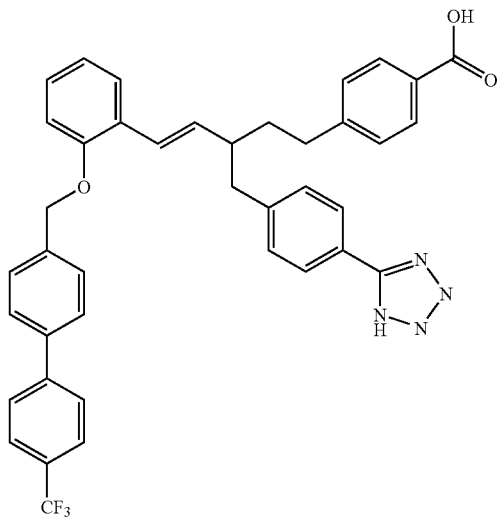

Enantiomer Separation Method: See Example 20.

$R_t$ 7.37 min; purity 99%; >98% ee

Yield: 35 mg $^1$H-NMR (400 MHz, DMSO-$d_6$, δ/ppm): 16.7 (1H, broad), 12.8 (1H, s), 7.91 (2H, d), 7.86-7.77 (6H, m), 7.66 (2H, d), 7.52-7.43 (3H, m), 7.39 (2H, d), 7.27 (2H, d), 7.23-7.16 (1H, m), 7.06 (1H, d), 6.95-6.89 (1H, m), 6.54 (1H, d), 6.21-6.12 (1H, m), 5.2-5.1 (2H, m), 2.92-2.85 (1H, m), 2.8-2.7 (2H, m), 2.69 (1H, m), 2.69-2.6 (1H, m), 1.88-1.77 (1H, m), 1.77-1.64 (1H, m).

Example 22

4-{(4E)-5-{2-[(4-tert-Butylbenzyl)oxy]phenyl}-3-[4-(1H-tetrazol-5-yl)benzyl]pent-4-en-1-yl}benzoic acid

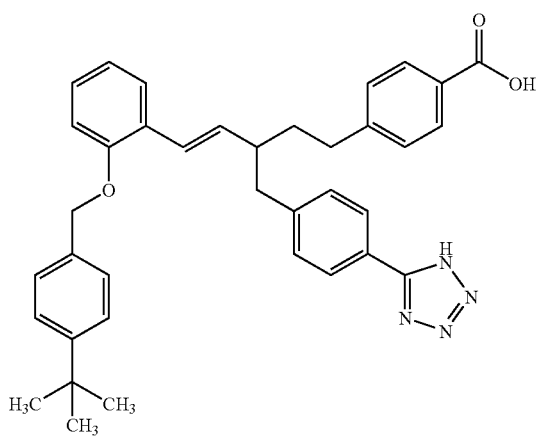

A solution of 70 mg (0.12 mmol) of methyl 4-{(4E)-5-{2-[(4-tert-butylbenzyl)oxy]phenyl}-3-[4-(1H-tetrazol-5-yl)benzyl]pent-4-en-1-yl}benzoate in 0.5 ml of THF and 0.25 ml of water is mixed with 11.16 mg (0.47 mmol) of lithium hydroxide and stirred at 60° C. for 12 h. After cooling, the THF is stripped off and the aqueous phase is adjusted to pH 2 with 1 M hydrochloric acid. It is then extracted three times with ethyl acetate, and the combined organic phases are dried over sodium sulfate. The residue obtained after filtration and concentration is purified by preparative HPLC. 45 mg (0.0761 mmol, 66% of theory) of a white foam are obtained.

$^1$H-NMR (400 MHz, DMSO-$d_6$, δ/ppm): 16.72 (1H, broad), 12.77 (1H, broad), 7.89 (2H, d), 7.82 (2H, d), 7.42 (1H, d), 7.37-7.23 (8H, m), 7.17 (1H, t), 7.04 (1H, d), 6.9 (1H, t), 6.52 (1H, d), 6.14 (1H, dd), 5.09-4.99 (2H, m), 2.90-2.81 (1H, m), 2.79-2.69 (2H, m), 2.69-2.57 (2H, m), 1.87-1.76 (2H, m), 1.74-1.61 (1H, m), 1.23 (9H, s).

45 mg (0.076 mmol) of 4-{(4E)-5-{2-[(4-tert-butylbenzyl)oxy]phenyl}-3-[4-(1H-tetrazol-5-yl)benzyl]pent-4-en-1-yl}benzoic acid are further fractionated by preparative HPLC on a chiral phase. 16 mg and 18 mg of the two E isomers, each enantiopure, are obtained as colorless solids (see Examples 23 and 24).

Example 23

4-{(4E)-5-{2-[(4-tert-Butylbenzyl)oxy]phenyl}-3-[4-(1H-tetrazol-5-yl)benzyl]pent-4-en-1-yl}benzoic acid (Enantiomer 1)

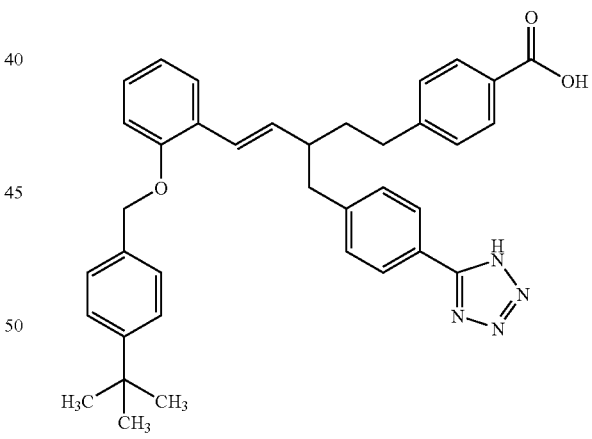

Enantiomer Separation Method:

Column: Daicel Chiralpak AD-H 250×20 mm; eluent: isohexane (with 1% water and 1% acetic 5 acid)/isopropanol 50:50 (v/v); flow rate: 15 ml/min; UV detection: 220 nm; temperature: 25° C.

$R_t$ 5.92 min; purity 99%; >99% ee

Yield: 16 mg.

Example 24

4-{(4E)-5-{2-[(4-tert-Butylbenzyl)oxy]phenyl}-3-[4-(1H-tetrazol-5-yl)benzyl]pent-4-en-1-yl}benzoic acid (Enantiomer 2)

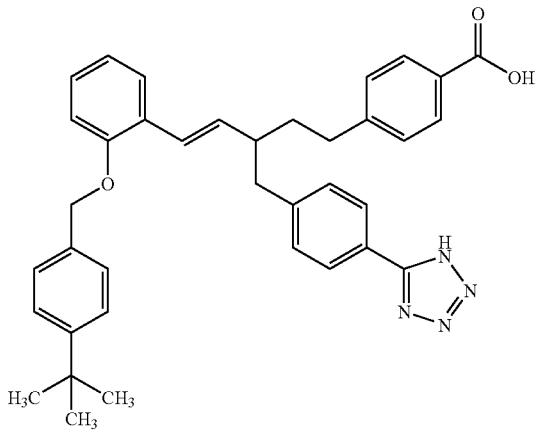

Enantiomer Separation Method: See Example 23.
R$_t$ 6.58 min; purity 99%; >96% ee
Yield: 18 mg.

The examples listed in the following table are obtained in an analogous manner:

Example 25

4-[3-((E)-2-{2-[(4-tert-Butylbenzyl)oxy]phenyl}vinyl)-7-(1H-tetrazol-5-yl)heptyl]benzoic acid

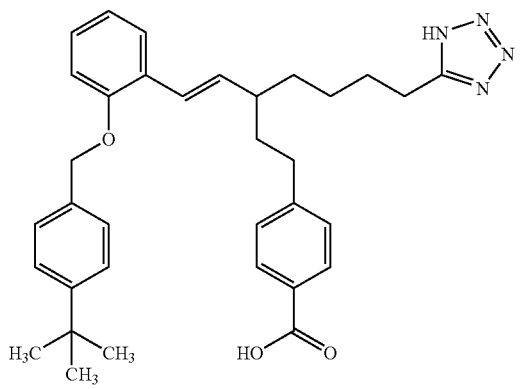

A solution of 181 mg (0.32 mmol) of methyl 4-[3-((E)-2-{2-[(4-tert-butylbenzyl)oxy]phenyl}vinyl)-7-(1H-tetrazol-5-yl)heptyl]benzoate in 5 ml of THF and 5 ml of water is mixed with 61.18 mg (2.55 mmol) of lithium hydroxide and stirred at 60° C. for 12 h. After cooling, the THF is stripped off and the aqueous phase is adjusted to pH 2 with 1 M hydrochloric acid. It is then extracted three times with ethyl acetate, and the combined organic phases are dried over sodium sulfate. The residue obtained after filtration and concentration is purified by preparative HPLC. 65 mg (0.12 mmol, 36.8% of theory) of a white foam are obtained.

$^1$H-NMR (400 MHz, DMSO-d$_6$, δ/ppm): 15.89 (1H, broad), 12.77 (1H, broad), 7.83 (2H, d), 7.46 (1H, d), 7.42-7.32 (4H, m), 7.28 (2H, d), 7.24-7.16 (1H, m), 7.16-7.0 (1H, m), 6.92 (1H, t), 6.64 (1H, d), 6.05 (1H, dd), 5.11 (2H, s), 2.84 (2H, t), 2.73-2.64 (1H, m), 2.63-2.56 (1H, m), 2.17-2.05 (1H, m), 1.79-1.54 (4H, m), 1.53-1.42 (1H, m), 1.42-1.14 (12H, m).

LC-MS (method 2): R$_t$=2.83 min.
MS (ESIpos): m/z=553 (M+H)$^+$.

73 mg (0.13 mmol) of 4-[3-((E)-2-{2-[(4-tert-butylbenzyl)oxy]phenyl}vinyl)-7-(1H-tetrazol-5-yl)heptyl]benzoic acid are further fractionated by preparative HPLC on a chiral phase. 31 mg of each of the two E isomers, enantiopure, are obtained as colorless solids (see Examples 26 and 27).

Example 26

4-[3-((E)-2-{2-[(4-tert-Butylbenzyl)oxy]phenyl}vinyl)-7-(1H-tetrazol-5-yl)heptyl]benzoic acid (Enantiomer 1)

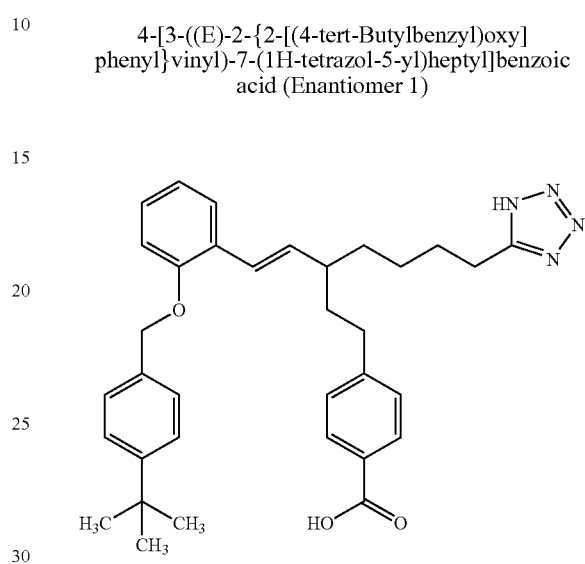

Enantiomer Separation Method:
Column: Daicel Chiralpak AD-H 250×20 mm; eluent: isohexane (with 1% water and 0.2% acetic acid)/isopropanol 50:50 (v/v); flow rate: 15 ml/min; UV detection: 220 nm; temperature: 35° C.
R$_t$ 4.19 min; purity 99%; >99.5% ee
Yield: 31 mg
LC-MS (method 2): R$_t$=2.85 min.
MS (ESIpos): m/z=553 (M+H)$^+$.

Example 27

4-[3-((E)-2-f{2-[(4-tert-Butylbenzyl)oxy]phenyl}vinyl)-7-(1H-tetrazol-5-yl)heptyl]benzoic acid (Enantiomer 2)

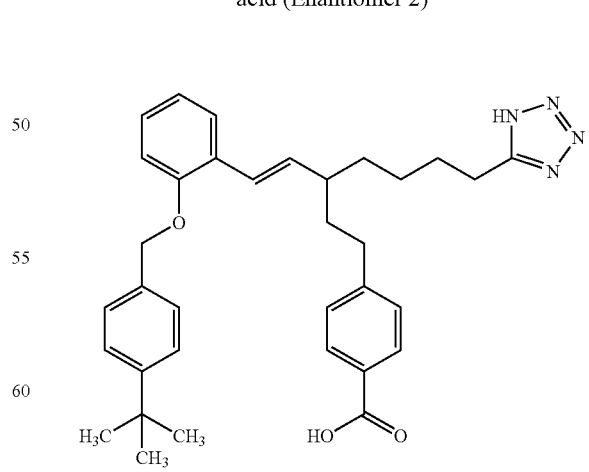

Enantiomer Separation Method: See Example 26.
R$_t$ 4.92 min; purity 99%; >98.8% ee
Yield: 31 mg

Example 28

(7E)-8-{2-[(4-tert-Butylbenzyl)oxy]phenyl}-6-{2-[4-(1H-tetrazol-5-yl)phenyl]ethyl}oct-7-enoic acid

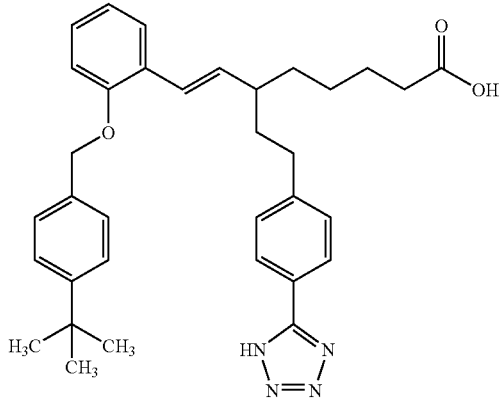

A solution of 600 mg (0.61 mmol) of ethyl (7E)-8-{2-[(4-tert-butylbenzyl)oxy]phenyl}-6-{2-[4-(1H-tetrazol-5-yl)phenyl]ethyl}oct-7-enoate in 20 ml of THF and 20 ml of water is mixed with 29.2 mg (1.22 mmol) of lithium hydroxide and stirred at 50° C. for 12 h. After cooling, the THF is stripped off and the aqueous phase is adjusted to pH 3 with 1 M hydrochloric acid. It is then extracted three times with ethyl acetate, and the combined organic phases are dried over sodium sulfate. The residue obtained after filtration and concentration is purified by preparative HPLC. 205 mg (0.37 mmol, 59.6% of theory) of a white foam are obtained.

MS (ESIpos): m/z=553 (M+H)$^+$.

200 mg (0.36 mmol) of (7E)-8-{2-[(4-tert-butylbenzyl)oxy]phenyl}-6-{2-[4-(1H-tetrazol-5-yl)phenyl]ethyl}oct-7-enoic acid are further fractionated by preparative HPLC on a chiral phase. 69 mg of each of the two E isomers, enantiopure, are obtained as colorless solids (see Examples 29 and 30).

Example 29

(7E)-8-{2-[(4-tert-Butylbenzyl)oxy]phenyl}-6-{2-[4-(1H-tetrazol-5-yl)phenyl]ethyl}oct-7-enoic acid (Enantiomer 1)

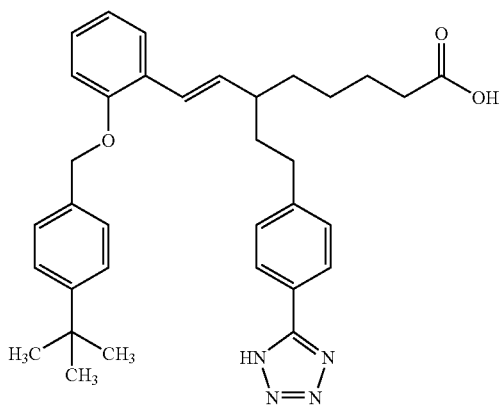

Enantiomer Separation Method:
Column: Daicel Chiralpak AD-H 250×20 mm; eluent: isohexane (with 1% water and 0.2% acetic acid)/isopropanol 80:20 (v/v); flow rate: 15 ml/min; UV detection: 220 nm; temperature: 35° C.

$R_t$ 7.03 min; purity 99.5%; >97.5% ee
Yield: 69 mg $^1$H-NMR (300 MHz, DMSO-d$_6$, δ/ppm): 11.96 (1H, broad), 7.92 (2H, d), 7.47 (1H, d), 7.44-7.33 (6H, m), 7.2 (1H, t), 7.09 (1H, d), 6.91 (1H, t), 6.64 (1H, d), 6.13-6.01 (1H, m), 5.11 (2H, s), 2.78-2.54 (2H, m), 2.22-2.05 (2H, m), 1.84-1.69 (1H, m), 1.69-1.56 (1H, m), 1.54-1.38 (4H, m), 1.38-1.16 (3H, m).

LC-MS (method 2): $R_t$=2.92 min.
MS (ESIpos): m/z=553 (M+H)$^+$.

Example 30

(7E)-8-{2-[(4-tert-Butylbenzyl)oxy]phenyl}-6-{2-[4-(1H-tetrazol-5-yl)phenyl]ethyl}oct-7-enoic acid (Enantiomer 2)

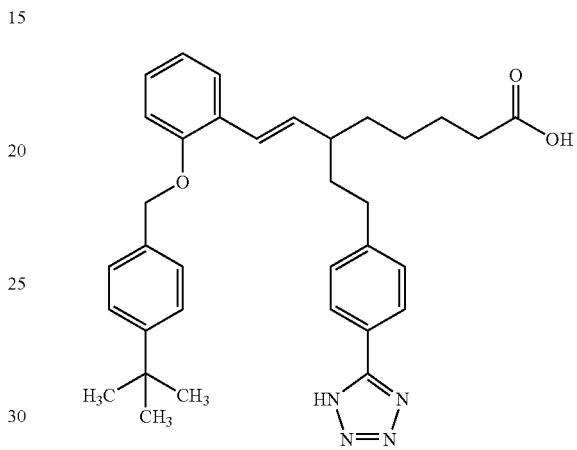

Enantiomer Separation Method: See Example 29.

$R_t$ 7.89 min; purity 99.5%; >98.5% ee
Yield: 69 mg $^1$H-NMR (300 MHz, DMSO-d$_6$, δ/ppm): 11.95 (1H, broad), 7.91 (2H, d), 7.48 (1H, d), 7.44-7.33 (6H, m), 7.2 (1H, t), 7.09 (1H, d), 6.91 (1H, t), 6.64 (1H, d), 6.13-6.01 (1H, m), 5.11 (2H, s), 2.78-2.54 (2H, m), 2.22-2.05 (2H, m), 1.84-1.69 (1H, m), 1.69-1.56 (1H, m), 1.54-1.38 (4H, m), 1.38-1.16 (3H, m).

LC-MS (method 2): $R_t$=2.93 min.
MS (ESIpos): m/z=553 (M+H)$^+$.

Example 31

(7E)-8-{2-[(5-Phenylpentyl)oxy]phenyl}-6-{2-[4-(1H-tetrazol-5-yl)phenyl]ethyl}oct-7-enoic acid

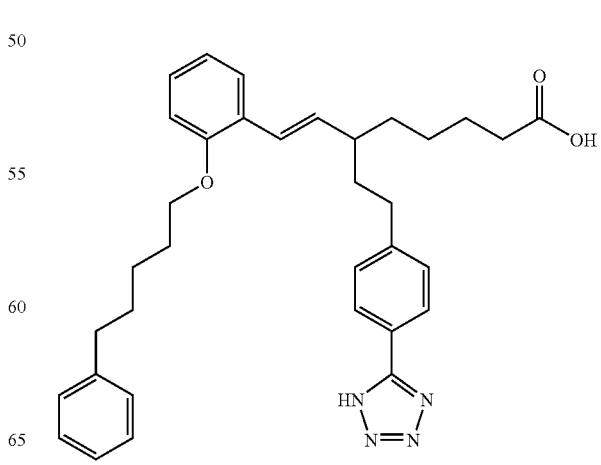

A solution of 62 mg (0.11 mmol) of ethyl (7E)-8-{2-[(5-phenylpentyl)oxy]phenyl}-6-{2-[4-(1H-tetrazol-5-yl)phenyl]ethyl}oct-7-enoate in 5 ml of THF and 5 ml of water is mixed with 5.11 mg (0.21 mmol) of lithium hydroxide and stirred at 50° C. for 12 h. After cooling, the THF is stripped off and the aqueous phase is adjusted to pH 3 with 1 M hydrochloric acid. It is then extracted three times with ethyl acetate, and the combined organic phases are dried over sodium sulfate. After filtration and concentration, 34 mg (0.06 mmol, 57.6% of theory) of a white foam are obtained.

$^1$H-NMR (400 MHz, DMSO-$d_6$, δ/ppm): 11.95 (1H, broad), 7.93 (2H, d), 7.43 (1H, d), 7.4 (2H, d), 7.3-7.1 (6H, m), 6.97 (1H, d), 6.38 (1H, t), 6.58 (1H, d), 6.05 (1H, dd), 4.0 (2H, t), 2.75-2.65 (1H, m), 2.22-2.05 (3H, m), 1.83-1.7 (3H, m), 1.7-1.57 (3H, m), 1.57-1.4 (6H, m), 1.4-1.15 (5H, m).

30 mg (0.054 mmol) of (7E)-8-{2-[(5-phenylpentyl)oxy]phenyl}-6-{2-[4-(1H-tetrazol-5-yl)phenyl]ethyl}oct-7-enoic acid are further fractionated by preparative HPLC on a chiral phase. 10 mg of each of the two E isomers, enantiopure, are obtained as colorless solids (see Examples 32 and 33).

Example 32

(7E)-8-{2-[(5-Phenylpentyl)oxy]phenyl}-6-{2-[4-(1H-tetrazol-5-yl)phenyl]ethyl}oct-7-enoic acid (Enantiomer 1)

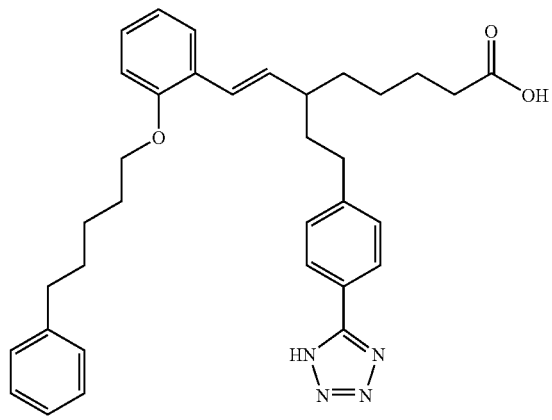

Enantiomer Separation Method:

Column: Daicel Chiralpak AD-H 250×20 mm; eluent: isohexane (with 1% water and 0.2% acetic acid)/isopropanol 80:20 (v/v); flow rate: 15 ml/min; UV detection: 215 nm; temperature: 25° C.

$R_t$ 6.07 min; purity 99%; >99% ee

Yield: 10 mg $^1$H-NMR (300 MHz, DMSO-$d_6$, δ/ppm): 11.95 (1H, broad), 8.96 (2H, d), 7.45 (3H, d), 7.27-7.07 (6H, m), 6.97 (1H, d), 6.39 (1H, t), 6.57 (1H, d), 6.07 (1H, dd), 4.0 (2H, t), 2.78-2.5 (3H, m), 2.22-2.01 (3H, m), 1.85-1.16 (16H, m).

Example 33

(7E)-8-{2-[(5-Phenylpentyl)oxy]phenyl}-6-{2-[4-(1H-tetrazol-5-yl)phenyl]ethyl}oct-7-enoic acid (Enantiomer 2)

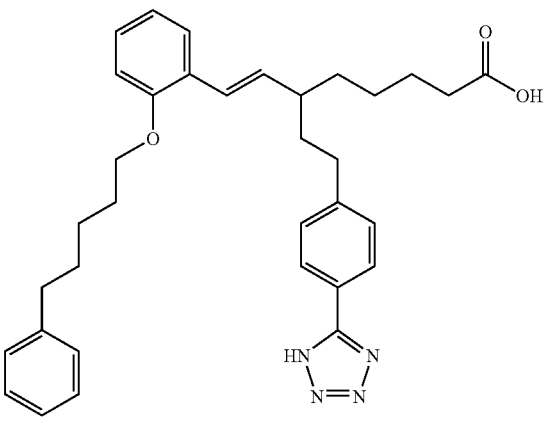

Enantiomer Separation Method: See Example 32.

$R_t$ 7.05 min; purity 99%; >98.5% ee

Yield: 10 mg $^1$H-NMR (300 MHz, DMSO-$d_6$, δ/ppm): 11.95 (1H, broad), 8.96 (2H, d), 7.45 (3H, d), 7.27-7.07 (6H, m), 6.97 (1H, d), 6.39 (1H, t), 6.57 (1H, d), 6.07 (1H, dd), 4.0 (2H, t), 2.78-2.5 (3H, m), 2.22-2.01 (3H, m), 1.85-1.16 (16H, m).

Example 34

(7E)-8-{2-[(4-tert-Butylbenzyl)oxy]phenyl}-6-[4-(1H-tetrazol-5-yl)benzyl]oct-7-enoic acid

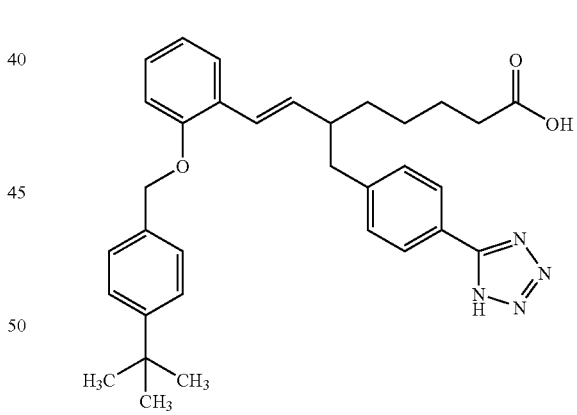

A solution of 800 mg (1.41 mmol) of ethyl (7E)-8-{2-[(4-tert-butylbenzyl)oxy]phenyl}-6-[4-(1H-tetrazol-5-yl)benzyl]oct-7-enoate in 10 ml of THF and 10 ml of water is mixed with 67.6 mg (2.82 mmol) of lithium hydroxide and stirred at 50° C. for 12 h. After cooling, the THF is stripped off and the aqueous phase is adjusted to pH 3 with 1 M hydrochloric acid. It is then extracted three times with ethyl acetate, and the combined organic phases are dried over sodium sulfate. The residue obtained after filtration and concentration is purified by preparative HPLC. 660 mg (1.2 mmol, 87% of theory) of a white foam are obtained.

LC-MS (method 4): $R_t$=2.51 min.

MS (ESIpos): m/z=539 (M+H)$^+$.

700 mg (1.3 mmol) of (7E)-8-{2-[(4-tert-butylbenzyl)oxy]phenyl}-6-[4-(1H-tetrazol-5-yl)benzyl]oct-7-enoic acid are further fractionated by preparative HPLC on a chiral phase. Respectively 318 mg and 257 mg of the two E isomers, each enantiopure, are obtained as colorless solids (see Examples 35 and 36).

Example 35

(7E)-8-{2-[(4-tert-Butylbenzyl)oxy]phenyl}-6-[4-(1H-tetrazol-5-yl)benzyl]oct-7-enoic acid (Enantiomer 1)

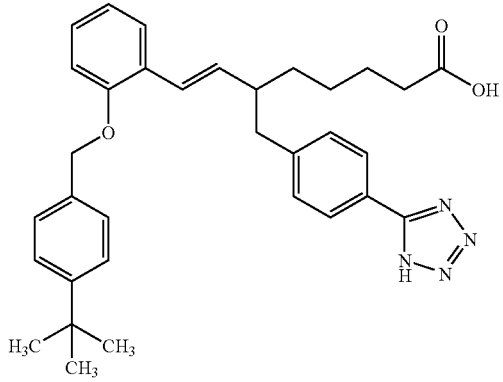

Enantiomer Separation Method:

Column: Daicel Chiralpak AD-H 250×20 mm; eluent: isohexane (with 1% water and 0.2% acetic acid)/isopropanol 65:35 (v/v); flow rate: 15 ml/min; UV detection: 220 nm; temperature: 35° C.

$R_t$ 4.18 min; purity 99%; >99.5% ee

Yield: 318 mg $^1$H-NMR (400 MHz, DMSO-$d_6$, δ/ppm): 12.85 (1H, broad), 11.98 (1H, broad), 7.7 (2H, d), 7.38 (5H, d), 7.25 (2H, d), 7.15 (1H, t), 7.0 (1H, d), 6.88 (1H, t), 6.43 (1H, d), 6.07 (1H, dd), 5.03 (2H, s), 2.88 (1H, m), 2.69 (1H, t), 1.54-1.3 (6H, m), 1.28 (10H, m).

Example 36

(7E)-8-{2-[(4-tert-Butylbenzyl)oxy]phenyl}-6-[4-(1H-tetrazol-5-yl)benzyl]oct-7-enoic acid (Enantiomer 2)

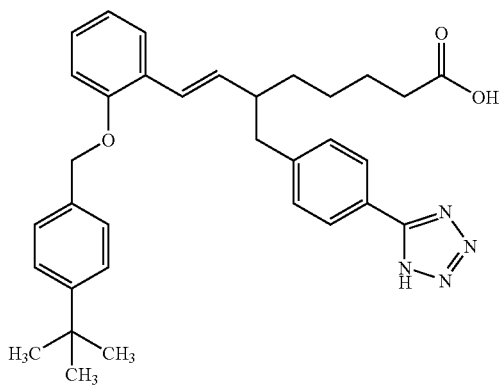

Enantiomer separation method: see Example 35.

$R_t$ 5.00 min; purity 99%; >99.4% ee

Yield: 257 mg $^1$H-NMR (400 MHz, DMSO-$d_6$, δ/ppm): 11.98 (1H, broad), 7.9 (2H, d), 7.4 (3H, d), 7.32 (2H, d), 7.26 (2H, d), 7.16 (1H, t), 7.0 (1H, d), 6.89 (1H, t), 6.46 (1H, d), 6.08 (1H, dd), 2.88-2.8 (1H, m), 2.72-2.63 (1H, m), 2.18 (2H, t), 1.56-1.3 (6H, m), 1.3-1.22 (10H, m).

Example 37

(7E/Z)-8-{2-[(5-Phenylpentyl)oxy]phenyl}-6-[4-(1H-tetrazol-5-yl)benzyl]oct-7-enoic acid

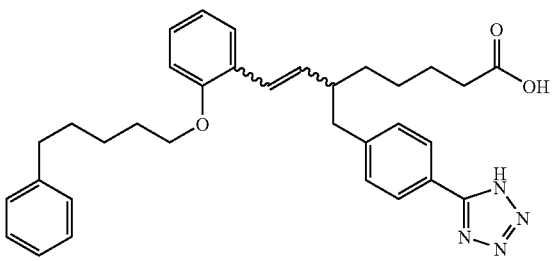

A solution of 36 mg (0.06 mmol) of ethyl (7E/Z)-8-{2-[(5-Phenylpentyl)oxy]phenyl}-6-[4-(1H-tetrazol-5-yl)benzyl]oct-7-enoate in 5 ml of methanol is mixed with 0.5 ml of 45% sodium hydroxide solution and stirred at room temperature for 2 h. The methanol is then stripped off and the residue is taken up in water/ethyl acetate. The mixture is adjusted to pH 3 with 1 M hydrochloric acid. The phases are separated and the aqueous phase is extracted two more times with ethyl acetate. The combined organic phases are washed with saturated sodium chloride solution and dried over sodium sulfate. The residue obtained after filtration and concentration is purified by preparative HPLC. 14.7 mg (0.03 mmol, 43% of theory) of a colorless foam are obtained.

$^1$H-NMR (300 MHz, CDCl$_3$, δ/ppm): (E/Z=2:1) 7.92 (1.06H, d), 7.87 (0.53H, d), 7.38-7.21 (4H, m), 7.21-7.09 (4H, m), 6.93-6.72 (3H, m), 6.59 (0.53H, d), 6.49 (0.26H, d), 6.07-5.95 (0.53H, m), 5.44-5.36 (0.26H, t), 3.99-3.89 (1.06H, t), 3.89-3.79 (0.53H, m), 2.86-2.73 (2H, m), 2.65-2.57 (2H, t), 2.54-2.43 (1H, m), 2.34-2.26 (1.06H, t), 2.26-2.18 (0.53H, m), 1.85-1.73 (2H, m), 1.73-1.55 (2H, m), 1.55-1.23 (6H, m).

The examples given in the following table are obtained in an analogous manner:

| Example No. | Structure of example [precursors] | Analytical data |
|---|---|---|
| 38 | 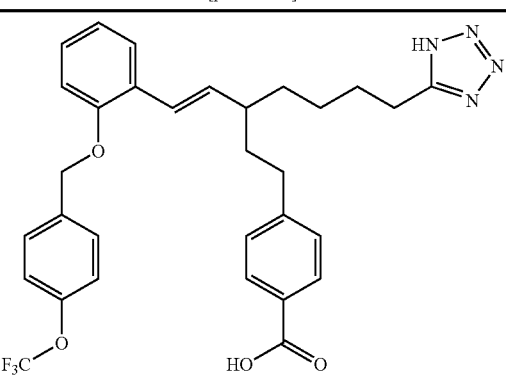<br>(Racemate)<br>[starting from Ex. 51A and 1-(bromomethyl)-4-(trifluoromethoxy)benzole | $^1$H-NMR (400 MHz, DMSO-$d_6$, δ/ppm): 15.89 (1H, br. s), 12.76 (1H, br. s), 7.82 (2H, d), 7.59 (2H, d), 7.47 (1H, d), 7.37 (2H, d), 7.28 (2H, d), 7.20 (1H, t), 7.08 (1H, d), 6.92 (1H, t), 6.62 (1H, d), 6.11-5.98 (1H, m), 5.18 (2H, s), 2.84 (2H, t), 2.73-2.41 (2H, m), 2.18-2.03 (1H, m), 1.80-1.53 (4H, m), 1.52-1.41 (1H, m), 1.40-1.20 (3H, m).<br>LC-MS (method 4): $R_t$ = 2.84 min: m/z = 581 (M + H$^+$). |
| 39 | 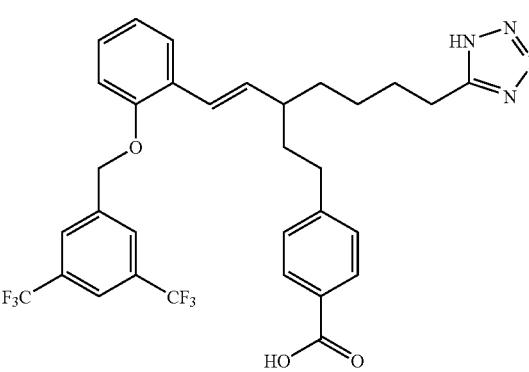<br>(Racemate)<br>[starting from Ex. 51A and 1-(bromomethyl)-3,5-bis(trifluoromethyl)benzole | LC-MS (method 6): $R_t$ = 2.99 min; m/z 633 (M + H$^+$). |

B. ASSESSMENT OF THE PHARMACOLOGICAL ACTIVITY

The pharmacological effect of the compounds according to the invention can be shown in the following assays:

B-1. Vasorelaxant Effect In Vitro:

Rabbits are anesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with 95% $O_2$/5% $CO_2$ and has the following composition: NaCl 119 mM; KCl 4.8 mM; $CaCl_2$×$2H_2O$ 1 mM; $MgSO_4$×$7H_2O$ 1.4 mM; $KH_2PO_4$ 1.2 mM; $NaHCO_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the height of the contraction achieved under the influence of the test substance is compared with the height of the contraction reached in the last preceding run. The concentration necessary to reduce the contraction reached in the preceding control by 50% is calculated from this ($IC_{50}$). The standard application volume is 5 μl. The proportion of DMSO in the bath solution corresponds to 0.1%.

Representative results on the compounds according to the invention are listed in Table 1:

TABLE 1

| Vasorelaxant effect in vitro | |
|---|---|
| Example No. | $IC_{50}$ [nM] |
| 3 | 682 |
| 5 | 2510 |
| 6 | 119 |
| 14 | 1324 |
| 17 | 5800 |
| 18 | 890 |
| 21 | 372 |
| 23 | 3888 |
| 24 | 102 |
| 26 | 559 |
| 27 | 9.7 |
| 29 | 1990 |

TABLE 1-continued

Vasorelaxant effect in vitro

| Example No. | IC$_{50}$ [nM] |
|---|---|
| 36 | 760 |
| 38 | 567 |
| 39 | 150 |

B-2. Stimulation of Recombinant Soluble Guanylate Cyclase (sGC) In Vitro:

Investigations on the stimulation of recombinant soluble guanylate cyclase (sGC) by the compounds according to the invention with and without sodium nitroprusside, and with and without the heme-dependent sGC inhibitor 1H-1,2,4-oxadiazole-(4,3a)-quinoxalin-1-one (ODQ) are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The heme-free guanylate cyclase is obtained by adding Tween 20 to the sample buffer (0.5% in the final concentration).

The activation of sGC by a test substance is reported as n-fold stimulation of the basal activity.

The result for Example 6 is shown in Table 2:

TABLE 2

Stimulation (n-fold) of recombinant soluble guanylate cyclase (sGC) in vitro by Example 6

| Concentration of Example 6 [μM] | Heme-containing sGC | | | Heme-free sGC | |
|---|---|---|---|---|---|
| | Basal | +0.1 μM DEA/NO | +10 μM ODQ | Basal | +10 μM ODQ |
| 0.0 | 1.0 | 64.1 | 2.4 | 1.0 | 1.2 |
| 0.001 | 1.9 | 62.0 | 4.8 | 3.2 | 3.0 |
| 0.01 | 5.1 | 66.0 | 25.7 | 20.4 | 18.9 |
| 0.1 | 20.2 | 80.0 | 102.7 | 90.9 | 89.7 |
| 1 | 29.5 | 96.2 | 125.8 | 143.8 | 143.8 |
| 10 | 42.1 | 99.9 | 135.0 | 145.9 | 149.3 |

[DEA/NO = 2-(N,N-diethylamino)diazenolate 2-oxide; ODQ = 1H-1,2,4-oxadiazole-(4,3a)-quinoxalin-1-one].

It is evident from Table 2 that stimulation both of the heme-containing and of the heme-free enzyme is achieved. Furthermore, combination of Example 6 and 2-(N,N-diethylamino)diazenolate 2-oxide (DEA/NO), an NO donor, shows no synergistic effect, i.e. the effect of DEA/NO is not potentiated as would be expected with an sGC activator acting via a heme-dependent mechanism. In addition, the effect of the sGC activator according to the invention is not blocked by the heme-dependent inhibitor of soluble guanylate cyclase ODQ, but is in fact increased. The results in Table 2 thus confirm the mechanism of action of the compounds according to the invention as activators of soluble guanylate cyclase.

B-3. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitter, (2) receiver which is linked via a multiplexer to a (3) data acquisition computer. The telemetry system makes it possible to record continuously the blood pressure and heart rate on conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 in the morning and at 19.00 in the evening.

The telemetry transmitters (TAM PA-C40, DSI) as employed are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi, 50 mg/kg i.p.) and shaved and disinfected over a large area on the side of the abdomen. After the abdominal cavity has been opened along the linea alba, the liquid-filled measuring catheter of the system is inserted into the descending aorta in the cranial direction above the bifurcation and fastened with tissue glue (VetBonD™, 3M). The transmitter housing is fixed intraperitoneally to the abdominal wall muscle, and layered closure of the wound is performed. An antibiotic (Tardomyocel COMP, Bayer, 1 ml/kg s.c.) is administered postoperatively for prophylaxis of the infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated from outside by means of an incorporated magnetic switch and are switched to transmission in the run-up to the experiment.

The emitted signals can be detected online by a data acquisition system (Dataquest™ A.R.T. for Windows, DSI) and be appropriately processed. The data are stored in each case in a file bearing the experiment number which is open for this purpose.

In the standard procedure, the following are measured for 10-second periods in each case: (1) systolic blood pressure (SBP), (2) diastolic blood pressure (DBP), (3) mean arterial pressure (MAP) and (4) heart rate (HR).

Measurement acquisition is repeated under computer control at 5-minute intervals. The source data obtained as absolute value are corrected in the diagram with the currently measured barometric pressure and stored in individual data. Further technical details are given in the documentation of the manufacturing company (DSI).

The test substances are administered at 9.00 h on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 h on the day of the experiment to 9.00 h on the following day.

The data are smoothed over a presettable time by determination of the average (15-minute average, 30-minute average) and transferred as text file to a storage medium. The measurements presorted and compressed in this way are transferred into Excel templates and tabulated.

The compound of Example 6 shows after oral administration of 10 mg/kg a marked reduction in blood pressure over a period of 11 hours in this test.

C. EXEMPLARY EMBODIMENTS OF PHARMACEUTICAL COMPOSITIONS

The compounds according to the invention can be converted into pharmaceutical preparations in the following ways:

Tablet:

Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

A mixture of compound according to the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which Can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which Can be Administered Orally:

Composition:

500 mg of the compound according to the invention, 2.5 g of polysorbate and 97 g of polyethylene glycol 400.20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

I.V.-Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

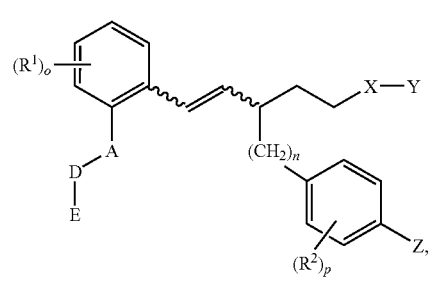

in which
A is O or $CH_2$,
D is a bond or is ($C_1$-$C_7$)-alkanediyl, ($C_2$-$C_7$)-alkenediyl or ($C_2$-C7)-alkynediyl,
E is hydrogen, trifluoromethyl or a group of the formula

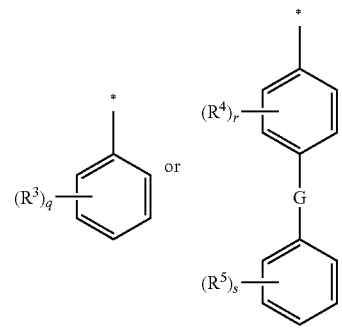

in which * means the point of linkage to the group D and
G is a bond, $CH_2$, —$CH_2$—$CH_2$— or —CH=CH—,
X is a group of the formula

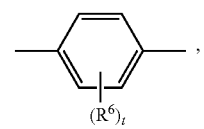

Y is carboxyl
and
Z is a group of the formula

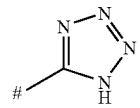

or
Y is a group of the formula

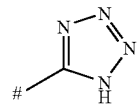

in which # means the respective point of linkage, and

Z is carboxyl, n is the number 1 or 2, $R^1, R^2, R^3, R^4, R^5$ and $R^6$ are independently of one another substituents selected from the series halogen, $(C_1-C_6)$-alkyl, trifluoromethyl, $(C_1-C_6)$-alkoxy, trifluoromethoxy, cyano and nitro, and o, p, q, r, s and t are independently of one another each the number 0, 1, 2, 3 or 4, where in the case where $R^1, R^2, R^3, R^4, R^5$ or $R^6$ occur more than once, their meanings may in each case be identical or different, or a salt thereof.

2. The compound of the formula (I) as claimed in claim 1, in which

A is O,

D is $(C^1-C^7)$-alkanediyl,

E is hydrogen, trifluoromethyl or is a group of the formula

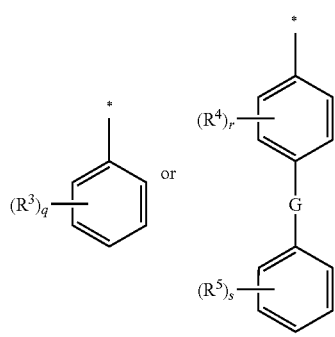

in which * means the point of linkage to the group D,

X is a group of the formula

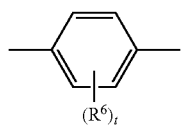

Y is carboxyl and

Z is a group of the formula

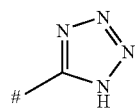

or

Y is a group of the formula

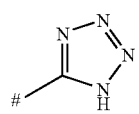

in which # means the respective point of linkage, and

Z is carboxyl, n is the number 1 or 2, $R^1, R^3, R^4$ and $R^5$ are independently of one another a substituent selected from the series fluorine, chlorine, bromine, $(C_1-C_4)$-alkyl, trifluoromethyl, $(C_1-C_4)$-alkoxy and trifluoromethoxy, o, q, r and s are independently of one another each the number 0, 1 or 2, where in the case where $R^1, R^3, R^4$ or $R^5$ occur more than once, their meanings may in each case be identical or different, $R^2$ and $R^6$ are each fluorine, and p and t are independently of one another each the number 0 or 1, or a salt thereof.

3. A process for preparing a compound of the formula (I) of claim 1, comprising:

[A] reacting a compound of the formula (II-1)

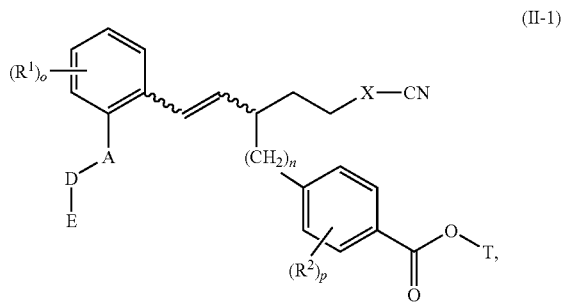

in which R1, R2, A, D, E, X, n, o and p each have the meanings indicated in claim 1, and T is (C1-C4)-alkyl, with an alkali metal azide or with trimethylsilyl azide in an inert solvent to give a compound of the formula (III-1)

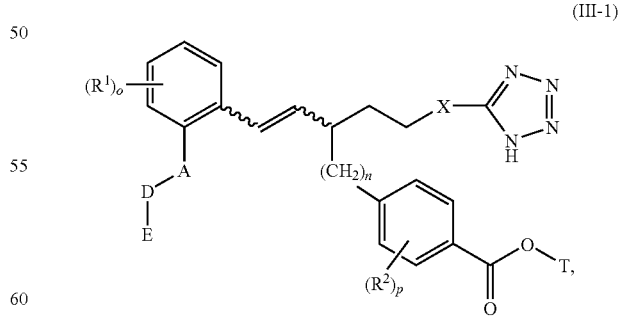

in which $R^1, R^2$, A, D, E, X, n, o, p and T each have the meanings indicated above, or

[B] reacting a compound of the formula (II-2)

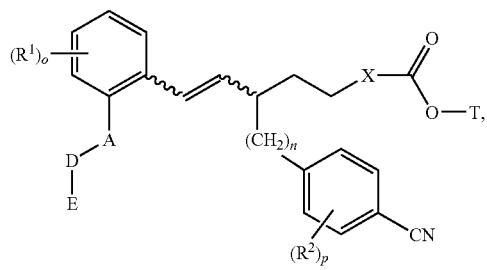

(II-2)

in which $R^1$, $R^2$, A, D, E, X, n, o, p and T each have the meanings indicated above, with an alkali metal azide or with trimethylsilyl azide in an inert solvent to give a compound of the formula (III-2)

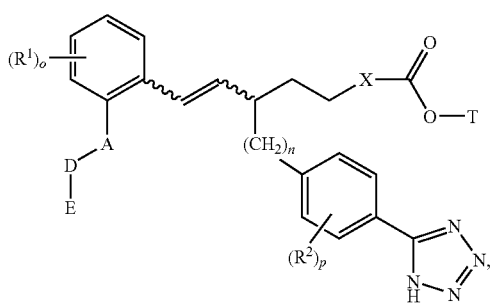

(III-2)

in which R1, R2, A, D, E, X, n, o, p and T each have the meanings indicated above, and converting the compound of formula (III-1) or (III 2) by hydrolysis of the ester group —C(O)OT into the corresponding carboxylic acid of the formula (I), and optionally reacting the compound of the formula (I) with an appropriate (i) solvent and/or (ii) base or acid to give a salt thereof.

4. A pharmaceutical composition comprising a compound of claim 1 and an inert, non-toxic, pharmaceutically suitable excipient.

5. The pharmaceutical composition of claim 4, further Comprising an active ingredient selected from the group consisting of an organic nitrate, an NO donor, a cGMP-PDE inhibitor, a stimulator of guanylate cyclase, an agent having antithrombotic activity, an agent lowering blood pressure, and an agent altering lipid metabolism.

6. A method for the treatment and/or prevention of heart failure, angina pectoris, hypertension, pulmonary hypertension, ischemias, and arteriosclerosis in humans and animals by administration of an effective amount of at least one compound as defined in claim 1.

7. A method for the treatment and/or prevention of heart failure, angina pectoris, hypertension, pulmonary hypertension, ischemias, and arteriosclerosis in humans and animals by administration of an effective amount of at least one pharmaceutical composition as defined in claim 4.

8. A method for the treatment and/or prevention of heart failure, angina pectoris, hypertension, pulmonary hypertension, ischemias, and arteriosclerosis in humans and animals by administration of an effective amount of at least one pharmaceutical composition as defined in claim 5.

* * * * *